United States Patent
Hall et al.

(10) Patent No.: US 10,765,378 B2
(45) Date of Patent: *Sep. 8, 2020

(54) METHOD AND SYSTEM FOR DETERMINING PHYSIOLOGICAL STATUS OF USERS BASED ON MARKER-LESS MOTION CAPTURE AND GENERATING APPROPRIATE REMEDIATION PLANS

(71) Applicant: Preaction Technology Corporation, Bozeman, MT (US)

(72) Inventors: Bradley Richard Hall, Bozeman, MT (US); Milica George-Ann McDowell, Bozeman, MT (US); Michael Erik Abrahamsen, Bozeman, MT (US); Joseph Nicholas Bergantine, Bozeman, MT (US)

(73) Assignee: PREACTION TECHNOLOGY CORPORATION, Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,659

(22) Filed: Feb. 20, 2019

(65) Prior Publication Data

US 2019/0175121 A1    Jun. 13, 2019

Related U.S. Application Data

(63) Continuation of application No. 15/441,654, filed on Feb. 24, 2017, now Pat. No. 10,255,677.
(Continued)

(51) Int. Cl.
*G06K 9/00* (2006.01)
*A61B 5/00* (2006.01)
(Continued)

(52) U.S. Cl.
CPC .......... *A61B 5/7435* (2013.01); *A61B 5/0077* (2013.01); *A61B 5/1124* (2013.01);
(Continued)

(58) Field of Classification Search
None
See application file for complete search history.

(56) References Cited

U.S. PATENT DOCUMENTS

| 7,369,889 B2 * | 5/2008 | Astrom ................... A61N 1/365 |
| | | 600/509 |
| 9,355,305 B2 * | 5/2016 | Tanabiki ................... G06T 7/75 |

(Continued)

FOREIGN PATENT DOCUMENTS

WO    WO 2015/150931    10/2015

OTHER PUBLICATIONS

International Preliminary Report on Patentability from App. No. PCT/US2017/019327 dated Sep. 7, 2018.
(Continued)

*Primary Examiner* — Shadan E Haghani
(74) *Attorney, Agent, or Firm* — Adsero IP

(57) ABSTRACT

Novel tools and techniques might provide for implementing image-based physiological status determination of users, and, in particular embodiments, for implementing physiological status determination of users based on marker-less motion-capture and generating appropriate remediation plans. In various embodiments, one or more cameras may be used to capture views of a user (e.g., an athlete, a person trying to live a healthy life, or the like) as the user is performing one or more set of motions, and the captured images may be overlaid with a skeletal framework that is compared with similar skeletal framework overlaid images for the same one or more sets of motions. The system can automatically determine a physical condition of the user or
(Continued)

a probability that the user will suffer a physical condition based at least in part on an analysis of the comparison, which may be difficult or impossible to observe with the naked human eye.

20 Claims, 40 Drawing Sheets

Related U.S. Application Data

(60) Provisional application No. 62/299,099, filed on Feb. 24, 2016.

(51) Int. Cl.
*H04N 5/232* (2006.01)
*A61B 5/11* (2006.01)
*H04N 5/225* (2006.01)
*G16H 50/20* (2018.01)
*G16H 30/40* (2018.01)
*G06K 9/52* (2006.01)
*G06K 9/62* (2006.01)
*G06T 5/00* (2006.01)
*G06T 7/00* (2017.01)
*H04N 5/247* (2006.01)
*H04N 5/265* (2006.01)
*G16H 50/30* (2018.01)

(52) U.S. Cl.
CPC ............ *A61B 5/1128* (2013.01); *A61B 5/458* (2013.01); *A61B 5/4533* (2013.01); *A61B 5/4595* (2013.01); *A61B 5/7275* (2013.01); *A61B 5/7278* (2013.01); *G06K 9/00342* (2013.01); *G06K 9/52* (2013.01); *G06K 9/6215* (2013.01); *G06T 5/00* (2013.01); *G06T 7/0012* (2013.01); *G16H 30/40* (2018.01); *G16H 50/20* (2018.01); *H04N 5/2258* (2013.01); *H04N 5/23206* (2013.01); *H04N 5/23293* (2013.01); *H04N 5/247* (2013.01); *H04N 5/265* (2013.01); *A61B 2503/10* (2013.01); *A61B 2562/04* (2013.01); *G16H 50/30* (2018.01)

(56) References Cited

U.S. PATENT DOCUMENTS

| | | |
|---|---|---|
| 2007/0103471 A1 | 5/2007 | Yang |
| 2008/0031512 A1 | 2/2008 | Mundermann |
| 2009/0232353 A1* | 9/2009 | Sundaresan ........ G06K 9/00342 382/103 |
| 2014/0219550 A1 | 8/2014 | Popa |
| 2014/0228985 A1 | 8/2014 | Elliott |
| 2014/0267611 A1* | 9/2014 | Kennett ............. G09B 19/0038 348/46 |
| 2015/0010202 A1 | 1/2015 | Tuzel |
| 2015/0019135 A1 | 1/2015 | Kacyvenski |
| 2016/0094961 A1* | 3/2016 | Agrawal ................. H04W 4/14 455/466 |
| 2016/0096509 A1 | 4/2016 | Ette |
| 2016/0125429 A1 | 5/2016 | Fanning |
| 2016/0232683 A1 | 8/2016 | Kim |
| 2017/0035330 A1* | 2/2017 | Bunn ................... A61B 5/1128 |
| 2017/0054569 A1 | 2/2017 | Harms |
| 2017/0185920 A1 | 6/2017 | Chawla |
| 2017/0243346 A1 | 8/2017 | Hall |

OTHER PUBLICATIONS

Office Action from U.S. Appl. No. 15/441,654 dated Aug. 28, 2018.
Notice of Allowance from U.S. Appl. No. 15/441,654 dated Jan. 9, 2019.

* cited by examiner

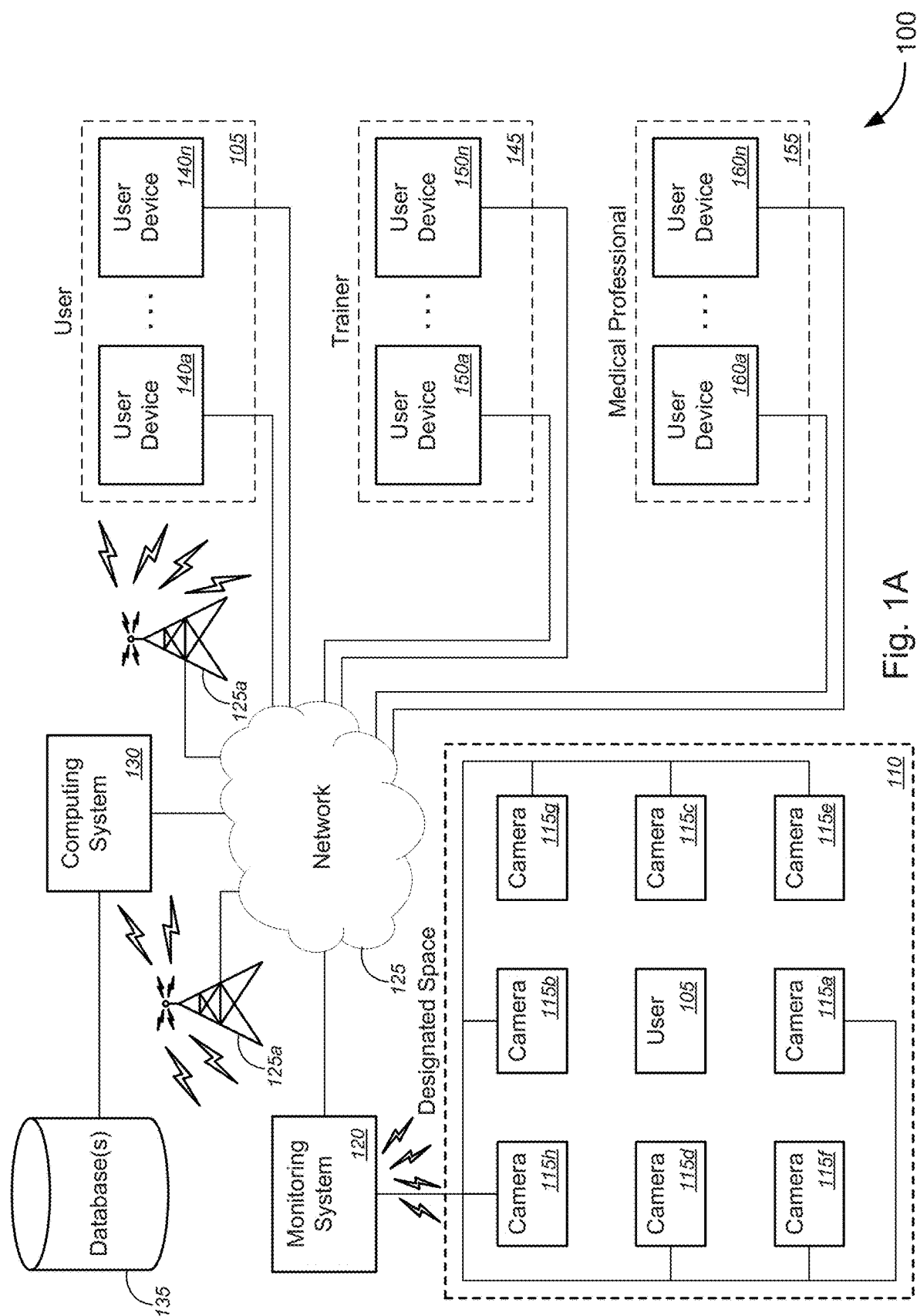

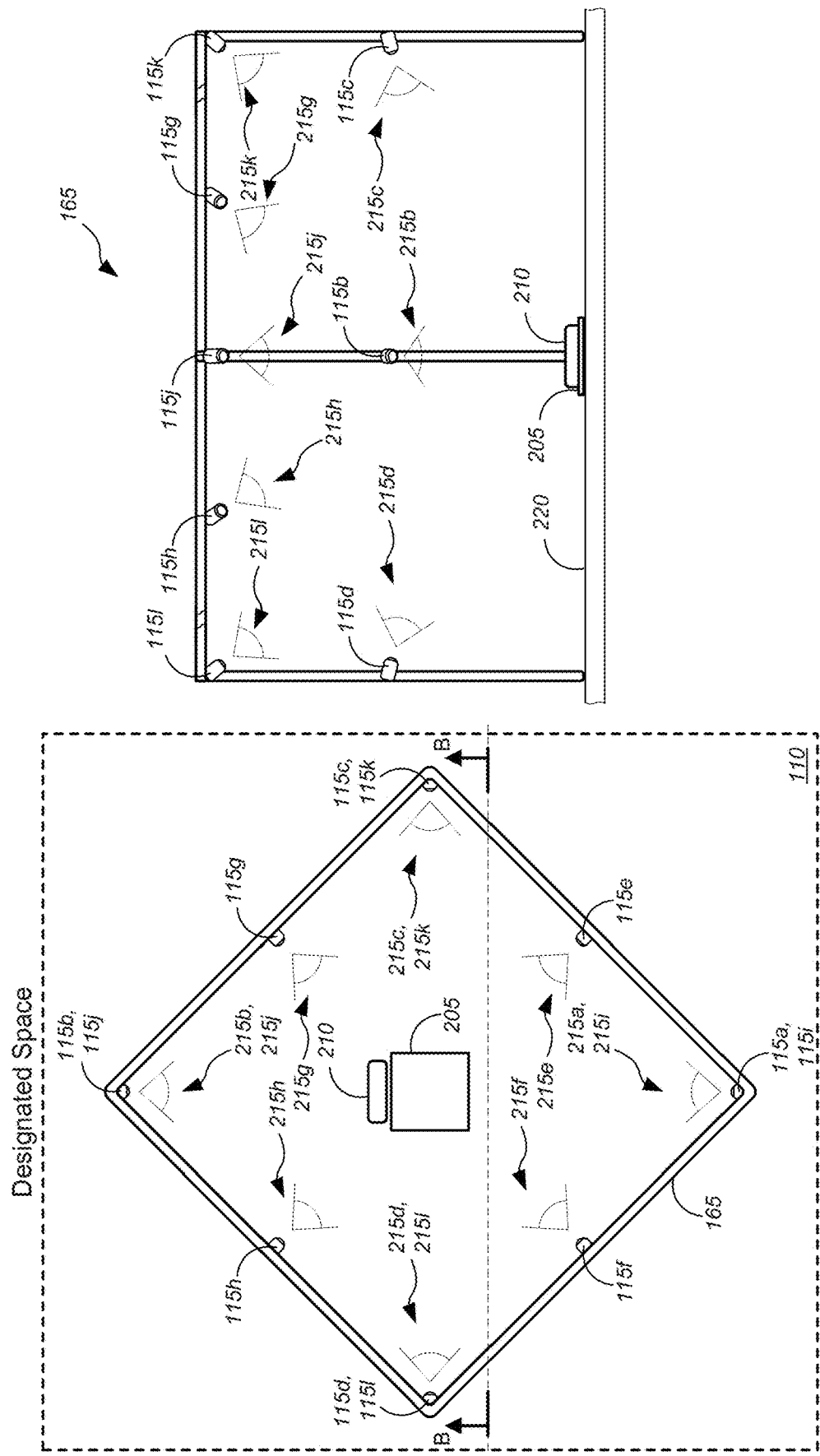

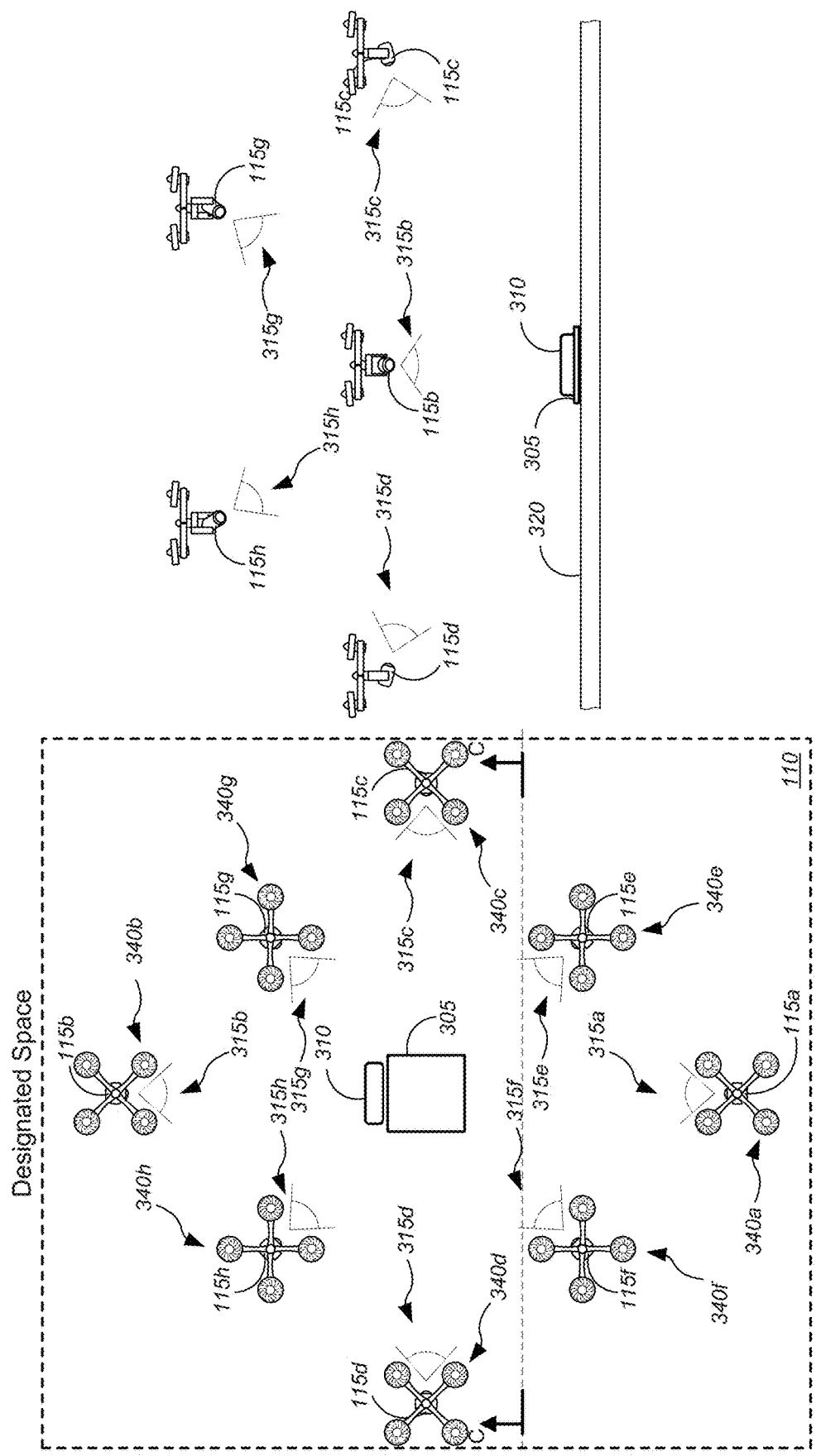

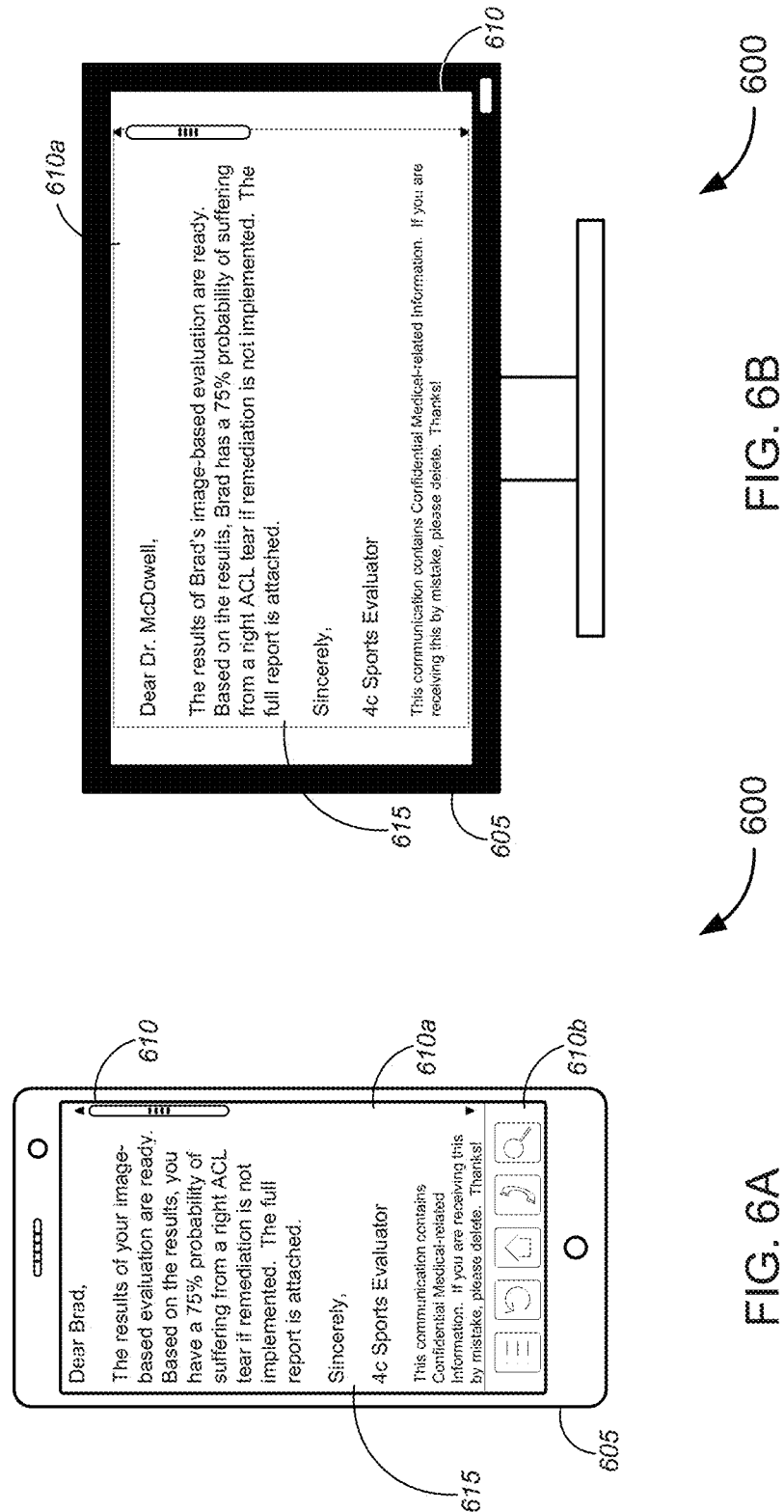

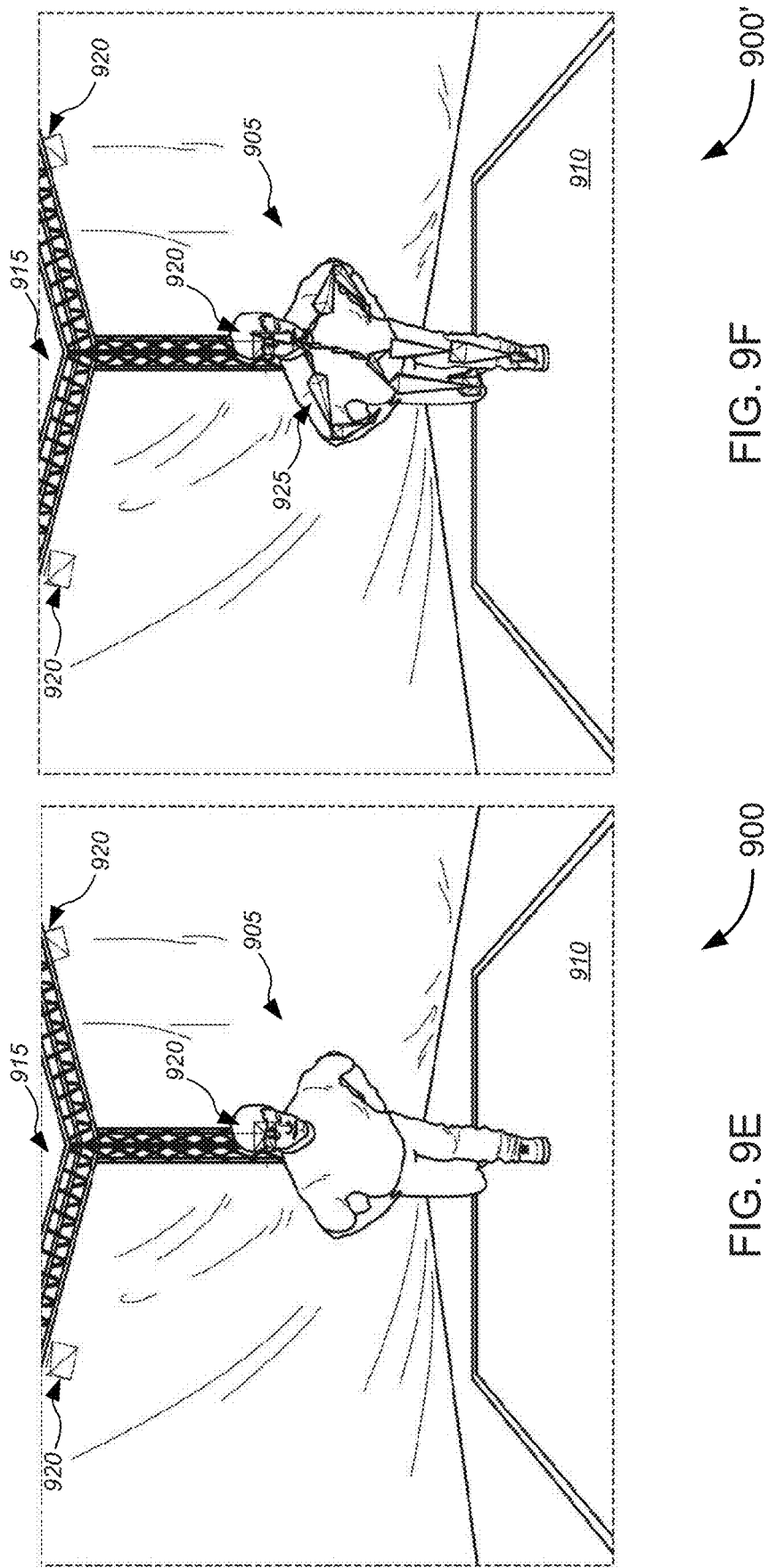

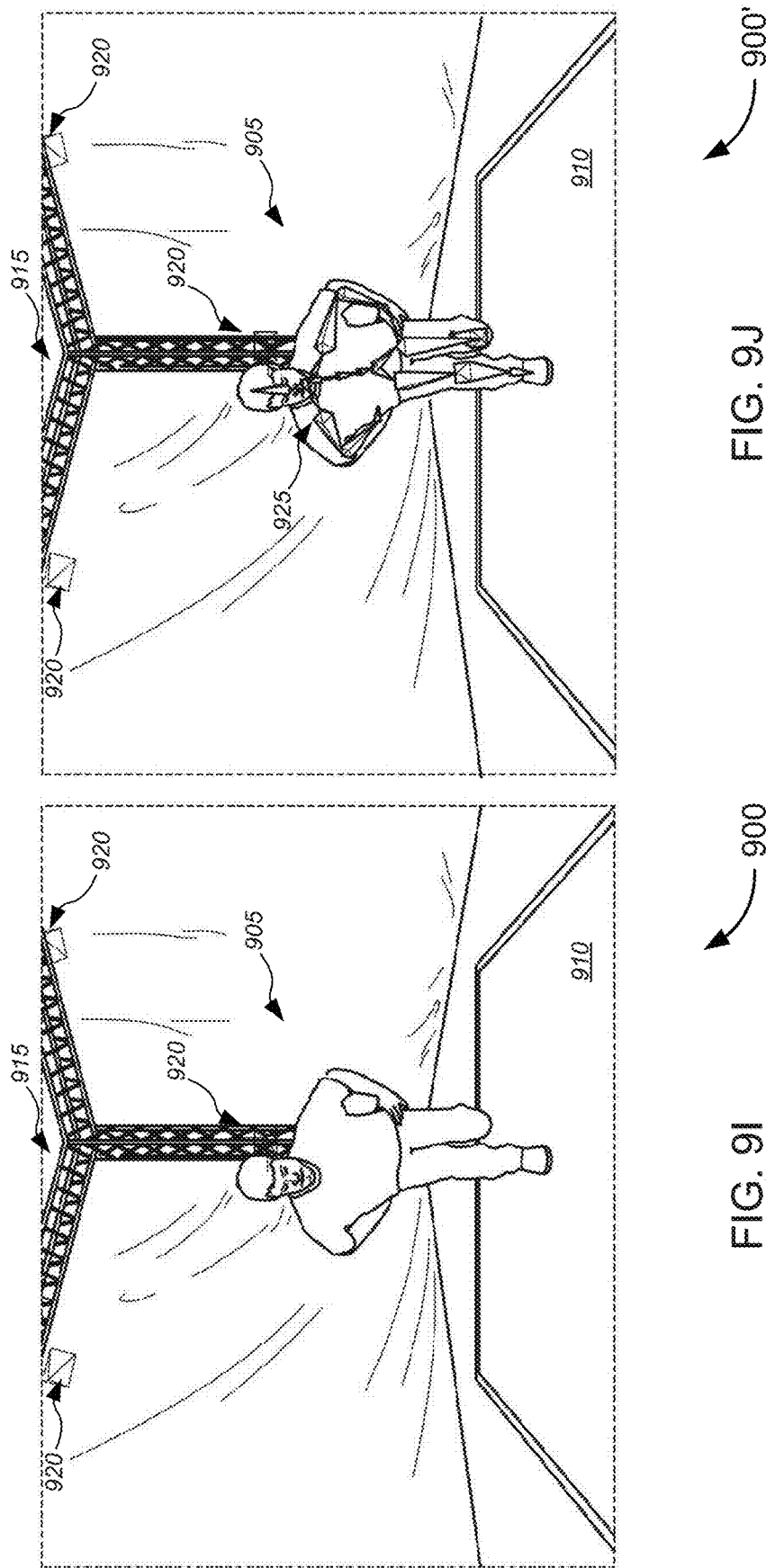

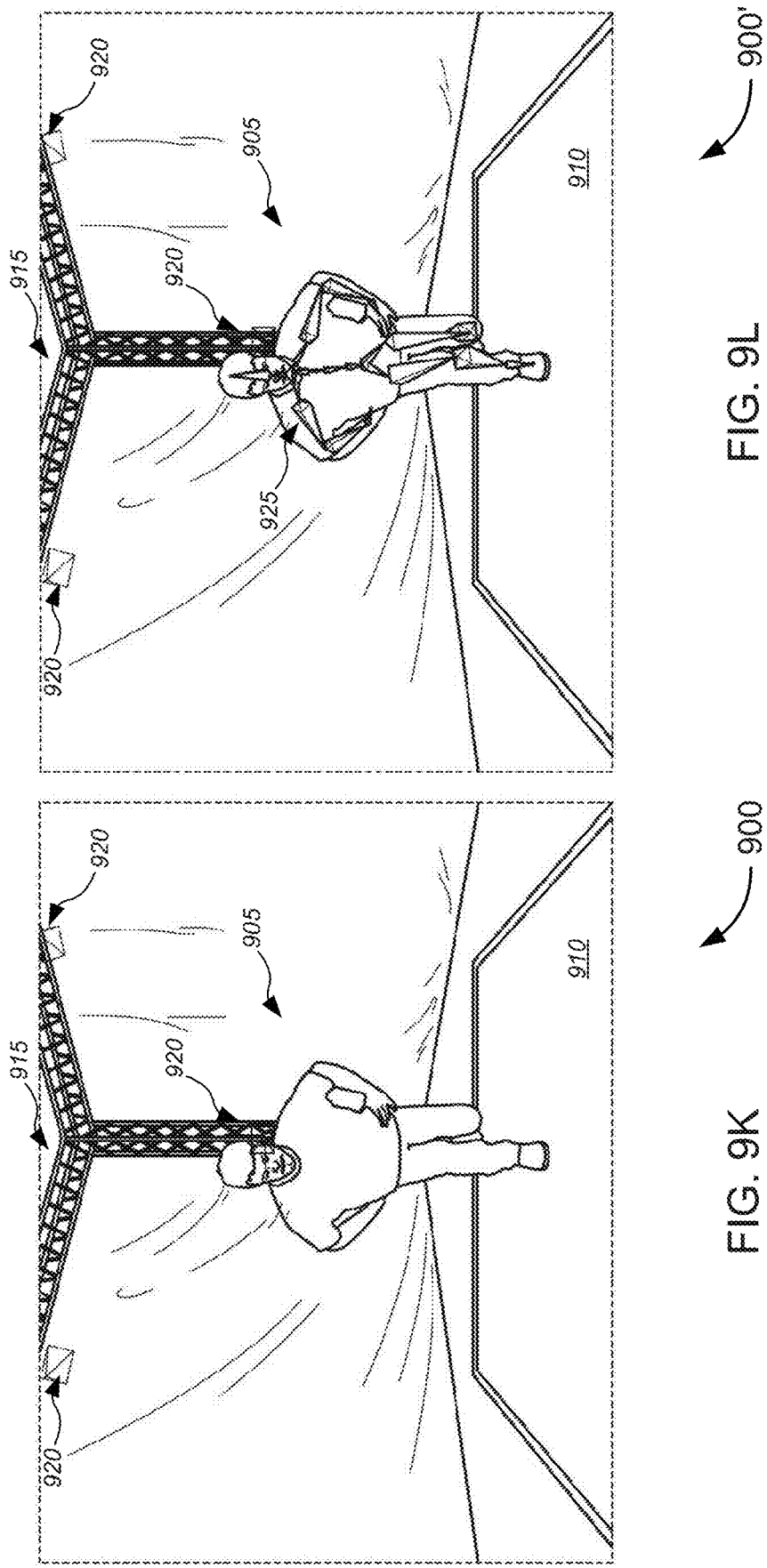

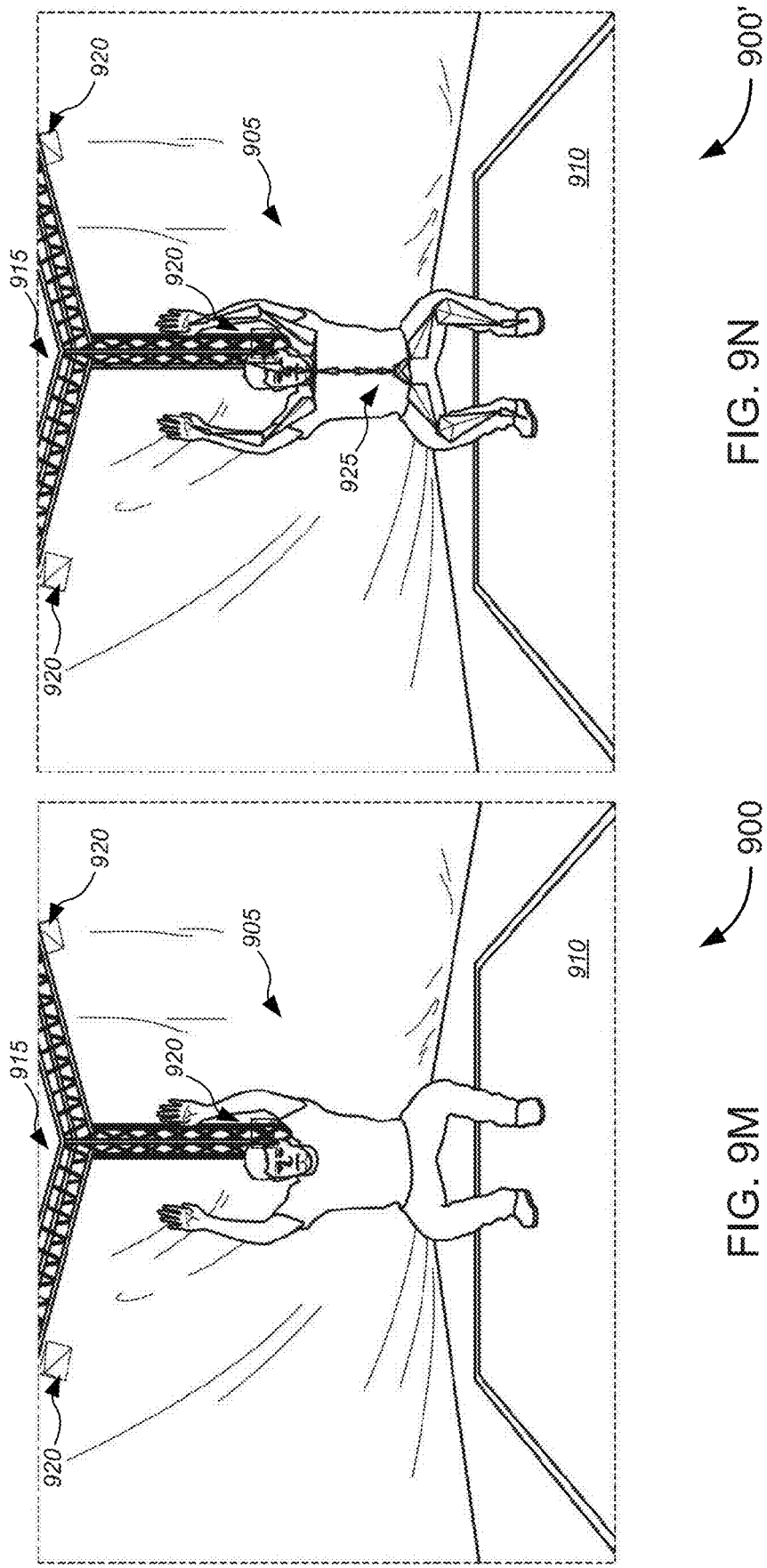

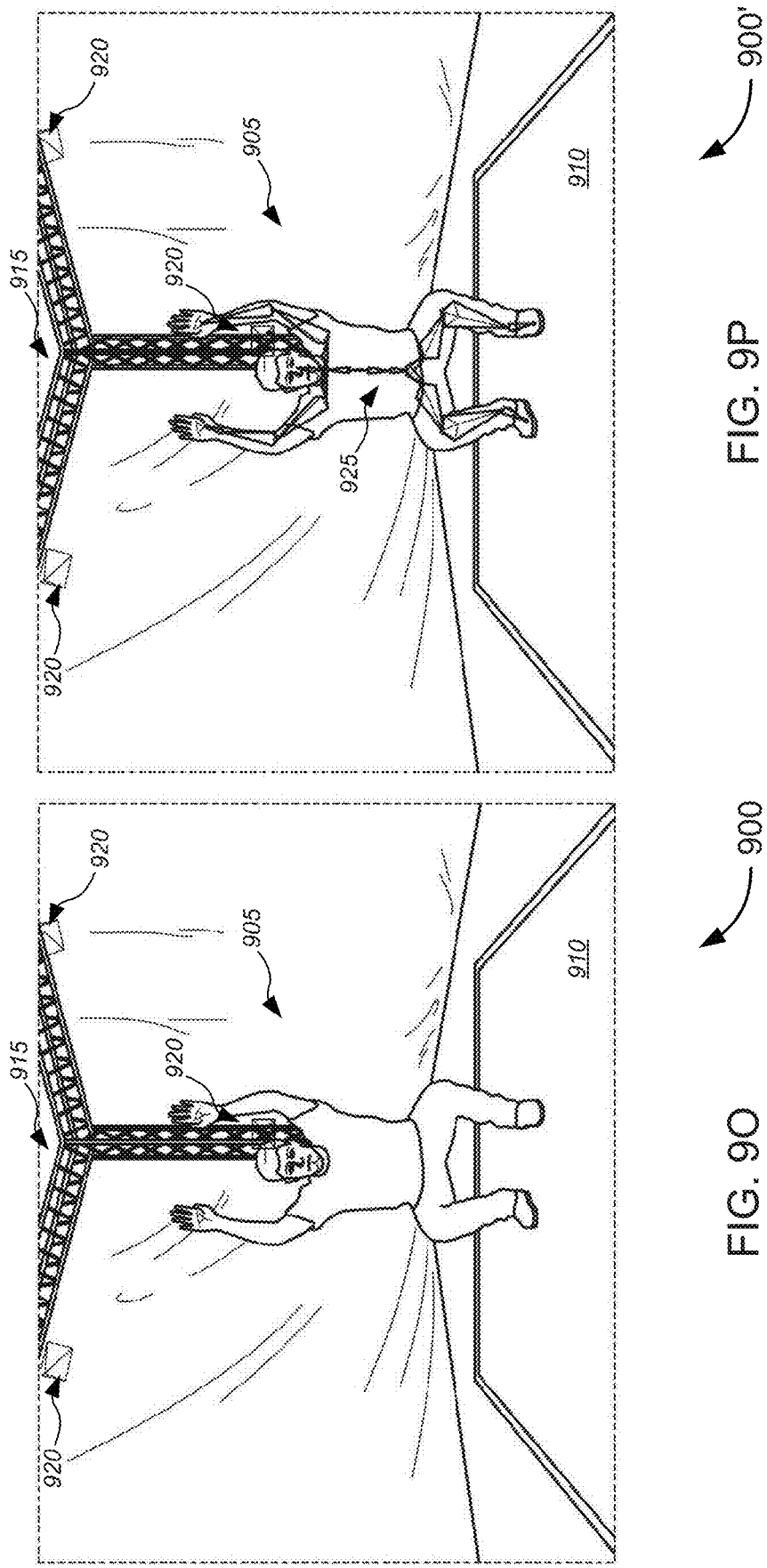

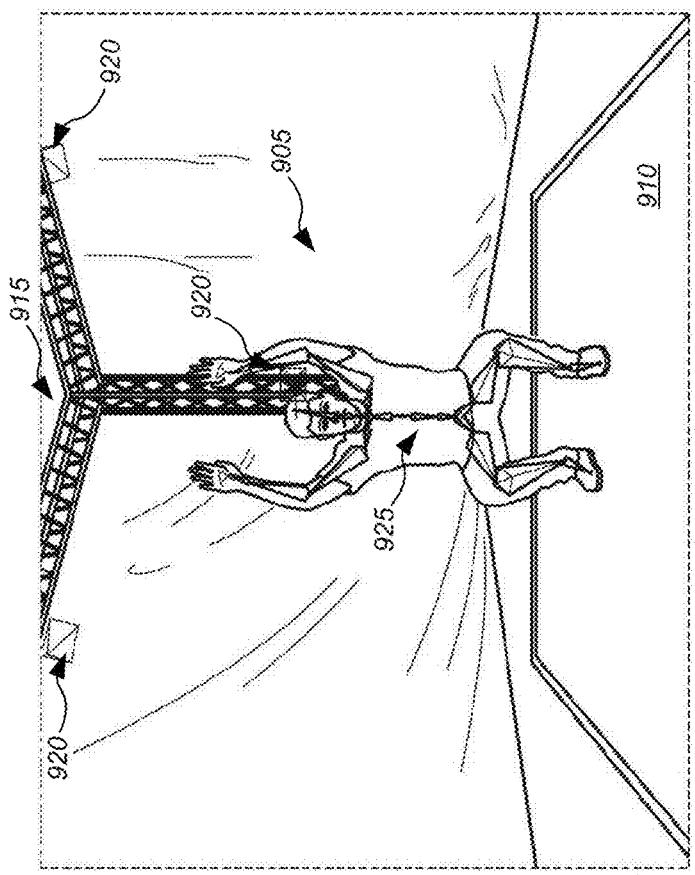
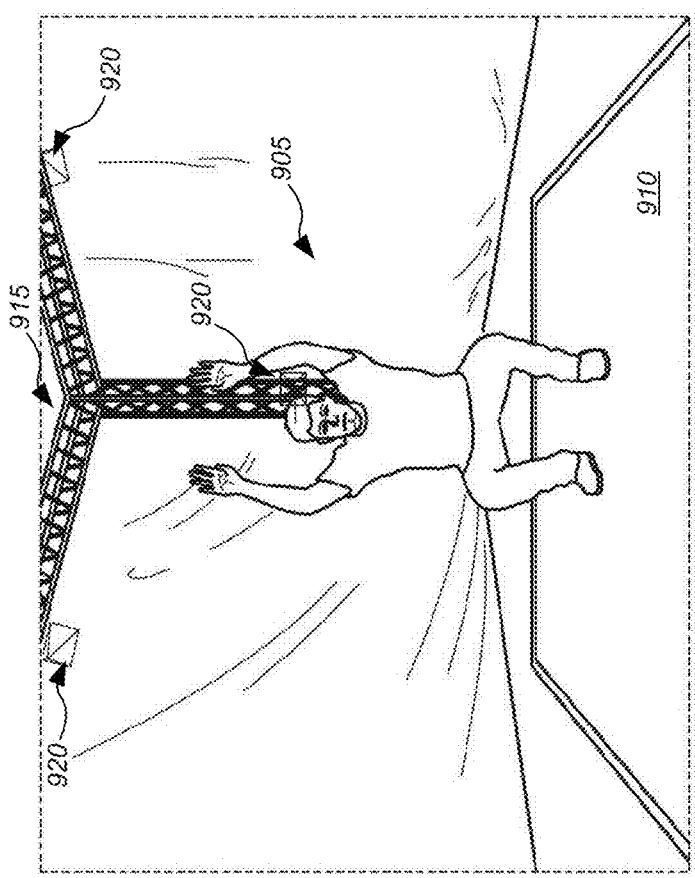
FIG. 9R
FIG. 9Q

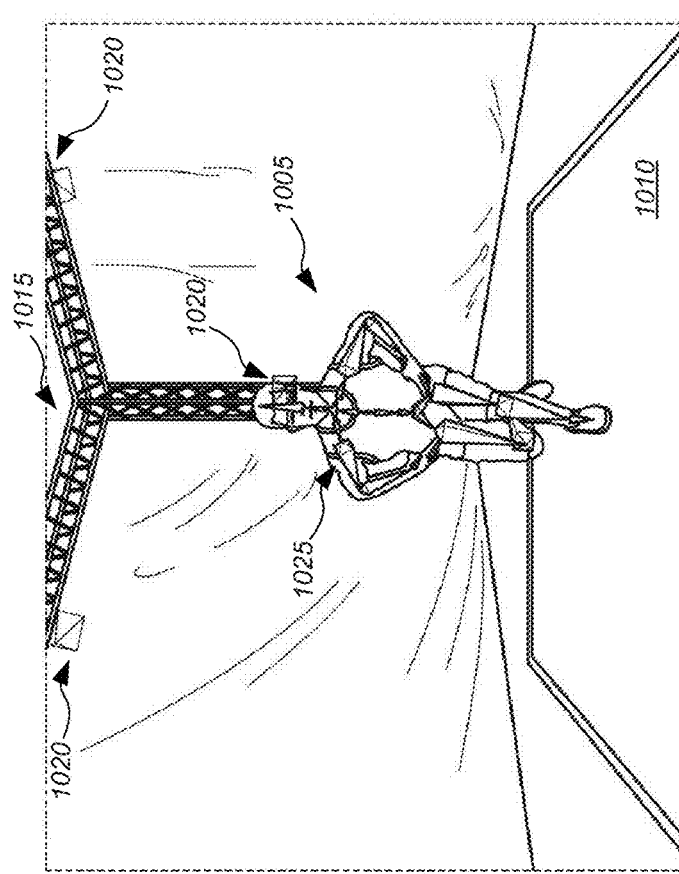
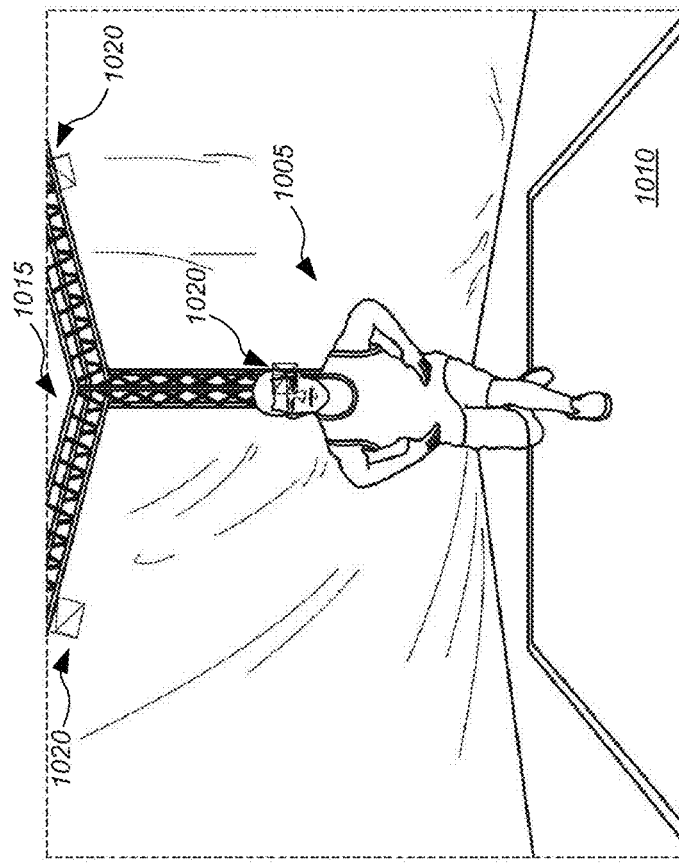

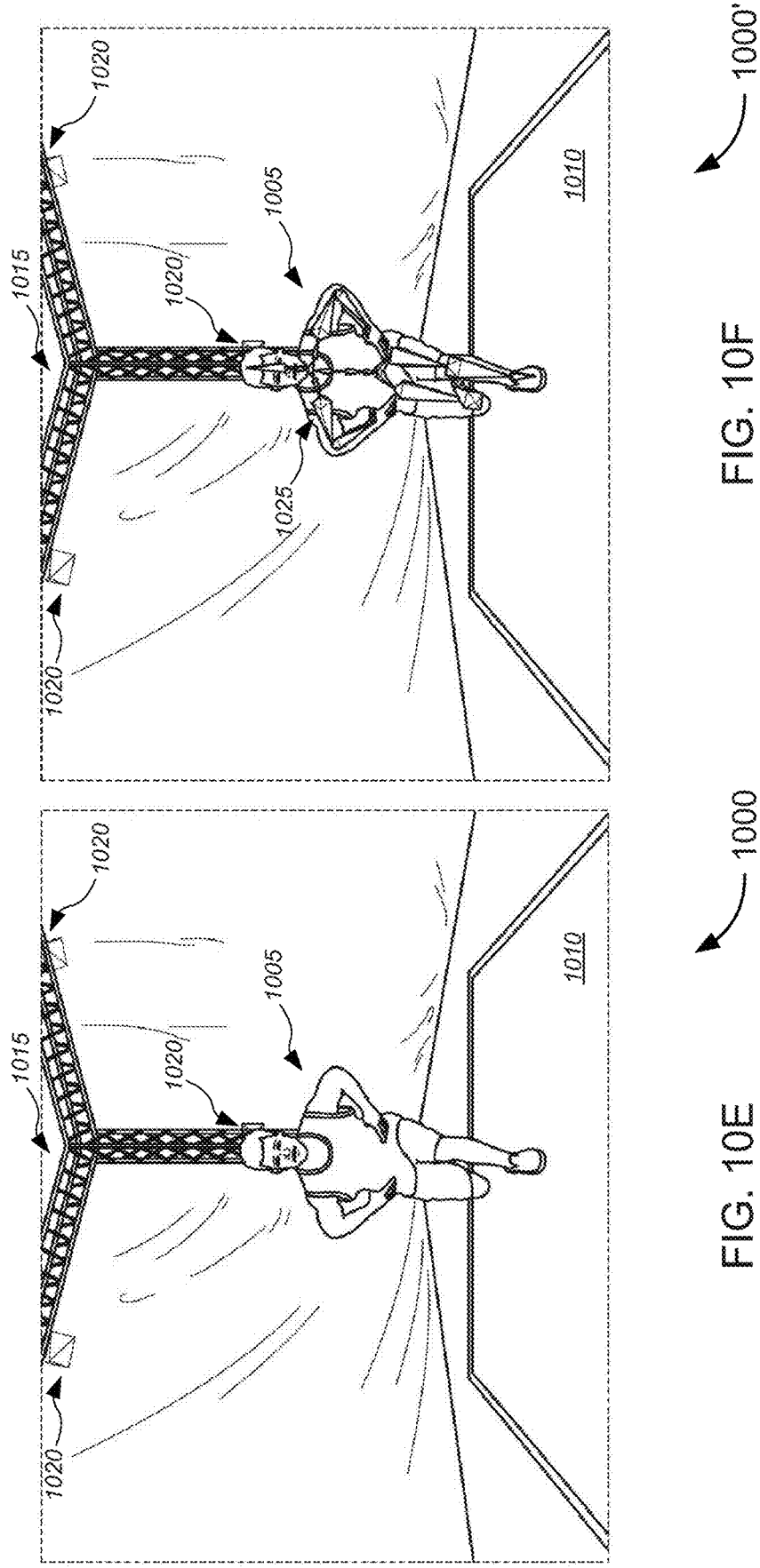

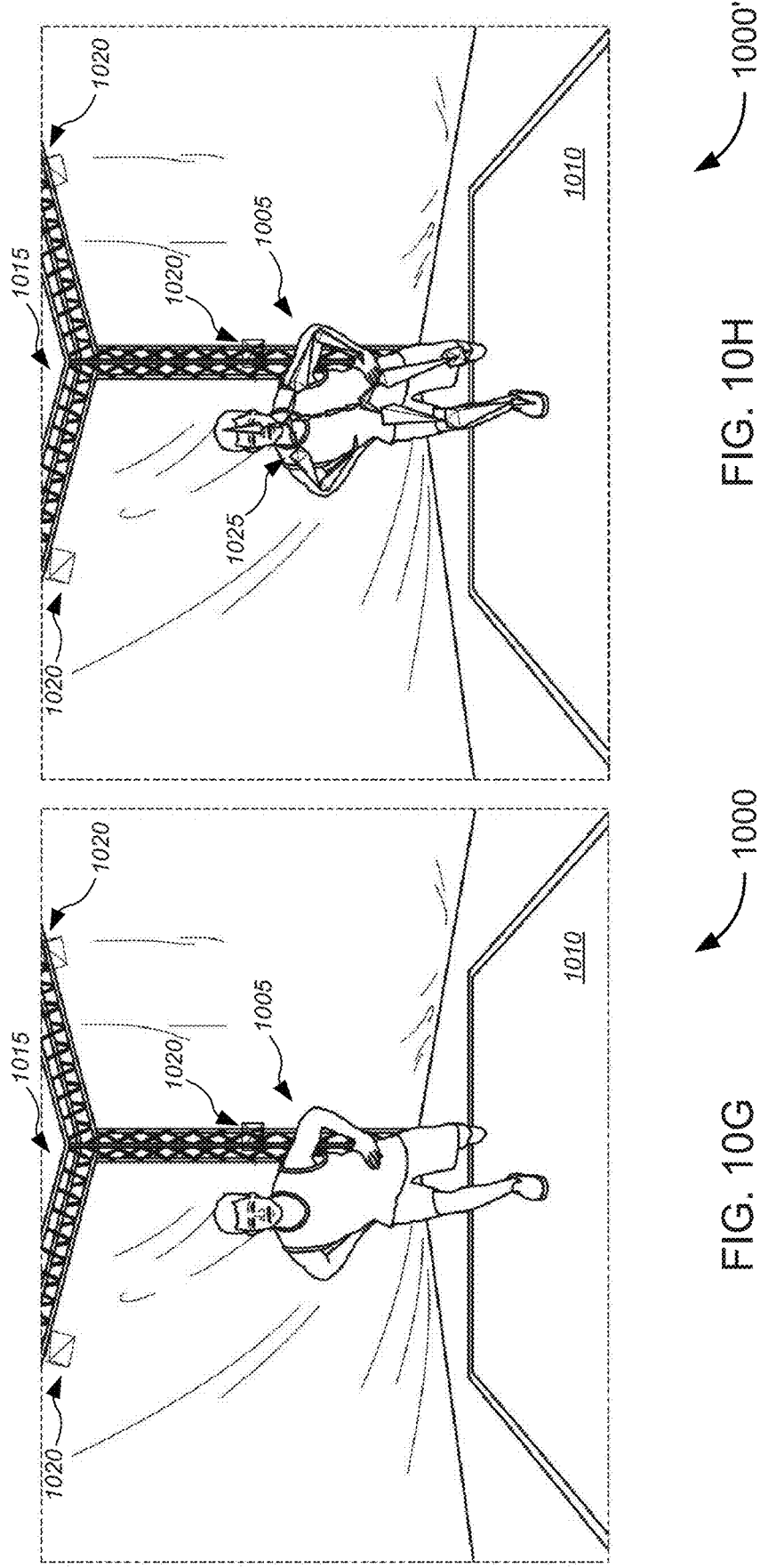

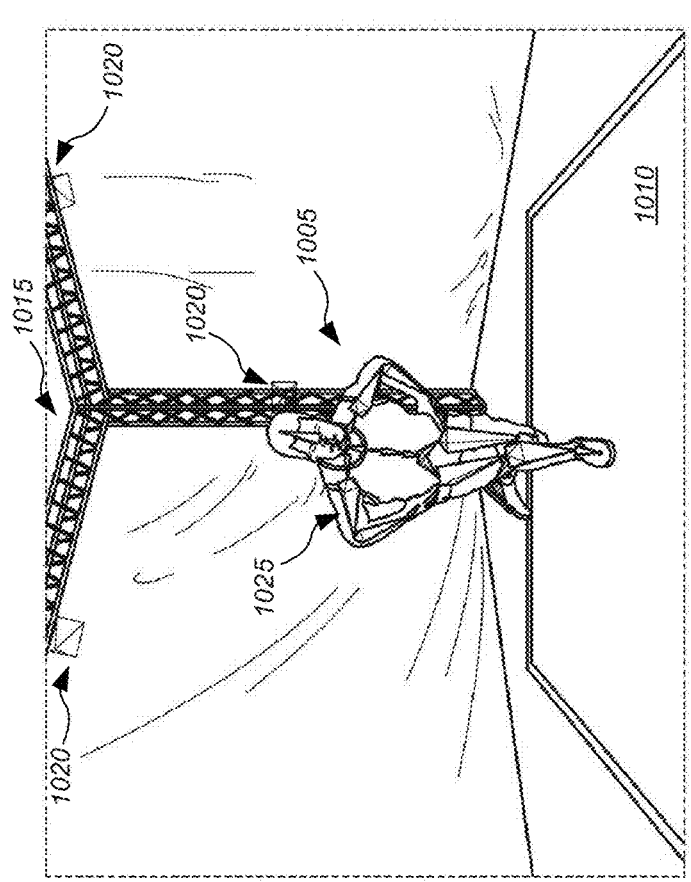
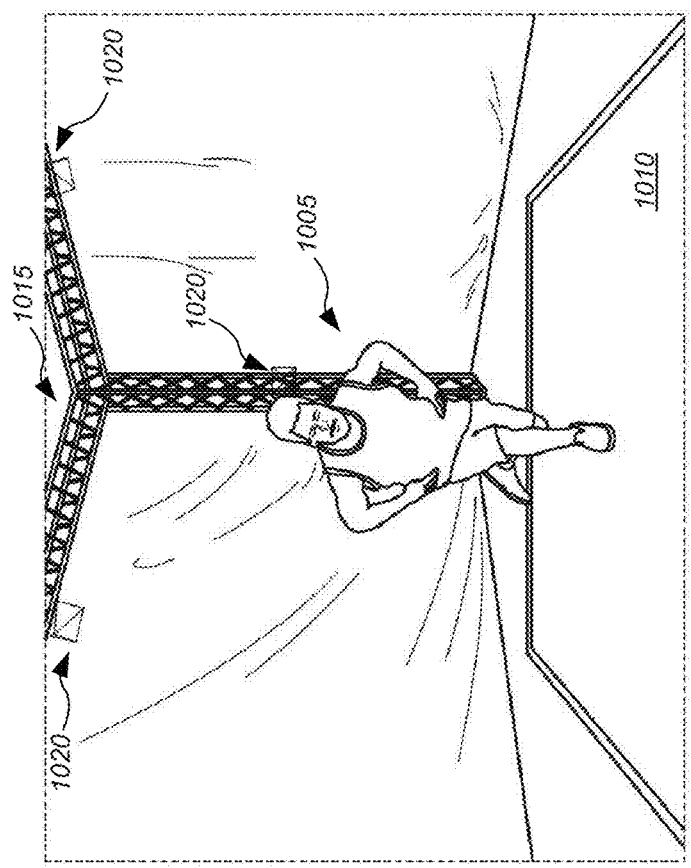
FIG. 10L
FIG. 10K

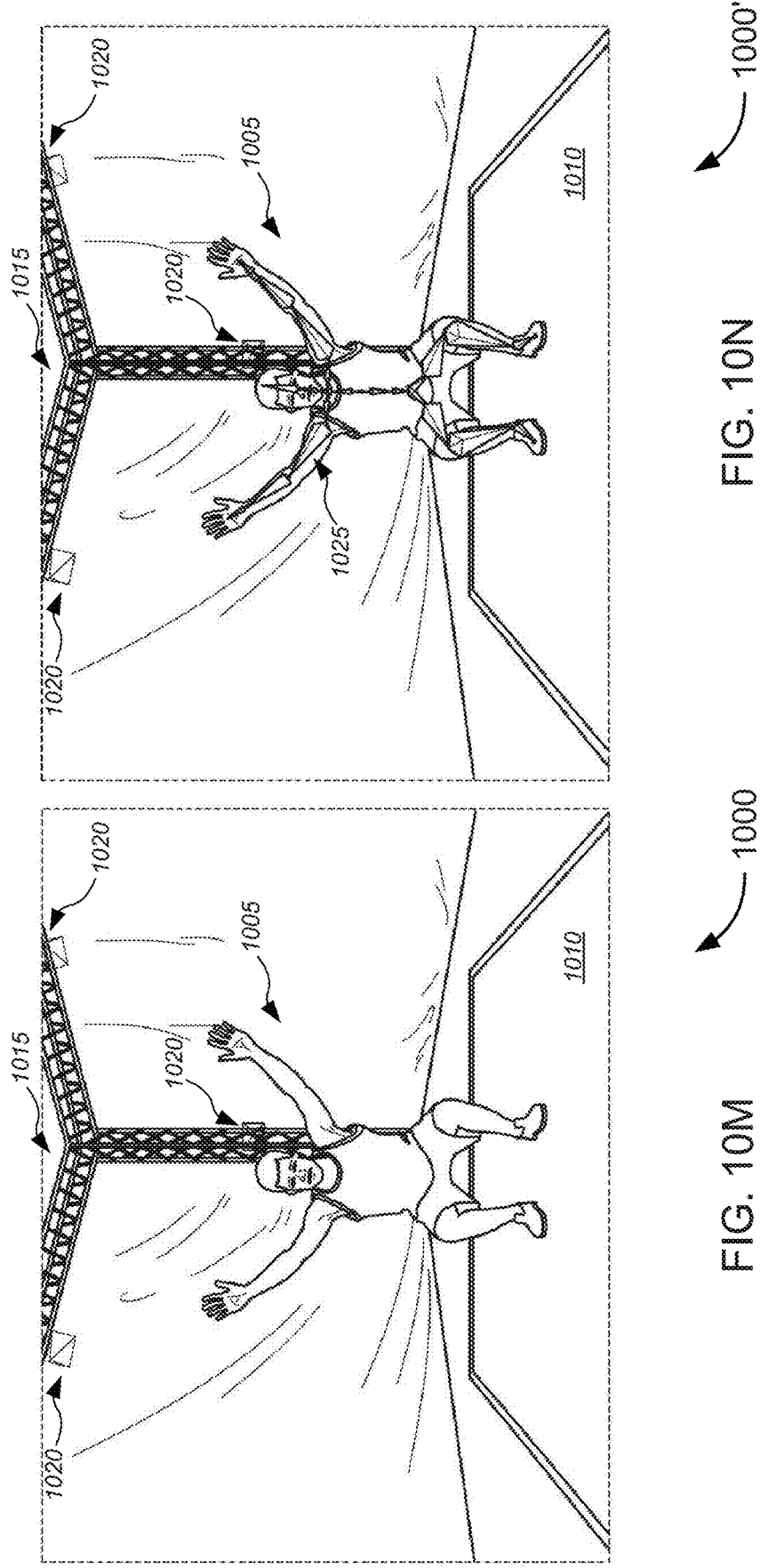

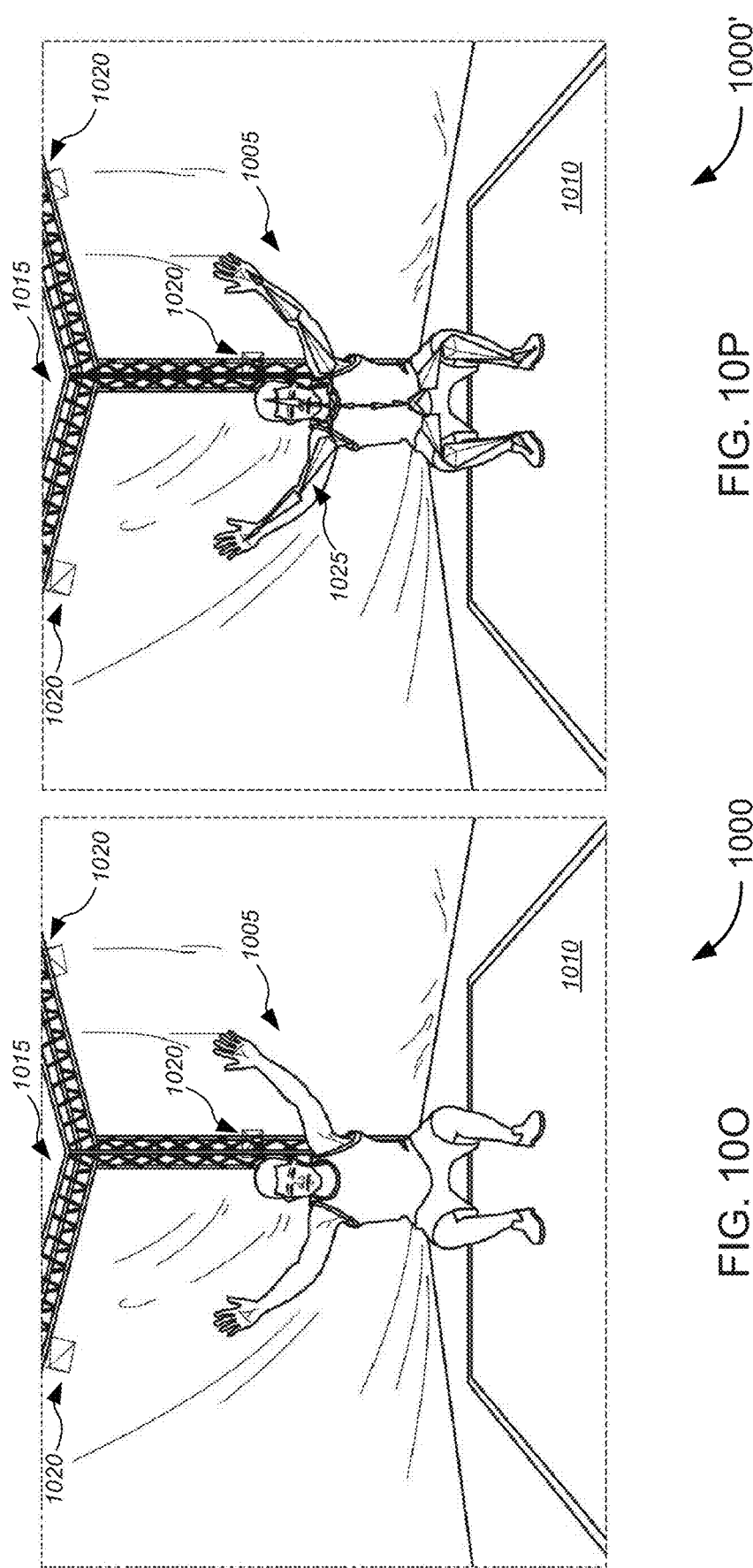

METHOD AND SYSTEM FOR DETERMINING PHYSIOLOGICAL STATUS OF USERS BASED ON MARKER-LESS MOTION CAPTURE AND GENERATING APPROPRIATE REMEDIATION PLANS

CROSS-REFERENCES TO RELATED APPLICATIONS

This application is a continuation of U.S. patent application Ser. No. 15/441,654 (the "'654 application), filed Feb. 24, 2017 by Bradley Richard Hall et al., entitled, "Method and System for Determining Physiological Status of Users Based on Marker-Less Motion Capture and Generating Appropriate Remediation Plans," which claims priority to U.S. Patent Application Ser. No. 62/299,099 (the "'099 application"), filed Feb. 24, 2016 by Bradley Richard Hall et al., entitled, "Method and System for Determining Physiological Status of User Based on Marker-Less Motion Capture," the disclosures of which are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, and computer software for implementing image-based physiological status determination of users, and, in particular embodiments, to methods, systems, and computer software for implementing physiological status determination of users based on marker-less motion-capture and generating remediation plans as appropriate.

BACKGROUND

In sports, injuries are unavoidable at times, sometimes due to bad habits by the individual user or athlete that lead to stresses on parts of the body during repetitive or common motions in the sport, and/or due to genetic factors or the like. It is difficult to diagnose potential for such injuries in order to avoid these injuries, and particularly not with existing image-based diagnostic systems.

Hence, there is a need for more robust and scalable solutions for implementing image-based physiological status determination of users, and, in particular embodiments, for implementing physiological status determination of users based on marker-less motion-capture and generating remediation plans as appropriate.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 1A-1C are schematic diagrams illustrating various embodiments of a system for implementing image-based physiological status or physical condition determination of users and generating remediation plans as appropriate.

FIGS. 2A-2E are schematic diagrams illustrating various enclosure-based systems for implementing image-based physiological status or physical condition determination of users and generating remediation plans as appropriate, in accordance with various embodiments.

FIGS. 3A and 3B are schematic diagrams illustrating a drone-based system for implementing image-based physiological status or physical condition determination of users and generating remediation plans as appropriate, in accordance with various embodiments.

FIGS. 6A-6D illustrate example user interfaces and notifications that a user, a trainer of the user, or the user's physician or other medical professional might interact with or receive, in accordance with various embodiments.

DETAILED DESCRIPTION OF CERTAIN EMBODIMENTS

Overview

Figure 1B:
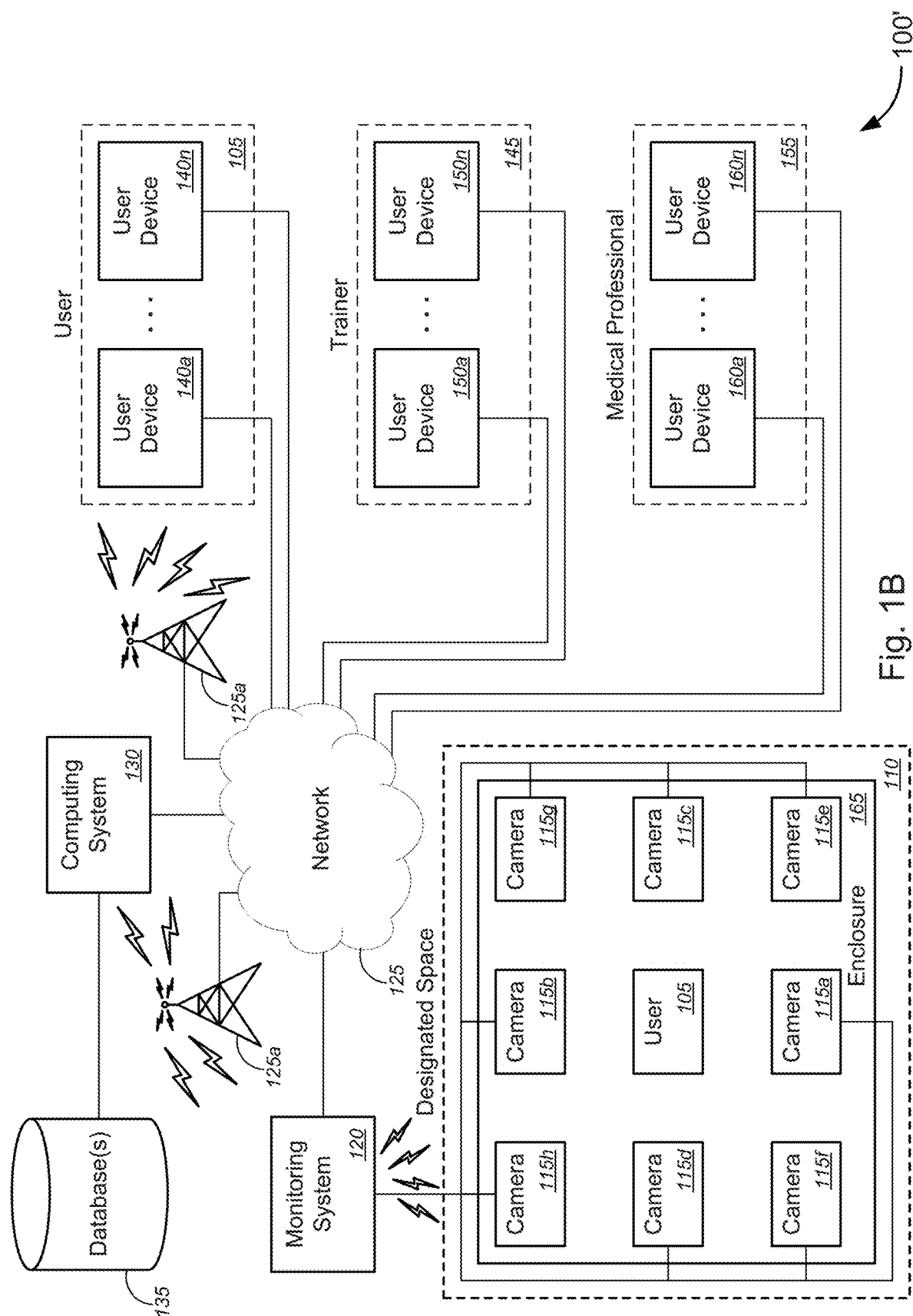

Various embodiments provide tools and techniques for implementing image-based physiological status determination of users, and, in particular embodiments, for implementing physiological status determination of users based on marker-less motion-capture and generating remediation plans as appropriate.

In various embodiments, one or more cameras may be used to capture views of a user (e.g., an athlete, a person trying to live a healthy life, or the like) as the user is performing one or more set of motions, and the captured images may be overlaid with a skeletal framework that is compared with similar skeletal framework overlaid images for the same one or more sets of motions. The system can automatically determine a physical condition of the user or a probability that the user will suffer a physical condition based at least in part on an analysis of the comparison. In most cases, the human eye is unable to detect the very minute deviation in the relative positions of the body parts (in some cases, represented by the skeletal framework), whereas the computing system can distinguish such minute deviations in its comparisons with not only baseline captured images (and in some cases, with the skeletal framework overlay) of the same user at an earlier time, but also comparisons with captured images (and in some cases, with the skeletal framework overlay) of each of a plurality of users (some having been diagnosed as not having a particular injury or injury risk, while others having been diagnosed with particular injuries or injury risks, etc.).

The Appendix in the '099 application (which has already been incorporated herein by reference in its entirety) describes some additional embodiments of the system and method for implementing image-based physiological status determination of users, and, in particular embodiments, for implementing physiological status determination of users based on marker-less motion-capture and generating remediation plans as appropriate.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

Various embodiments described herein, while embodying (in some cases) software products, computer-performed methods, and/or computer systems, represent tangible, concrete improvements to existing technological areas, including, without limitation, medical diagnostic technology, image-based medical diagnostic technology, injury prediction technology, image-based injury prediction technology, and/or the like. To the extent any abstract concepts are present in the various embodiments, those concepts can be implemented as described herein by devices, software, systems, and methods that involve specific novel functionality (e.g., steps or operations), such as utilizing a plurality of views of a user (e.g., athlete, patient, health-conscious person, etc.) captured by a plurality of cameras and using an automated process to analyze the plurality of views (in some cases by comparing with similar views of a plurality of users) to determine likelihood of a physical condition or likelihood the user will suffer the physical condition, and sending notifications to the user regarding the results of the analysis, and/or the like, to name a few examples, that extend beyond mere conventional computer processing operations. These functionalities can produce tangible results outside of the implementing computer system, including, merely by way of example, ability to improve image-based diagnosis of the user, and/or the like, in various embodiments, which may be observed or measured by others. Further, without the computer-based analysis, it would be impossible for a single doctor or trained medical professional (or a group of trained medical professionals), even if extremely trained, to visually diagnose the physical conditions with the same or similar results, with the level of precision and accuracy achievable by the techniques and systems described herein.

In an aspect, a method might comprise capturing, with one or more cameras, one or more views of a user within a designated space, as the user is performing one or more sets of motions, receiving, with a computing system, the captured one or more views of the user for each of the one or more sets of motions, and determining, with the computing system, dynamic relationships among two or more body parts of the user for each of the one or more sets of motions, based at least in part on an analysis of the captured one or more views of the user for each of the one or more sets of motions. The method might also comprise comparing, with the computing system, the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database. The method might further comprise determining, with the computing system, a physiological status of the user based at least in part on the comparison of the dynamic relationships among the two or more body parts of the user with dynamic relationships among corresponding two or more body parts of each of a plurality of users for each of the one or more sets of motions.

In some embodiments, capturing one or more views of a user within a designated space, as the user is performing one or more sets of motions might comprise capturing, with one or more cameras, one or more views of a user within a designated space, as the user is performing one or more sets of motions using marker-less motion capture. According to some embodiments, the one or more cameras might comprise an array of cameras around the user within the designated space, and the one or more views of the user might comprise one or more perspective or elevation views of the user within the designated space. In some cases, the array of cameras might comprise an eight-camera array of cameras, while in other cases, the array of cameras might comprise a twelve-camera array of cameras. Of course, a person skilled in the art can appreciate that any suitable number of cameras (from one camera to more than twelve cameras) may be employed in the array of cameras, so long as all pertinent views of the user are captured to enable analysis or determination of the dynamic relationships among the two or more body parts of the user for each of the one or more sets of motions.

In some cases, the one or more cameras might comprise at least one of one or more stationary cameras, one or more cameras mounted on mechanical arms, one or more aerial drone-based cameras, or one or more ground-type drone-based cameras, and the like. In some instances, the designated space might be one of an indoor space, a man-made portable enclosure, and/or an outdoor space, or the like. In some embodiments (particularly in outdoor settings, although also applicable to indoor settings or portable enclosure settings, or the like), the method might further comprise filtering, with the computing system, lighting-related artifacts in each of the captured one or more views of the user for each of the one or more sets of motions, prior to determining dynamic relationships among the two or more body parts of the user for each of the one or more sets of motions. According to some embodiments, the designated space might be one of a sports stadium, an athletic field, an ice rink, a ski slope, a trail, a roadway, or a pathway, and/or the like.

In some instances, the computing system might be located proximal to the designated space. Alternatively, the computing system might be located at a remote location relative to the designated space, and receiving the captured one or more views of the user for each of the one or more sets of motions might comprise receiving, with a computing system, the captured one or more views of the user for each of the one or more sets of motions via a network.

In some embodiments, determining dynamic relationships among two or more body parts of the user for each of the one or more sets of motions might comprise overlaying, with the computing system, a virtual skeletal framework over at least portions of a body of the user in the captured one or more views of the user for each of the one or more sets of motions; mapping, with the computing system, relative positions of the two or more body parts based on the overlaid virtual skeletal framework, for each of the one or more sets of motions; and determining, with the computing system, dynamic relationships among two or more body parts of the user for each of the one or more sets of motions, based at least in part on the mapped relative positions of the two or more body parts. In such cases, comparing the dynamic relationships among the two or more body parts of the user with dynamic relationships among corresponding two or more body parts of each of a plurality of users for each of the one or more sets of motions might comprise comparing, with the computing system, the dynamic relationships among the two or more body parts of the user with dynamic relationships among corresponding two or more body parts of each of a plurality of users for each of the one or more sets of motions by comparing the mapped relative positions of the two or more body parts of the user with corresponding mapped relative positions of each of the plurality of users for each of the one or more sets of motions.

Merely by way of example, in some cases, the two or more body parts of the user might comprise at least two of one or more toes, at least one ankle, at least one knee, at least one hip, at least one shoulder, at least one elbow, at least one wrist, one or more fingers, a neck, or a skull of the user, and/or the like. In some instances, the physiological status of user might be a physiological status (or a physical condition) selected from a group consisting of a concussion, a torn anterior cruciate ligament ("ACL"), a torn posterior cruciate ligament ("PCL"), a torn medial collateral ligament ("MCL"), a torn lateral collateral ligament ("LCL"), an ankle sprain, a groin pull, a hamstring strain, shin splints, and tennis elbow, and/or the like.

According to some embodiments, determining a physiological status of the user might comprise determining, with the computing system, a probability of a physiological status of the user based at least in part on the comparison of the dynamic relationships among the two or more body parts of the user with dynamic relationships among corresponding two or more body parts of each of a plurality of users for each of the one or more sets of motions.

In some embodiments, the method might further comprise sending, with the computing system and to one or more user devices, a notification indicating the physiological status of the user. In some instances, sending a notification indicating the physiological status of the user might comprise sending, with the computing system and to one or more user devices, a notification indicating the physiological status of the user via a software application ("app"), for display in a graphical user interface of the software app. Alternatively, or additionally, sending a notification indicating the physiological status of the user might comprise sending, with the computing system and to one or more user devices, at least one of a text message, a short message service ("SMS") message, a multimedia messaging service ("MMS") message, an e-mail message, or a chat message, each such message comprising the notification indicating the physiological status of the user. In some cases, the one or more user devices might comprise at least one of a smartphone, a mobile phone, a personal digital assistant, a tablet computer, a laptop computer, a desktop computer, or a server computer, and/or the like.

Merely by way of example, according to some embodiments, the method might further comprise sending, with the computing system and to one or more user devices, a remediation plan to prevent occurrence of the physiological status of the user. The method, in some embodiments, might further comprise storing, with the computing system and in the database, the dynamic relationships among the two or more body parts of the user together with the dynamic relationships among corresponding two or more body parts of the plurality of users for each of the one or more sets of motions. In some cases, retrieving or storing the dynamic relationships among the two or more body parts of each of the user and the plurality of users from or in the database might be performed over a network.

In another aspect, an image-based physiological diagnostic system might be provided. The image-based physiological diagnostic system might comprise one or more cameras that capture one or more views of a user within a designated space, as the user is performing one or more sets of motions. The image-based physiological diagnostic system might further comprise a computing system that comprises at least one processor and at least one non-transitory computer readable medium communicatively coupled to the at least one processor. The at least one non-transitory computer readable medium might have stored thereon computer software comprising a set of instructions that, when executed by the at least one processor, causes the computing system to: receive, from the one or more cameras, the captured one or more views of the user for each of the one or more sets of motions; determine dynamic relationships among two or more body parts of the user for each of the one or more sets of motions, based at least in part on an analysis of the captured one or more views of the user for each of the one or more sets of motions; compare the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database; and determine a physiological status of the user based at least in part on the comparison of the dynamic relationships among the two or more body parts of the user with dynamic relationships among corresponding two or more body parts of each of a plurality of users for each of the one or more sets of motions.

In some embodiments, the one or more cameras capture the one or more views of a user using marker-less motion capture. According to some embodiments, the one or more cameras might comprise an array of cameras around the user within the designated space, and the one or more views of the user might comprise one or more perspective or elevation views of the user within the designated space. In some cases, the array of cameras might comprise an eight-camera array of cameras, while in other cases, the array of cameras might comprise a twelve-camera array of cameras. Of course, a person skilled in the art can appreciate that any suitable number of cameras (from one camera to more than twelve cameras) may be employed in the array of cameras, so long as all pertinent views of the user are captured to enable analysis or determination of the dynamic relationships among the two or more body parts of the user for each of the one or more sets of motions.

In some instances, the designated space might be one of an indoor space, a man-made portable enclosure, and/or an outdoor space, or the like. In some embodiments (particularly in outdoor settings, although also applicable to indoor settings or portable enclosure settings, or the like), the set of instructions, when executed by the at least one processor, further causes the computing system to filter lighting-related artifacts in each of the captured one or more views of the user for each of the one or more sets of motions, prior to determining dynamic relationships among the two or more body parts of the user for each of the one or more sets of motions. According to some embodiments, the designated space might be one of a sports stadium, an athletic field, an ice rink, a ski slope, a trail, a roadway, or a pathway, and/or the like.

In yet another aspect, a computer system might be provided. The computer system might comprise at least one processor and at least one non-transitory computer readable medium communicatively coupled to the at least one processor. The at least one non-transitory computer readable medium might have stored thereon computer software comprising a set of instructions that, when executed by the at least one processor, causes the computing system to: receive captured one or more views of the user within a designated space, as the user is performing one or more sets of motions; determine dynamic relationships among two or more body parts of the user for each of the one or more sets of motions, based at least in part on an analysis of the captured one or more views of the user for each of the one or more sets of motions; compare the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database; and determine a physiological status of the user based at least in part on the comparison of the dynamic relationships among the two or more body parts of the user with dynamic relationships among corresponding two or more body parts of each of a plurality of users for each of the one or more sets of motions.

In still another aspect, a method might comprise receiving, with a computing system, captured one or more views of the user within a designated space, as the user is performing one or more sets of motions and determining, with the computing system, dynamic relationships among two or more body parts of the user for each of the one or more sets of motions, based at least in part on an analysis of the captured one or more views of the user for each of the one or more sets of motions. The method might also comprise comparing, with the computing system, the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database. The method might further comprise determining, with the computing system, a physiological status of the user based at least in part on the comparison of the dynamic relationships among the two or more body parts of the user with dynamic relationships among corresponding two or more body parts of each of a plurality of users for each of the one or more sets of motions.

In another aspect, a method might comprise autonomously diagnosing, with a computing system, a physical condition of a user or a probability that a user will suffer a physical condition based at least in part on analysis of a set of image-captured set of motions by the user or analysis of motion-captured images of a set of motions by the user.

Various modifications and additions can be made to the embodiments discussed without departing from the scope of the invention. For example, while the embodiments described above refer to particular features, the scope of this invention also includes embodiments having different combination of features and embodiments that do not include all of the above described features.

Specific Exemplary Embodiments

We now turn to the embodiments as illustrated by the drawings. FIGS. 1-10S illustrate some of the features of the method, system, and apparatus for implementing image-based physiological status determination of users, and, in particular embodiments, for implementing physiological status determination of users based on marker-less motion-capture and generating remediation plans as appropriate, as referred to above. The methods, systems, and apparatuses illustrated by FIGS. 1-10S refer to examples of different embodiments that include various components and steps, which can be considered alternatives or which can be used in conjunction with one another in the various embodiments. The description of the illustrated methods, systems, and apparatuses shown in FIGS. 1-10S is provided for purposes of illustration and should not be considered to limit the scope of the different embodiments.

Figure 1C:
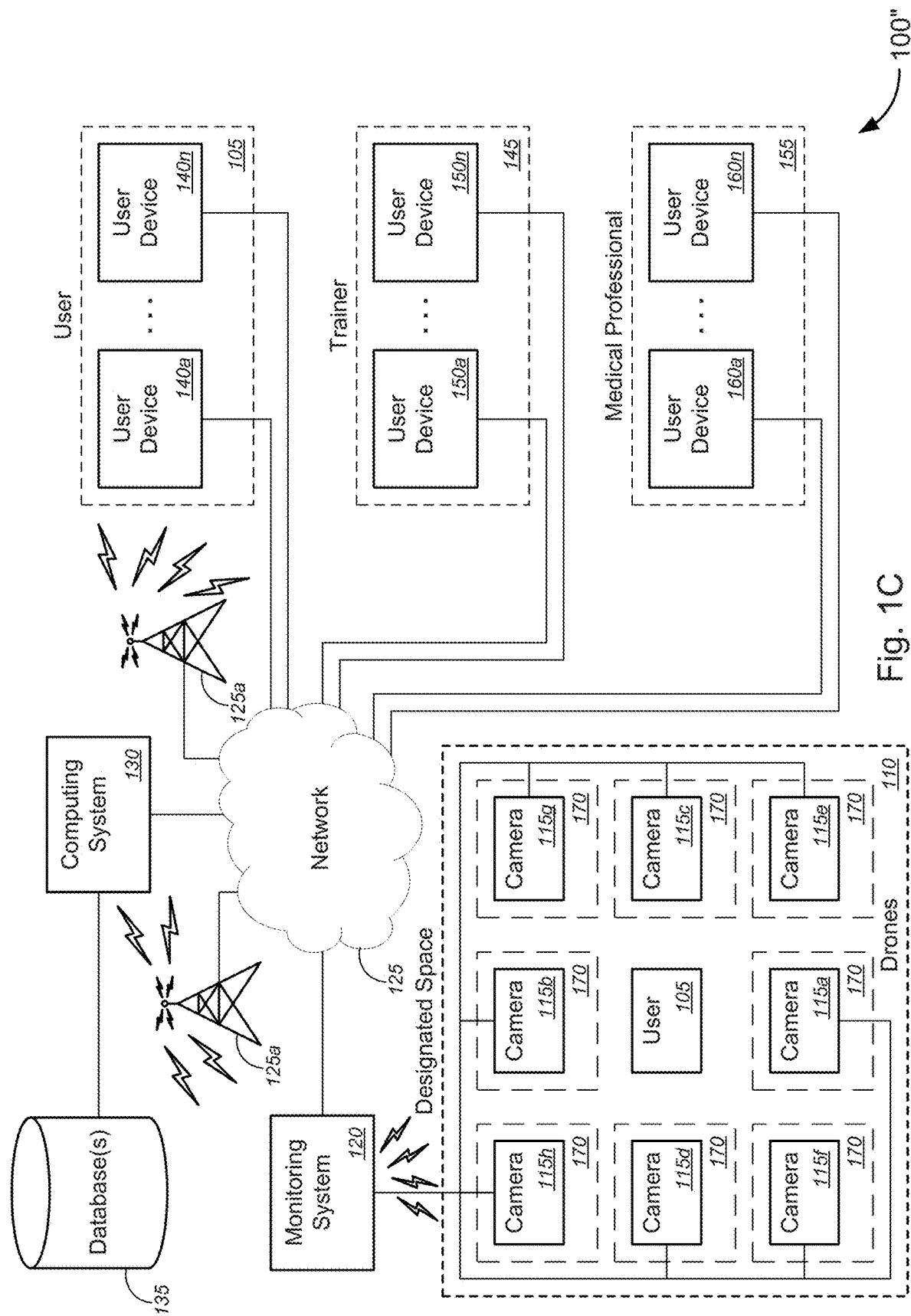

With reference to the figures, FIGS. 1A-1C (collectively, "FIG. 1") are schematic diagrams illustrating various embodiments of a system 100, 100', or 100" (collectively, "system 100") for implementing image-based physiological status or physical condition determination of users and generating remediation plans as appropriate. In FIG. 1, system 100 might comprise a user 105 who might be performing one or more sets of motions (also referred to herein as "tests" or the like, to determine existence of a particular injury(ies) or likelihood of suffering the particular injury(ies)) in a designated space 110. Herein, the user might be an athlete, a patient, or a regular person seeking injury evaluation, or the like, while the tests might be used to diagnosis potential injuries, including, but not limited to, a concussion, a torn anterior cruciate ligament ("ACL"), a torn posterior cruciate ligament ("PCL"), a torn medial collateral ligament ("MCL"), a torn lateral collateral ligament ("LCL"), an ankle sprain, a groin pull, a hamstring strain, shin splints, and tennis elbow, and/or the like. In some embodiments, the designated space 110 might include, without limitation, one of an indoor space, a man-made portable enclosure, and/or an outdoor space, or the like. According to some embodiments, the designated space might be one of a sports stadium, an athletic field, an ice rink, a ski slope, a trail, a roadway, or a pathway, and/or the like.

System 100 might further comprise one or more cameras (or image/video capture devices) 115 that are used to capture images or videos of views of the user (including, but not limited to, one or more of perspective views of the user, elevation views of the user, plan views of the user, and/or the like from any angle or combination of angles). In the embodiment of FIG. 1, an eight-camera array of cameras is used, which includes, cameras 115a-115h. The various embodiments, however, are not so limited, and any suitable number of cameras from one through twelve, and more than twelve, may be used as appropriate. The cameras in the array may also be placed, in some embodiments, at equal distances from the user, or, in alternative embodiments, at varying distances from the user, as appropriate or as desired. FIGS. 2 and 3 below show the relative positions and fields of views of the cameras 115 with respect to the user's position in the designated space. In some embodiments, marker-based motion capture technology may be used for capturing and analyzing the motions of the user. In various embodiments, however, marker-less motion capture technology may be used instead.

In various embodiments, system 100 might further comprise a monitoring system 120, which might be a local computing device that compiles the image or video data from each of the one or more cameras 115, that sends the captured image-data or captured views of the user to a computing system 130 via a network 125, and in some cases, via one or more telecommunications relay systems 125a. The one or more telecommunications relay systems 125a might include, without limitation, one or more wireless network interfaces (e.g., wireless modems, wireless access points, and the like), one or more towers, one or more satellites, and/or the like. In FIG. 1, in general, the lines connecting components of the system can represent either wired connection between two or more components, wireless communications between the two or more components, or both. The lightning bolt symbols, however, represent and highlight wireless communications capability between the two or more components, and the combination of the lines and the lightning bolts represents that one or both of these two types of communications (wired and/or wireless) may be implemented as depicted, or the like. System 100 might further comprise database(s) 135 in communication with server 130.

As described in detail below with respect to FIGS. 4 and 5, the computing system 130 (in some cases in conjunction with database(s) 135) might perform analysis of the captured views of the user to determine a physical condition or physiological status of the user or the probability that the user will suffer the physical condition. In some embodiments, the computing system 130 might send, via network 125 (and in some cases, via the one or more telecommunications relay systems 125a) a notification (via one or more of a software application ("app"), a text message, a short message service ("SMS") message, a multimedia messaging service ("MMS") message, an e-mail message, or a chat message, and/or the like) to at least one of one or more user devices 140a-140n (collectively, "user devices 140") associated with the user 105, one or more user devices 150a-150n (collectively, "user devices 150") associated with the user's trainer 145 (which might include, without limitation, gym trainer, sports team physiotherapist, sports team coach, etc.), and/or one or more user devices 160a-160n (collectively, "user devices 160") associated with the user's physician or other medical professional 155 (which might include, but is not limited to, the user's physician, surgeon, nurse, physiotherapist, etc.). The notification might indicate the determined physical condition or physiological status of the user or the determined probability that the user will suffer the physical condition, based on the image-based analysis performed by the computing system 130.

In some embodiments, assuming that it is determined that the user can recover from the determined existing physical condition or the determined likelihood of suffering from the physical condition, the computing system 130 might send a remediation plan to the user device(s) 140 associated with the user 105. In some cases, the remediation plan might first be sent to the user devices 150 and/or 160 associated with the user's trainer 145 and/or the user's physician or other medical professional 155, respectively, for review prior to sending to the user's device(s) 140. In some instances, the remediation plan might be designed by the user's trainer 145 and/or the user's physician or other medical professional 155.

FIG. 1B is similar to FIG. 1A, except that, in FIG. 1B, system 100' might further comprise an enclosure 165 that is positioned around the user 105 and within the designated space 110. The enclosure 165, in some cases, might include, without limitation, a permanent enclosure (including, but not limited to, a building, a room in a building, a permanent outdoor full enclosure, a permanent outdoor partial enclosure), a temporary indoor enclosure (including, but not limited to, a tent, a commercial enclosure, a portable habitat, an enclosure frame with fabric walls (which might be made of nylon, cloth, or other materials, etc.), and/or the like), a temporary outdoor enclosure (including, but not limited to, a tent, a commercial enclosure, a portable habitat, an enclosure frame with fabric walls (which might be made of nylon, cloth, or other materials, etc.), and/or the like).

FIG. 1C is similar to FIG. 1A, except that, in FIG. 1C, system 100" might further comprise one or more drones 170, on each of which is mounted one of the cameras 115. The one or more drones 170 might include, without limitation, at least one of an aerial-based drone (as shown in the embodiment of FIG. 1C), a ground-based drone (not shown), an aquatic-based drone (not shown), and/or the like.

Although FIG. 1 shows a single user being diagnosed at a time, the various embodiments are not so limited, and the system 100 can be implemented to diagnose multiple users (i.e., two or more users) at the same time, either post image/video capture and/or in real-time or near-real-time.

Figure 2B:
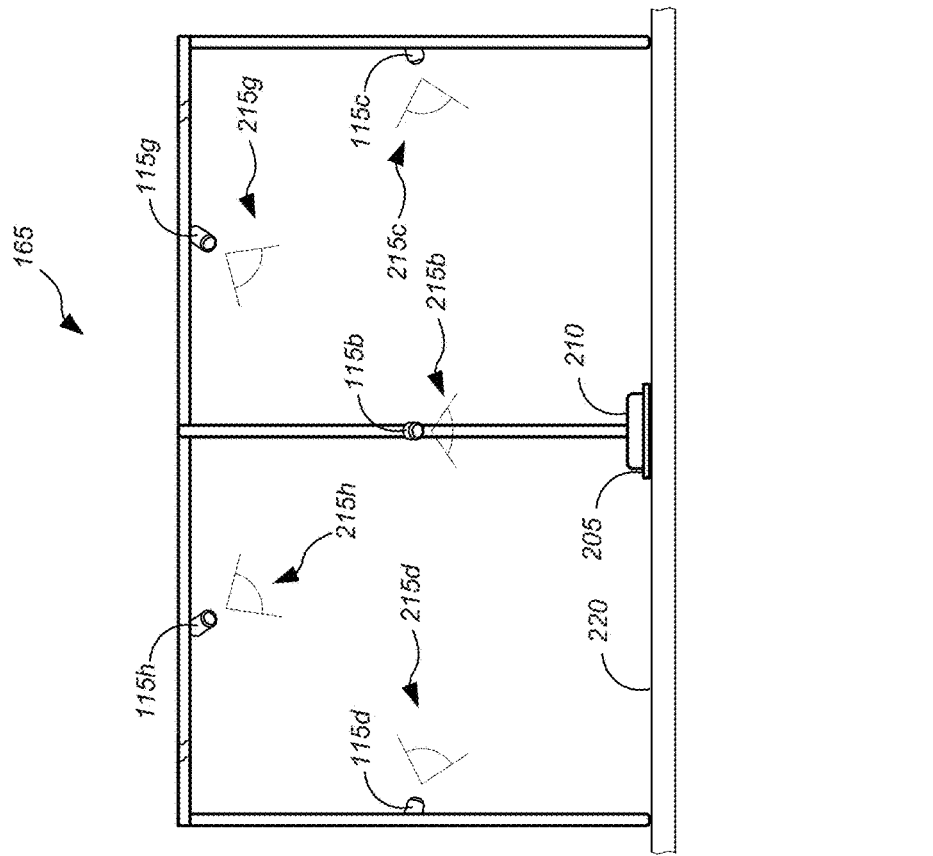
Figure 2A:
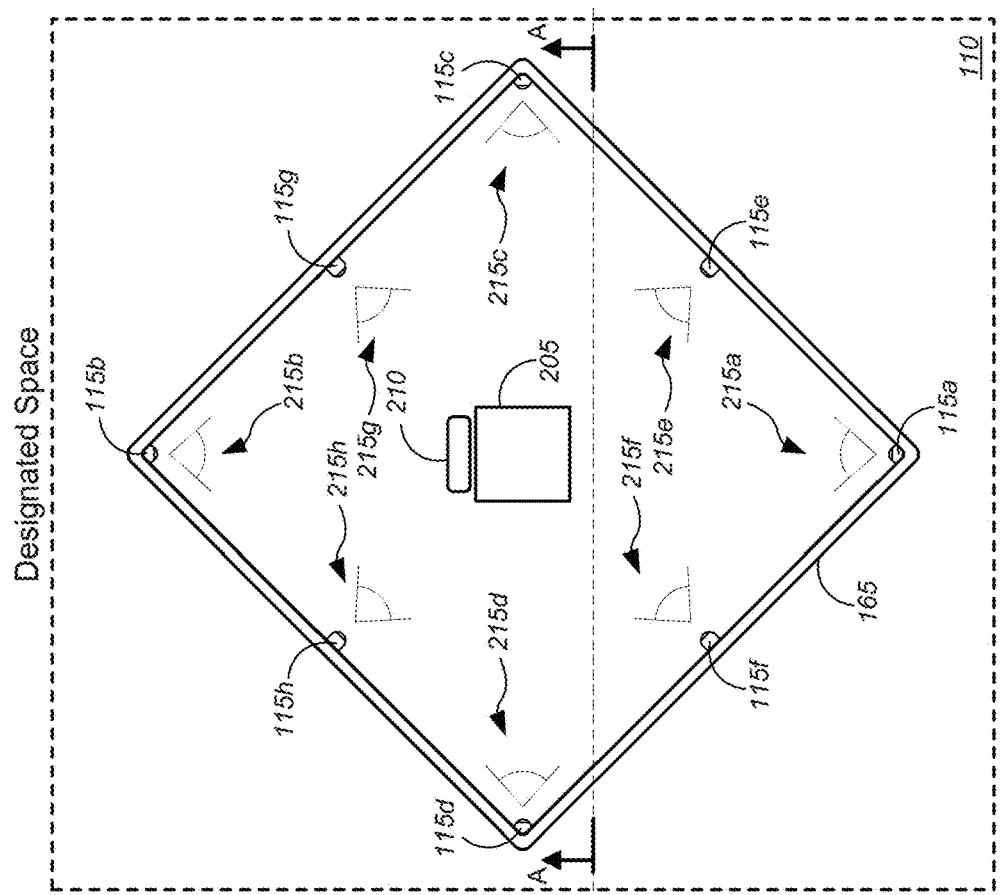
Figure 2C:
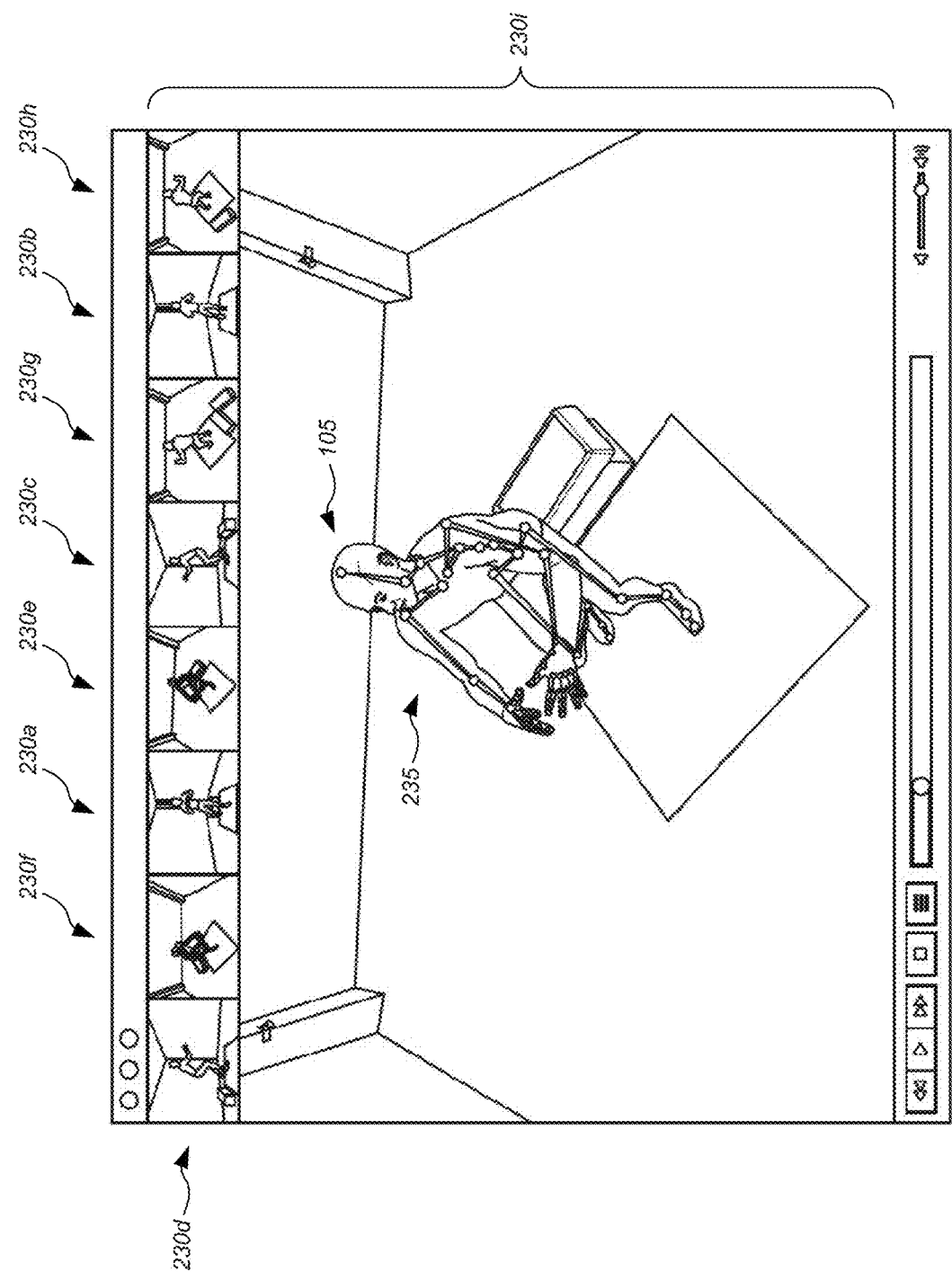

FIGS. 2A-2E (collectively, "FIG. 2") are schematic diagrams illustrating various enclosure-based systems 200 or 200' (collectively, "system 200") for implementing image-based physiological status or physical condition determination of users and generating remediation plans as appropriate, in accordance with various embodiments. FIGS. 2A-2C illustrate a system 200 having an eight camera array of cameras, while FIGS. 2D and 2E illustrate a system 200' having a twelve camera array of cameras. The various embodiments, however, are not so limited, and any number of cameras may be used in the array. FIG. 2A depicts a top or plan view of the system 200, while FIG. 2B depicts a partial front elevation view of the system 200 taken along the A-A direction of FIG. 2A, and FIG. 2C depicts an example embodiment of a graphical user interface ("GUI") that displays the eight different views of the user along with a ninth view that has a virtual skeletal framework overlaid over the image/video-captured view of the user. FIG. 2D is a top or plan view of the system 200', while FIG. 2E is a front elevation view of the system 200' taken along the B-B direction of FIG. 2D.

In FIG. 2, designated space 110, cameras 115, and enclosure 165 are similar, if not identical, to the designated space 110, the one or more cameras 115, and the enclosure 165, respectively, as described in detail above with respect to FIG. 1, and similar descriptions of these components in system 100 of FIG. 1 similarly apply to the corresponding components in FIG. 2.

With reference to FIGS. 2A and 2B, system 200 might comprise within designated space 110, an enclosure 165, which is shown in FIGS. 2A and 2B as a frame of the enclosure. In some cases, the frame might be made of materials including, but not limited to, at least one of metal, plastics, ceramics, polymers, and/or the like. For portability and ease of transportation, the frame might comprise a plurality of modular components that are removably affixed to each other. In the embodiment of FIGS. 2A-2C, an eight camera array of cameras 115a-115h (collectively, "cameras 115") may be mounted at varying heights at particular positions on the frame of the enclosure 165.

As shown in FIG. 2A, a mat 205 might be positioned on a ground surface 220 at approximately the middle of the frame of the enclosure 165. In some embodiments, the mat 205 might be a soft or hard foam, plastic, or the like. The mat 205, in some cases, might be designed to provide sufficient cushioning to prevent hard impact by the feet of the user (shown in FIGS. 1 and 2C, but not shown in FIGS. 2A and 2B), while providing sufficient stiffness to prevent further injury or to prevent inaccuracies in the image-based analysis due to unevenness of the mat from over-cushioning or the like. According to some embodiments, a step 210 might be positioned adjacent the mat 205 (in some cases, behind where the user would be located) to allow for motions that involve a step, a deep lunge, etc. In some embodiments, the mat 205 might merely be used as a position marker for the user to ensure optimal positioning for the image-capture process.

As shown in FIGS. 2A-2C, cameras 115a, 115b, 115c, and 115d might be mounted at about a middle portion of the vertical posts of the frame of the enclosure 165 (in some cases, at a height that is between an average waist height to an average head height among a population set; in some instances, adjustably mounted), and might be oriented to capture the front view 215a, the rear view 215b, the left-side view 215c, and the right-side view 215d, respectively, of a user (shown in FIG. 2C) when the user performs the one or more sets of motions on the mat 205. Cameras 115e, 115f, 115g, and 115h might be mounted at about a middle portion of the horizontal top struts of the frame of the enclosure 165, and might be oriented to capture the front-left perspective view 215e, the front-right perspective view 215f, the rear-left perspective view 215g, and the rear-right perspective view 215h, respectively, of the user (shown in FIG. 2C) when the user performs the one or more sets of motions on the mat 205. Herein, "views 215" refer to the front, rear, left-side, or right-side of the user. With reference to FIG. 2C, GUI 225 displays eight sub-panels 230a-230h that show the front view 215a, the rear view 215b, the left-side view 215c, and the right-side view 215d, the front-left perspective view 215e, the front-right perspective view 215f, the rear-left perspective view 215g, and the front-left perspective view 215h, respectively, of the user 105. GUI 225 also displays a main panel 230i that shows a ninth view of the user that includes a skeletal framework 235 overlaid over the image/video of the user 105. Although FIG. 2C shows the front left view as the basis for the ninth view, any of the other views may be used as appropriate or as desired. In FIG. 2C, the nine views 230a-230i are each shown as a single frame within a multiple-frame video segment.

The system 200' of FIGS. 2D and 2E is similar to system 200 of FIGS. 2A-2C, except that four additional cameras 115i-115l are used in the array of cameras. As shown in FIGS. 2D and 2E, cameras 115i, 115j, 115k, and 115l might be mounted at about a top portion of the frame of the enclosure 165 (in some cases, at a junction between a vertical post and two horizontal struts of the frame), and might be oriented to capture the top-front perspective view 215i, the top-rear perspective view 215j, the top-left perspective view 215k, and the top-right perspective view 215l, respectively, of the user (shown in FIG. 2C) when the user performs the one or more sets of motions on the mat 205. System 200' of FIGS. 2D and 2E is otherwise similar to system 200 of FIGS. 2A-2C, and similar descriptions apply accordingly.

FIGS. 3A and 3B (collectively, "FIG. 3") are schematic diagrams illustrating a drone-based system 300 for implementing image-based physiological status or physical condition determination of users and generating remediation plans as appropriate, in accordance with various embodiments. FIG. 3A depicts a top or plan view of the system 300, while FIG. 3B depicts a partial front elevation view of the system 300 taken along the C-C direction of FIG. 3A. System 300 of FIG. 3 is similar to system 200 of FIG. 2, except that instead of the enclosure 165, an array of aerial-based drones 340a-340h are used, and the cameras 115a-115h are mounted on the aerial-based drones 340a-340h, respectively.

In FIG. 3, designated space 110 and cameras 115 are similar, if not identical, to the designated space 110 and the one or more cameras 115, respectively, as described in detail above with respect to FIG. 1, and similar descriptions of these components in system 100 of FIG. 1 similarly apply to the corresponding components in FIG. 3. Mat 305, step 310, views 315a-315h, and ground surface 320 are similar, if not identical, to the mat 205, the step 210, the views 215a-215h, and the ground surface 220, respectively of FIG. 2, and similar descriptions apply similarly.

Although an enclosure is used for mounting the cameras 115 in the embodiments of FIG. 2 and aerial-based drones are used for mounting the cameras 115 in the embodiment of FIG. 3, the various embodiments are not so limited and cameras may be mounted on mechanical arms, ground-based drones, tracks on the frames of the enclosure, and/or the like, as appropriate or as desired. The cameras may be mounted on a mounting frame that allows for pan and tilt functionality, with in-built zoom functions inherent with the cameras themselves. The mechanical arms and the tracks on the frames of the enclosure each allow for additional lateral or vertical movement of the pan/tilt camera mounting frames (and thus the cameras), while the drones allow for greater mobility of the pan/tilt camera mounting frames (and thus the cameras). For example, aerial-based drones can track a skier or snowboarder racing down a track. In sports stadiums, aerial-based or ground-based drones might follow (and capture with the cameras) the sports action by moving along with the players, while mechanical arms and/or tracks on frames of structures on the stadium structure might allow for movement of the pan/tilt camera mounting frames to move along the movement arcs or tracks of these mounts, and stationary pan/tilt camera mounts might merely pan or tilt the cameras toward the action (relying on the camera zoom functionality to focus in on the action). Other similar implementations of the camera can be utilized as appropriate or desired. The image-based analysis can be performed as described in detail below with respect to FIGS. 4 and 5.

FIGS. 4A-4F (collectively, "FIG. 4") are system flow diagrams illustrating a method 400 for implementing image-based physiological status or physical condition determination of users and generating remediation plans as appropriate, in accordance with various embodiments. While the techniques and procedures of the method 400 is depicted and/or described in a certain order for purposes of illustration, it should be appreciated that certain procedures may be reordered and/or omitted within the scope of various embodiments. Moreover, while the method illustrated by FIG. 4 can be implemented by (and, in some cases, are described below with respect to) system 100 of FIG. 1 (or components thereof), system 200 of FIG. 2 (or components thereof), system 300 of FIG. 3 (or components thereof), the method may also be implemented using any suitable hardware implementation. Similarly, while system 100 (and/or components thereof), system 200 of FIG. 2 (or components thereof), system 300 of FIG. 3 (or components thereof), and/or the like can operate according to the method illustrated by FIG. 4 (e.g., by executing instructions embodied on a computer readable medium), systems 100, 200, and/or 300 can also operate according to other modes of operation and/or perform other suitable procedures.

Figure 4A:
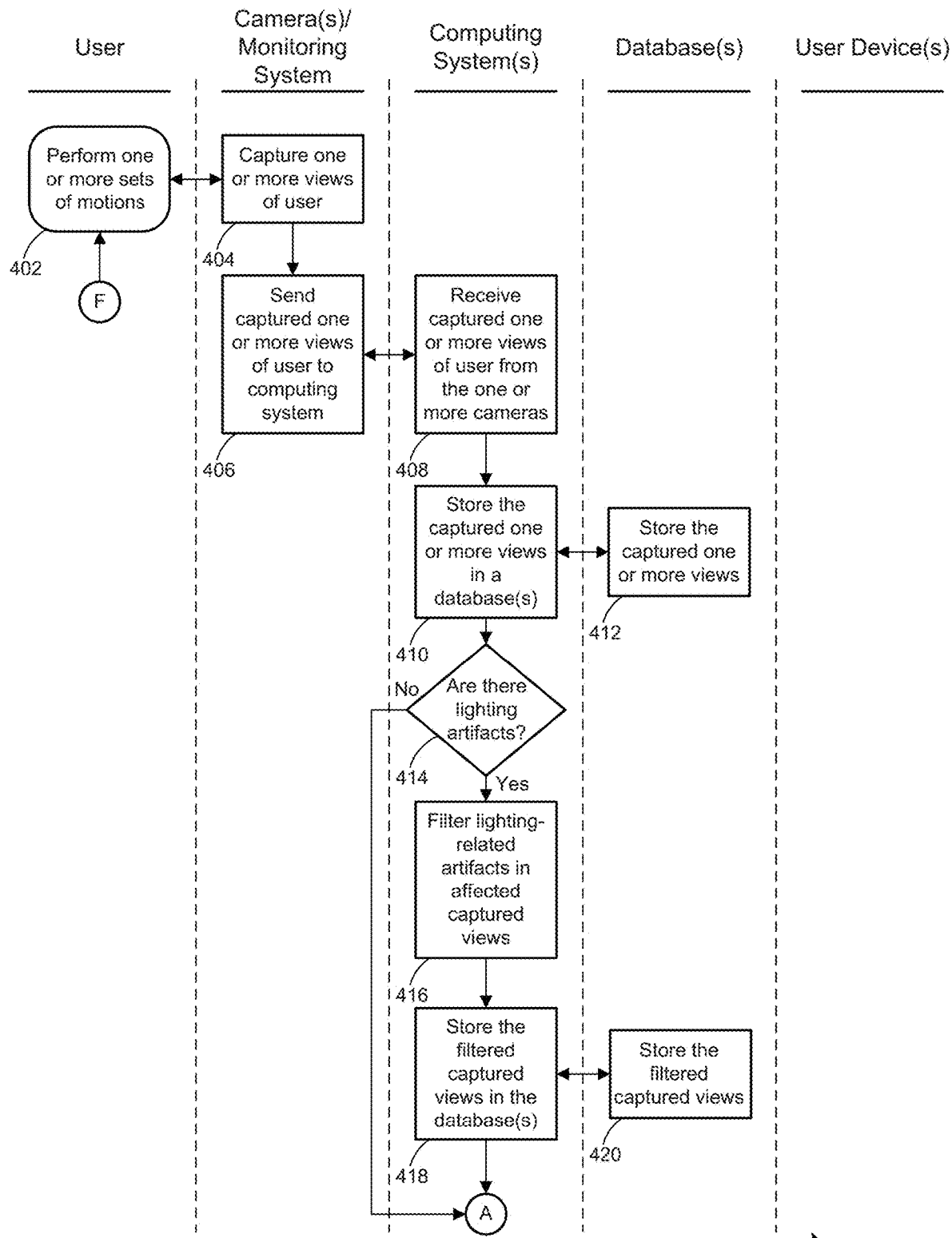
FIGS. 4A-4F are system flow diagrams illustrating a method for implementing image-based physiological status or physical condition determination of users and generating remediation plans as appropriate, in accordance with various embodiments.
Figure 4B:
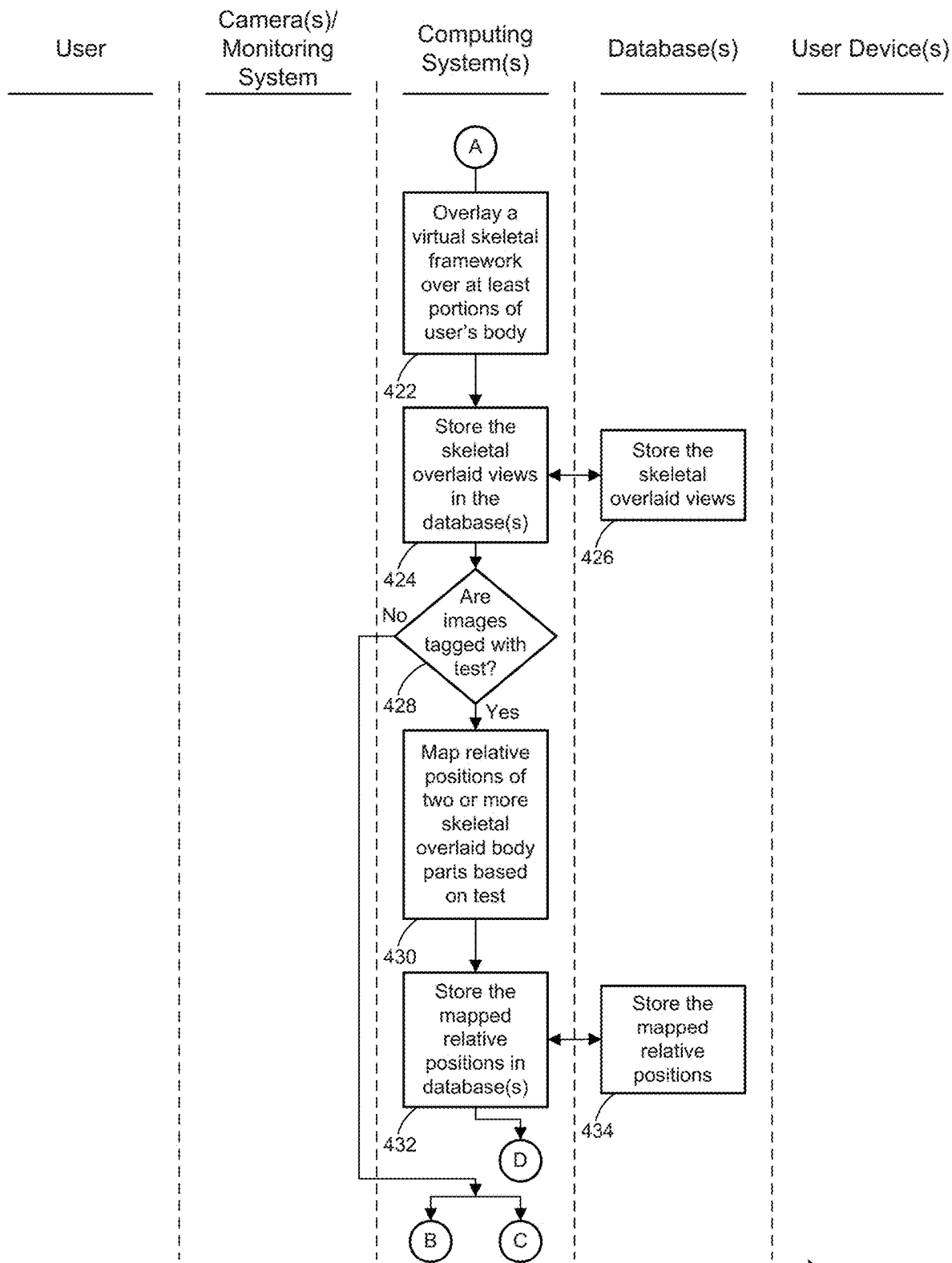
Figure 4C:
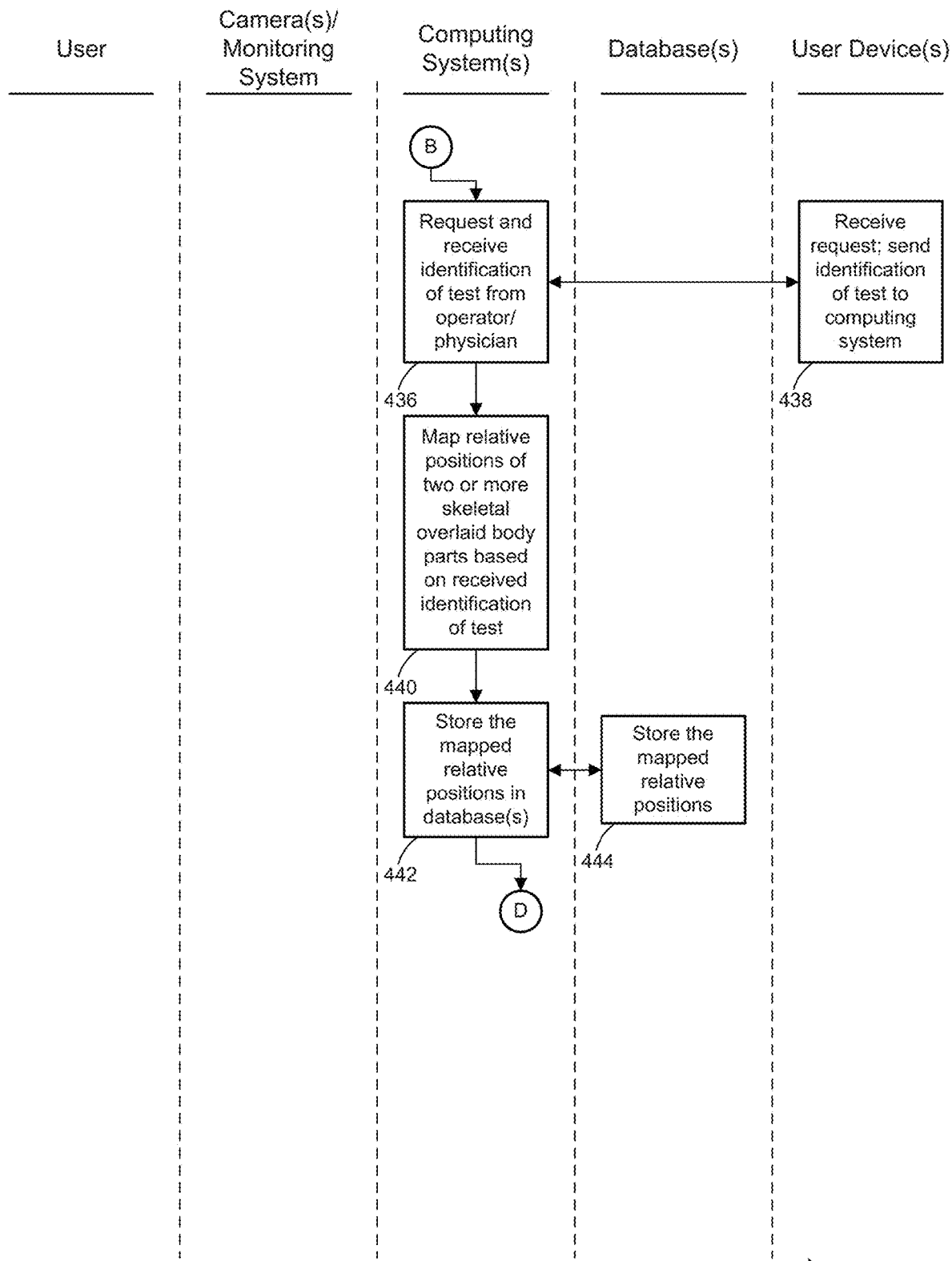
Figure 4D:
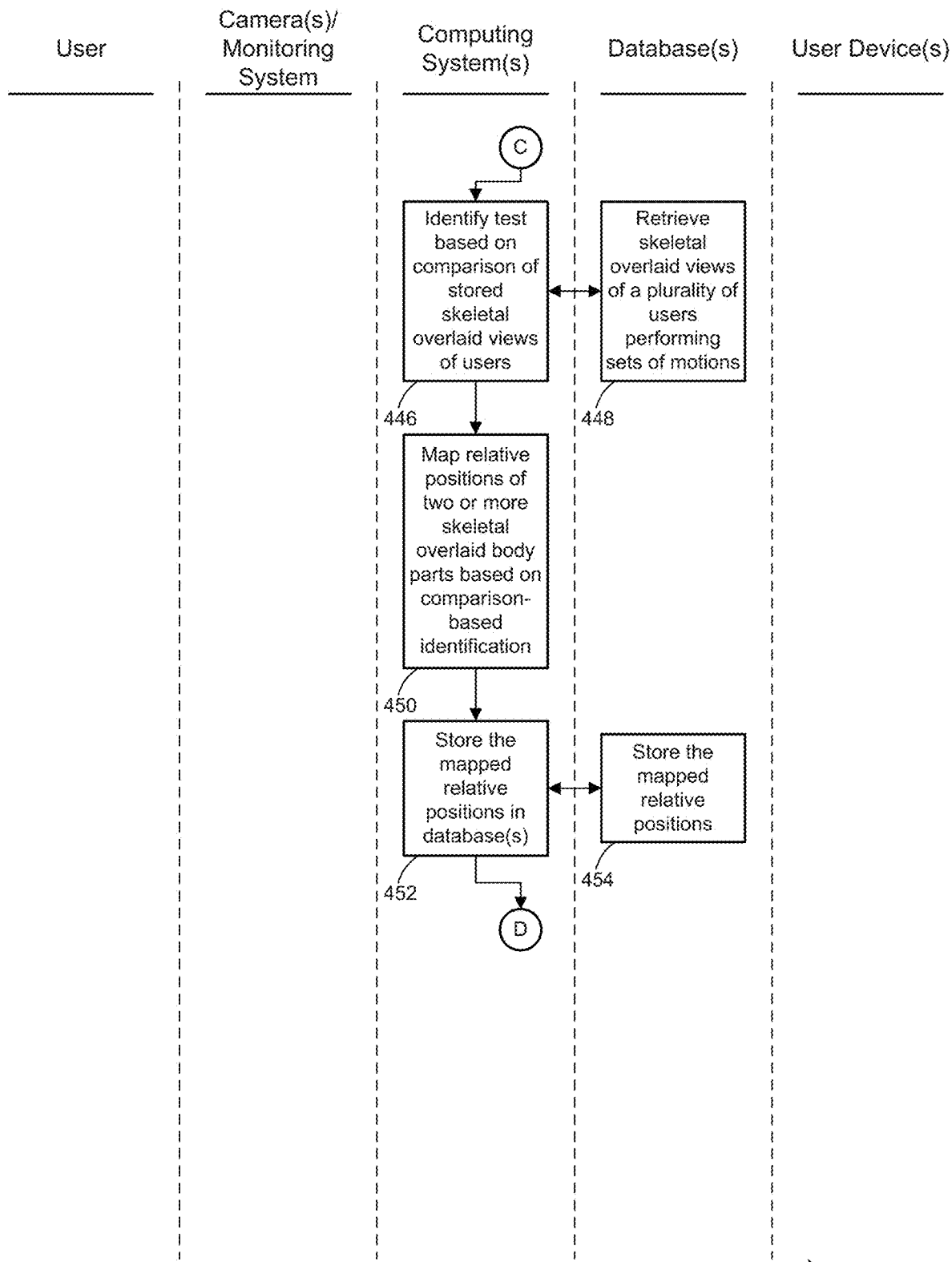
Figure 4E:
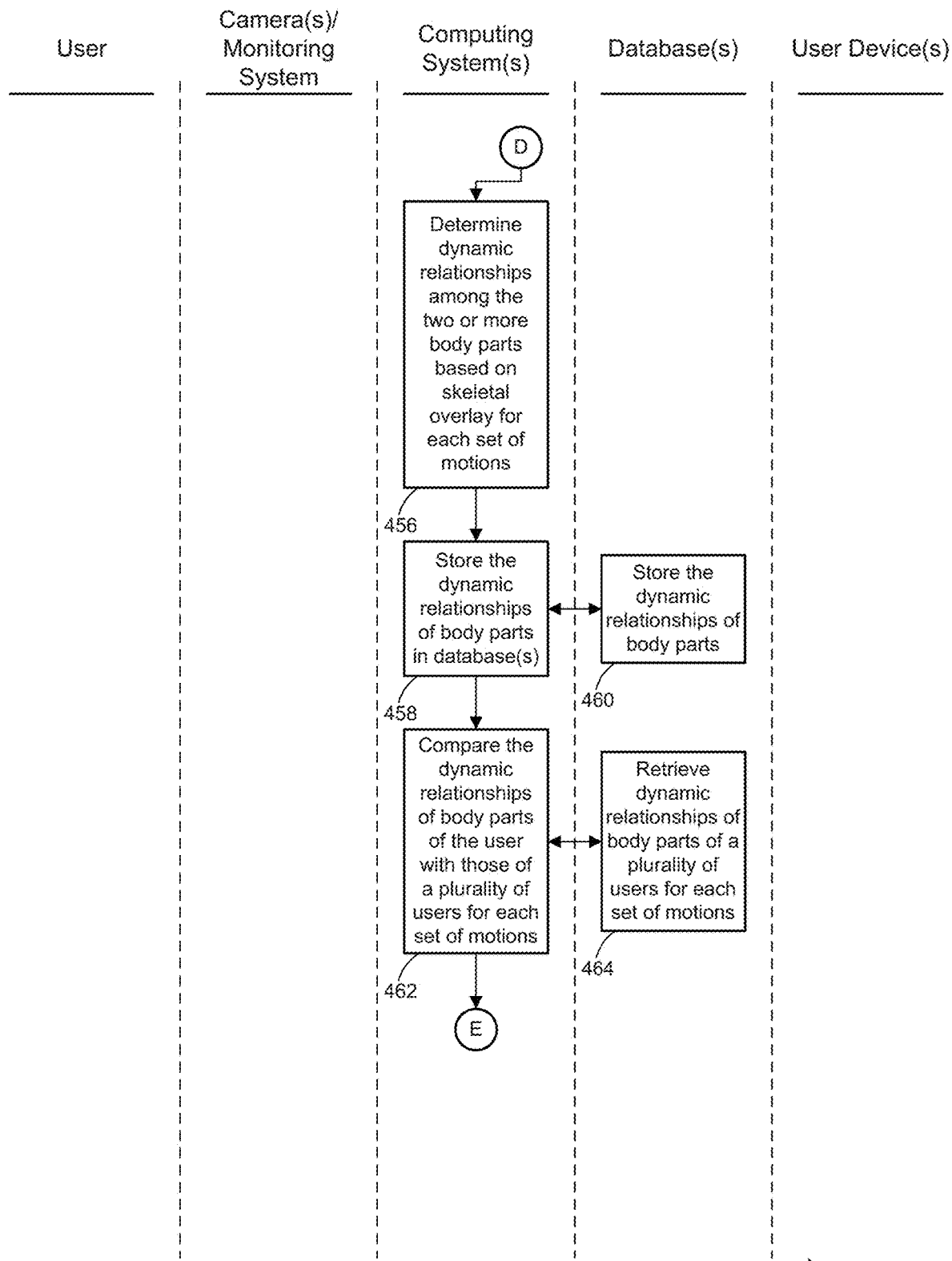
Figure 4F:
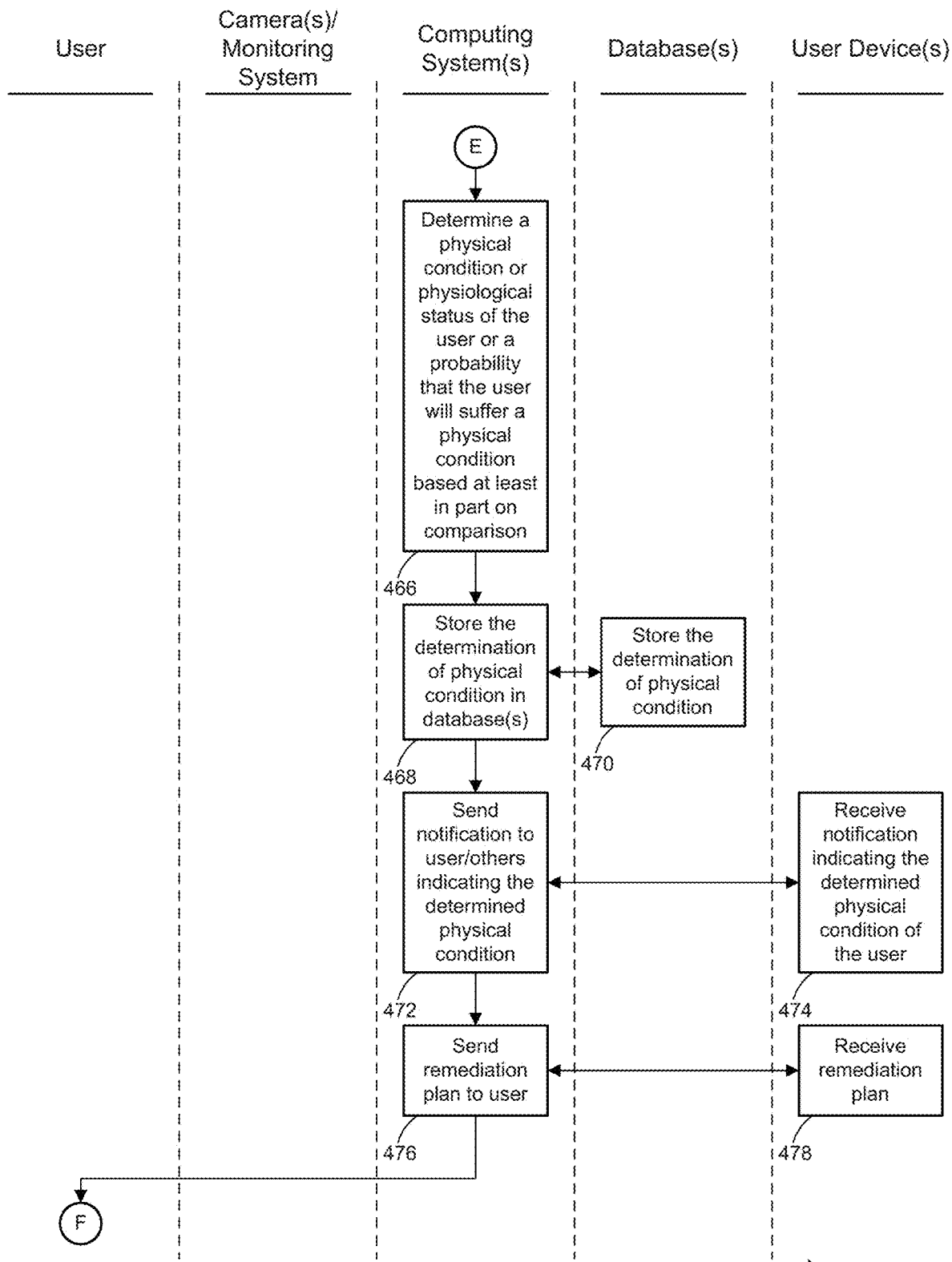

In FIG. 4, method 400 in FIG. 4A continues onto FIG. 4B, linked by the circular marker denoted by "A," which continues from FIG. 4B onto FIG. 4C, linked by the circular markers denoted by "B," and continues from FIG. 4B onto FIG. 4D, linked by the circular markers denoted by "C." Method 400 in FIGS. 4B-4D continue onto FIG. 4E, linked by the circular markers denoted by "D," while method 400 in FIG. 4E continues onto FIG. 4F, linked by the circular markers denoted by "E." Method 400 in FIG. 4F returns back to FIG. 4A linked by the circular marker denoted "F."

With reference to FIG. 4A, method 400 might comprise, at block 402, a user performing one or more sets of motions. Each set of motions include, without limitation, at least one or any combination of squats, jumps, forward motion, lateral motion, backward motion, single leg balancing, knee bends at various angles, elbow bends at various angles, abdominal bends at various angles, arm rotations, partial arm rotations, upper body stretches, lower body stretches, full body stretches, leg extensions, arm extensions, head rotations, shoulder rotations, hip rotations, ankle rotations, foot rotations, wrist rotations, arm curls, legs curls, and/or the like. Each set of motions might be configured or designed, based at least in part on applicable or appropriate medical research, to test likelihood of a particular type of injury.

In an alternate set of embodiments, a combination of the following motions, based on current medical research (and as also described below with respect to FIGS. 9A-9S), might be used to identify most, if not all biomechanical-type injuries or biomechanical-type injury risks, which might include, without limitation, a knee injury, an ankle sprain, an Achilles tear, a groin pull, a groin injury, a hamstring strain, a hamstring injury, a hip impingement, shin splints, tennis elbow, medial tibial stress syndrome ("MTSS"), tibial stress fracture, patellofemoral pain syndrome ("PFPS"), concussion, and/or the like: two-legged squat, left leg lunge, right leg lunge, left leg squat, right leg squat, left leg balancing, a right leg balancing, vertical jump, drop from a box (also referred to as "box drop"), drop from a box immediately transitioning to a vertical jump (also referred to as "box drop to vertical jump"), and shoulder rotations. Herein, knee injuries might refer to injuries including, but are not limited to, at least one of a torn anterior cruciate ligament ("ACL"), a torn posterior cruciate ligament ("PCL"), a torn medial collateral ligament ("MCL"), a torn lateral collateral ligament ("LCL"), and/or the like. The method and system described herein can identify or diagnose these conditions (i.e., potential injury risks or injuries, etc.), based at least in part on analysis of the captured images of the user performing this set of motions, particularly in comparison with baseline captured images of the user performing the same set of motions and/or in comparison with captured images of each of a plurality of users performing the same set of motions—that is, comparing captured images of the same motion (at particular points in the motion) as performed by each of the user (at the current or latest time), the user (during the baseline phase), and a plurality of users, and repeating for each frame of the images corresponding to the same particular points in each motion.

The motions to test for biomechanical injuries may, in some embodiments, be set in the order as listed above. Alternatively, the motions to test for biomechanical injuries may be made in any order. In yet other embodiments, the motions to test for biomechanical injuries may be randomized in terms of performance order, and the user performing such motions may be asked to do so according to the randomized order or randomized list of motions. In some cases, having the user perform the lunges (i.e., left leg lunge and right leg lunge) first may result in sloppy technique by the user for subsequent motions (i.e., the other motions listed above). Having the user perform the two-legged squat as the first motion in the set of motions, on the other hand, allows the user to quickly find his or her balance and center, in order to perform the other techniques or motions; the squat as the first motion in the set of motions also avoids any subsequent sloppy techniques that may result after performing the lunge, even if the lunge is performed as the second motion in the set of motions. With reference to the single leg balances, based on medical studies, having the user perform single leg balances (i.e., left leg balancing and right leg balancing) while the user is well rested has little to no predictive value. However, when the user is not rested (i.e., after performing a number of other motions), single leg balances (i.e., left leg balancing and right leg balancing) are very much predictive of various conditions. Accordingly, it is advantageous to have the user perform single leg balances after performing a number of other motions in the set of motions (such as after the squats and lunges, for example).

Other than these preferred orderings of particular motions in the set of motions, the other motions in the set of motions can be performed in any suitable or desired order.

With reference to concussion diagnosis, in particular, a combination of the following motions, based on current medical research, might be used to identify postural sway indicative of concussion: standing on a single leg with eyes open (both left leg and right leg), standing on a single leg with eyes closed (both left leg and right leg), standing with both legs in a natural stance, and standing with the feet of both legs spaced together (i.e., with both feet touching each other). The motions of postural sway evaluation (also referred to as "postural sway test battery") may, in some embodiments, be made in any order. In some cases, the motions of the postural sway test battery may be randomized in terms of performance order, and the user performing such motions may be asked to do so according to the randomized order or randomized list of motions. The method and system described herein can identify or diagnose a concussion or a risk of concussion, based at least in part on analysis of the captured images of the user performing this set of motions (see the process at block 462, block 545, and block 550 below), particularly in comparison with baseline captured images of the user performing the same set of motions (in some cases, in a different order based on the randomization) and/or in comparison with captured images of each of a plurality of users performing the same set of motions (in some cases, each in a different order based on the randomization)—that is, comparing captured images of the same motion (at particular points in the motion) as performed by each of the user (at the current or latest time), the user (during the baseline phase), and a plurality of users, and repeating for each frame of the images corresponding to the same particular points in each motion.

At block 404, one or more cameras (e.g., the one or more cameras 115 of FIGS. 1-3, or the like) and/or a monitoring system (e.g., the monitoring system 120 of FIG. 1, or the like) (collectively referred to herein as "monitoring system") might capture one or more views of the user (including, but not limited to, one or more of perspective views of the user, elevation views of the user, plan views of the user, and/or the like from any angle or combination of angles). The monitoring system, at block 406, might send the captured one or more views of the user to a computing system (e.g., computing system 130 of FIGS. 1-3, or the like), which might receive the captured one or more views of the user from the monitoring system (block 408).

At block 410, the computing system might store the captured one or more views of the user in a database(s) (e.g., database 135 of FIG. 1, or the like), which might store the captured one or more views (at block 412). At block 414, the computing system might determine whether there are any lighting artifacts, which might be present due to sunlight in an outdoor setting, bright lights in an indoor or partial indoor setting, low light conditions in an indoor or partial indoor setting, and/or the like. Here, "partial indoor setting" might refer to a portable enclosure setting (including, tents, commercial enclosures, portable habitats, etc.), a covered patio/porch setting (in which at least one side is not covered, including pergolas, extended roofs, roof overhangs, etc.), and/or the like. If not, the process skips to block 422 in FIG. 4B following marker "A." If so, the process continues to block 416. At block 416, the computing system might filter any lighting or lighting-related artifacts in any (and all) affected captured views. The computing system might store the filtered captured views the in the database(s) (block 418), which might in turn store the filtered captured views (block 420). The process might subsequently continue to block 422 in FIG. 4B following marker "A."

Turning to FIG. 4B, at block 422, the computing system might overlay a virtual skeletal framework over at least portions of the user's body in the captured (or filtered captured) one or more views of the user, and might store the skeletal overlaid views in the database(s) (block 424), which might store the skeletal overlaid views (block 426). At block 428, the computing system might determine whether at least one of the captured images or views of the user might be tagged with the type of test being performed on the user (i.e., set of motions being performed by the user to determine a potential type of injury that the user might have or might likely suffer if a remediation plan is not implemented). In some cases, the tags might include a header in the image file(s). Alternatively, the tags might include embedded coding in the image file(s). Other types of tags may also be used, as understood by those skilled in the art. If not, the process continues to one of block 436 in FIG. 4C following marker "B" or block 446 in FIG. 4D following marker "C." If so, the process continues to block 430. At block 430, the computing system might map relative positions of the two or more skeletal overlaid body parts based at least in part on the test as indicated in the tag(s). The computing system might store the mapped relative positions of the two or more skeletal overlaid body parts in the database(s) (block 432), which might store the mapped relative positions of the two or more skeletal overlaid body parts (block 434). The process might subsequently proceed to block 456 in FIG. 4E following marker "D."

With reference to FIG. 4C, at block 436, the computing system might request (from one or more of a user device associated with the user, a user device associated with the user's trainer, a user device associated with the user's physician or other medical professional, or the like (collectively, the "user device")) and receive identification of the test being performed on the user (i.e., set of motions being performed by the user to determine a potential type of injury that the user might have or might likely suffer if a remediation plan is not implemented). The user device might receive the request and might send the identification of the test (in some cases, based on user input by the person associated with the device, i.e., the corresponding one of the user, the user's trainer, or the user's physician/other medical professional, or the like) to the computing system (block 438).

At block 440, the computing system might map relative positions of the two or more skeletal overlaid body parts based at least in part on the test as identified by the user device. The computing system might store the mapped relative positions of the two or more skeletal overlaid body parts in the database(s) (block 442), which might store the mapped relative positions of the two or more skeletal overlaid body parts (block 444). The process might subsequently proceed to block 456 in FIG. 4E following marker "D."

With reference to FIG. 4D, at block 446, the computing system might identify the test being performed on the user (i.e., set of motions being performed by the user to determine a potential type of injury that the user might have or might likely suffer if a remediation plan is not implemented) based on a comparison of skeletal overlaid views of a plurality of users that are stored in the database(s), which involves retrieving from the database(s) the skeletal overlaid views of a plurality of users performing the same sets of motions (block 448). At block 450, the computing system might map relative positions of the two or more skeletal overlaid body parts based at least in part on the comparison-based identification of the test. The computing system might store the mapped relative positions of the two or more skeletal overlaid body parts in the database(s) (block 452), which might store the mapped relative positions of the two or more skeletal overlaid body parts (block 454). The process might subsequently proceed to block 456 in FIG. 4E following marker "D."

Turning to FIG. 4E, at block 456, the computing system might determine dynamic relationships among the two or more body parts based at least in part on the skeletal overlay for each set of motions. The computing system might store the dynamic relationships among the two or more body parts in the database(s) (block 458), which might store the dynamic relationships among the two or more body parts (block 460). At block 462, the computing system might compare the dynamic relationships among the two or more body parts of the user with those of each of a plurality of users for each set of motions, which might involve retrieving the dynamic relationships among the two or more body parts of each of a plurality of users for each set of motions (which might include a previously determined diagnosis or determination of existence or likelihood of the particular injury in the particular user of the plurality of users for that set of motions) (block 464). As described above, such analysis might include, without limitation, comparing the captured images of the user performing the set of motions (in some cases, comparing the dynamic relationships among the two or more body parts of the user, which, in some instances, might include the skeletal overlay) with baseline captured images of the same user performing the same set of motions (in some cases, comparing with the dynamic relationships among the two or more body parts of the user, which, in some instances, might include the skeletal overlay) and/or in comparison with captured images of each of a plurality of users performing the same set of motions (in some cases, comparing with the dynamic relationships among the two or more body parts of each of the plurality of users, which, in some instances, might include the skeletal overlay)—that is, comparing captured images of the same motion (at particular points in the motion) as performed by each of the user (at the current or latest time), the user (during the baseline phase), and a plurality of users, and repeating for each frame of the images corresponding to the same particular points in each motion. The process might subsequently proceed to block 466 in FIG. 4F following marker "E."

With reference to FIG. 4F, at block 466, the computing system might determine a physical condition or physiological status of the user or a probability that the user will suffer a physical condition, based at least in part on the comparison (performed at block 462). The computing system might store the determination of the physical condition or physiological status of the user or the probability that the user will suffer the physical condition in the database(s) (block 468), which might store the determination of the physical condition or physiological status of the user or the probability that the user will suffer the physical condition (block 470).

At block 472, the computing system might send a notification (via one or more of a software application ("app"), a text message, a short message service ("SMS") message, a multimedia messaging service ("MMS") message, an e-mail message, or a chat message, and/or the like) to at least one of the user, the user's trainer, the user's physician or other medical professional, the notification indicating the determined physical condition or physiological status of the user or the determined probability that the user will suffer the physical condition. The user device associated with the at least one of the user, the user's trainer, the user's physician or other medical professional might receive the notification indicating the determined physical condition or physiological status of the user or the determined probability that the user will suffer the physical condition (block 474).

Assuming that it is determined that the user can recover from the determined existing physical condition or the determined likelihood of suffering from the physical condition, the computing system (at block 476) might send a remediation plan to the user (the remediation plan, in some cases, being reviewed by and/or designed by one or more of the user's trainer and/or the user's physician or other medical professional, or the like). The user device associated with the user might receive the remediation plan, which might include, without limitation, text descriptions of sets of motions, repetitions ("reps"), workout times, particular movement avoidance guidelines, and/or the like, image-based depictions of sets of motions, repetitions ("reps"), workout times, particular movement avoidance guidelines, and/or the like, video-based depictions of sets of motions, repetitions ("reps"), workout times, particular movement avoidance guidelines, and/or the like, or a combination of these descriptions/depictions. The process of method 400 might subsequently return to block 402 in FIG. 4A, following marker "F."

In some embodiments, the image or video-based capture of the views of the user might be performed first, and the image-based analysis (i.e., the process at blocks 406-476) might be performed later. Alternatively, the image-based analysis (i.e., the process at blocks 406-476) might be performed in real-time or near-real-time as the user is performing the one or more sets of motions and as the monitoring system is capturing the one or more views of the user as he or she is performing the one or more sets of motions.

Figure 5A:
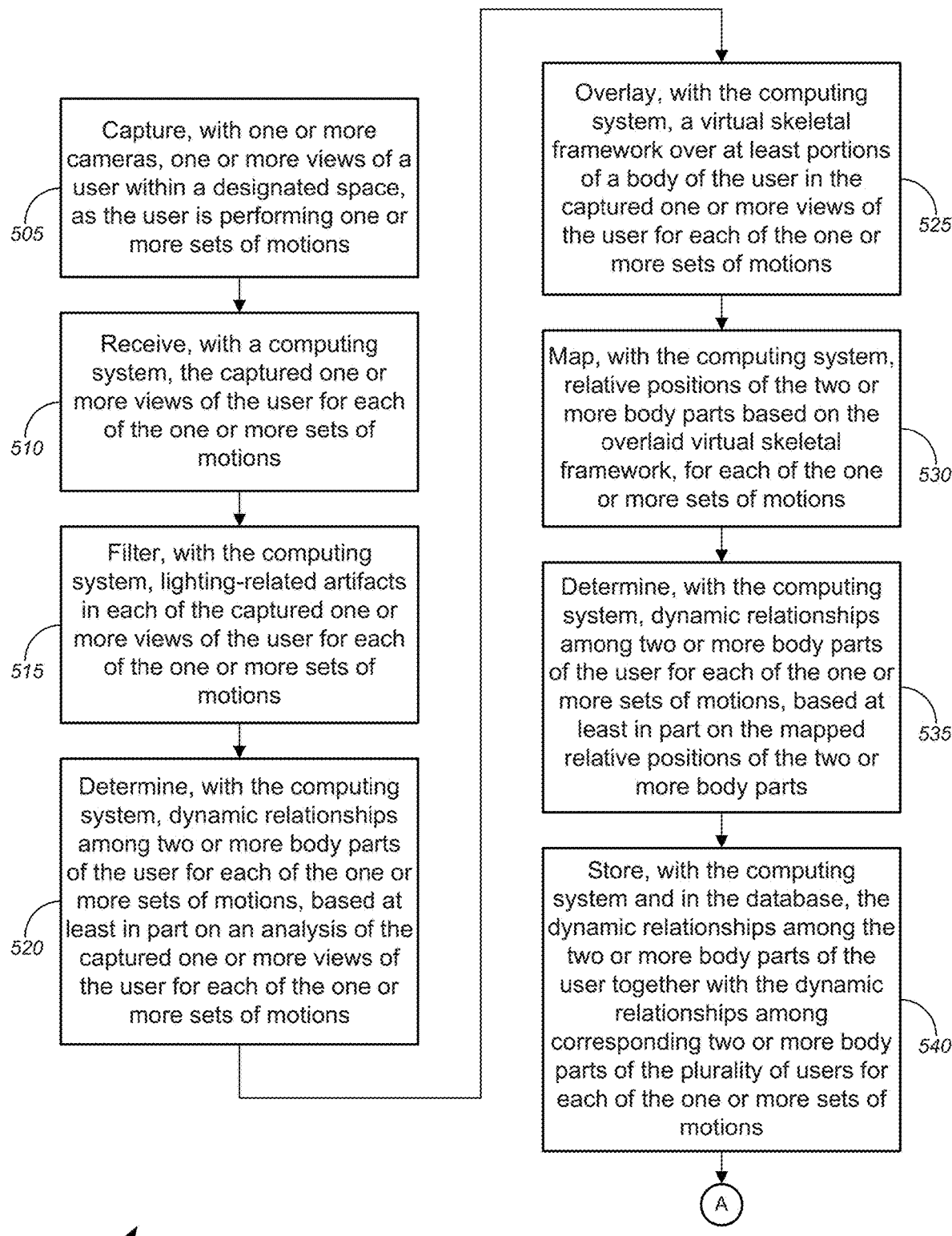
FIGS. 5A and 5B are flow diagrams illustrating another method for implementing image-based physiological status or physical condition determination of users and generating remediation plans as appropriate, in accordance with various embodiments.
Figure 5B:
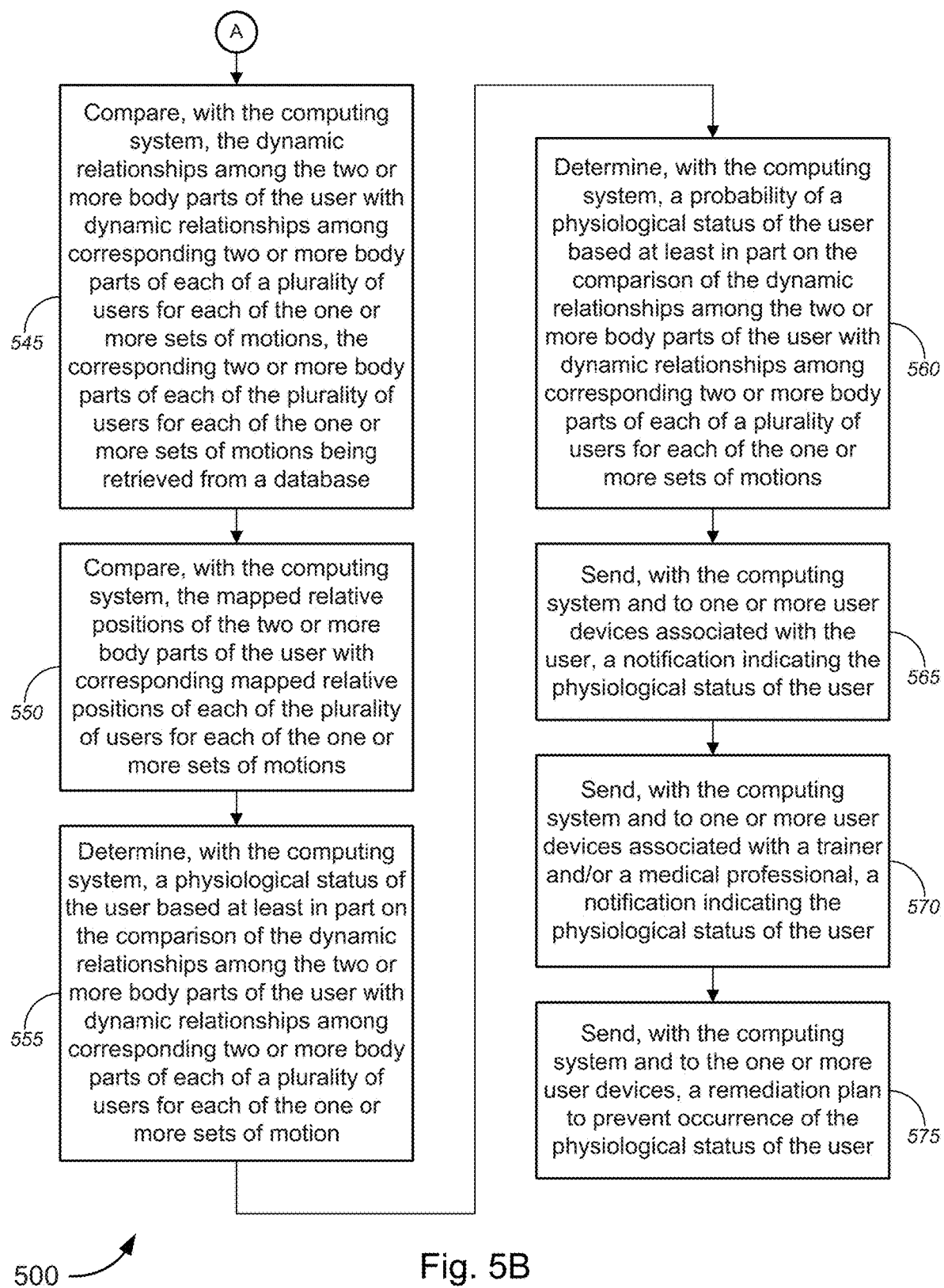

FIGS. 5A and 5B (collectively, "FIG. 5") are flow diagrams illustrating another method 500 for implementing image-based physiological status or physical condition determination of users and generating remediation plans as appropriate, in accordance with various embodiments. In FIG. 5, method 500 in FIG. 5A continues onto FIG. 5B, linked by the circular marker denoted by "A."

While the techniques and procedures of the method 500 is depicted and/or described in a certain order for purposes of illustration, it should be appreciated that certain procedures may be reordered and/or omitted within the scope of various embodiments. Moreover, while the method illustrated by FIG. 5 can be implemented by (and, in some cases, are described below with respect to) system 100 of FIG. 1 (or components thereof), system 200 of FIG. 2 (or components thereof), system 300 of FIG. 3 (or components thereof), the method may also be implemented using any suitable hardware implementation. Similarly, while system 100 (and/or components thereof), system 200 of FIG. 2 (or components thereof), system 300 of FIG. 3 (or components thereof), and/or the like can operate according to the method illustrated by FIG. 5 (e.g., by executing instructions embodied on a computer readable medium), systems 100, 200, and/or 300 can also operate according to other modes of operation and/or perform other suitable procedures.

With reference to FIG. 5A, method 500 might comprise, at block 505, capturing, with one or more cameras, one or more views of a user within a designated space, as the user is performing one or more sets of motions. In some embodiments, capturing one or more views of a user within a designated space, as the user is performing one or more sets of motions might comprise capturing, with one or more cameras, one or more views of a user within a designated space, as the user is performing one or more sets of motions using marker-less motion capture, or the like. According to some embodiments, the one or more cameras might comprise an array of cameras around the user within the designated space, and the one or more views of the user might comprise one or more perspective or elevation views of the user within the designated space. In some cases, the array of cameras might comprise an eight-camera array of cameras, while in other cases, the array of cameras might comprise a twelve-camera array of cameras. Of course, a person skilled in the art can appreciate that any suitable number of cameras (from one camera to more than twelve cameras) may be employed in the array of cameras, so long as all pertinent views of the user are captured to enable analysis or determination of the dynamic relationships among the two or more body parts of the user for each of the one or more sets of motions.

In some cases, the one or more cameras might comprise at least one of one or more stationary cameras, one or more cameras mounted on mechanical arms, one or more aerial drone-based cameras, or one or more ground-type drone-based cameras, and the like. In some instances, the designated space might be one of an indoor space, a man-made portable enclosure, and/or an outdoor space, or the like. In some embodiments (particularly in outdoor settings, although also applicable to indoor settings or portable enclosure settings, or the like), the method might further comprise filtering, with the computing system, lighting-related artifacts in each of the captured one or more views of the user for each of the one or more sets of motions, prior to determining dynamic relationships among the two or more body parts of the user for each of the one or more sets of motions. According to some embodiments, the designated space might be one of a sports stadium, an athletic field, an ice rink, a ski slope, a trail, a roadway, or a pathway, and/or the like.

In some instances, the computing system might be located proximal to the designated space. Alternatively, the computing system might be located at a remote location relative to the designated space, and receiving the captured one or more views of the user for each of the one or more sets of motions might comprise receiving, with a computing system, the captured one or more views of the user for each of the one or more sets of motions via a network.

Method 500 might further comprise receiving, with a computing system, the captured one or more views of the user for each of the one or more sets of motions (block 510). Method 500, at block 515, might comprise filtering, with the computing system, lighting-related artifacts in each of the captured one or more views of the user for each of the one or more sets of motions.

At block 520, method 500 might comprise determining, with the computing system, dynamic relationships among two or more body parts of the user for each of the one or more sets of motions, based at least in part on an analysis of the captured one or more views of the user for each of the one or more sets of motions. Merely by way of example, in some cases, the two or more body parts of the user might comprise at least two of one or more toes, at least one ankle, at least one knee, at least one hip, at least one shoulder, at least one elbow, at least one wrist, one or more fingers, a neck, or a skull of the user, and/or the like.

In some embodiments, determining dynamic relationships among two or more body parts of the user for each of the one or more sets of motions might comprise overlaying, with the computing system, a virtual skeletal framework over at least portions of a body of the user in the captured one or more views of the user for each of the one or more sets of motions (block 525), mapping, with the computing system, relative positions of the two or more body parts based on the overlaid virtual skeletal framework, for each of the one or more sets of motions (block 530), and determining, with the computing system, dynamic relationships among two or more body parts of the user for each of the one or more sets of motions, based at least in part on the mapped relative positions of the two or more body parts (block 535).

Method 500, at block 540, might comprise storing, with the computing system and in the database, the dynamic relationships among the two or more body parts of the user together with the dynamic relationships among corresponding two or more body parts of the plurality of users for each of the one or more sets of motions. In some cases, retrieving or storing the dynamic relationships among the two or more body parts of each of the user and the plurality of users from or in the database might be performed over a network The process in method 500 then continues to block 545 in FIG. 5B following marker "A."

At block 545, in FIG. 5B, method 500 might comprise comparing, with the computing system, the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database. In some embodiments, comparing the dynamic relationships among the two or more body parts of the user with dynamic relationships among corresponding two or more body parts of each of a plurality of users for each of the one or more sets of motions might comprise comparing, with the computing system, the dynamic relationships among the two or more body parts of the user with dynamic relationships among corresponding two or more body parts of each of a plurality of users for each of the one or more sets of motions by comparing the mapped relative positions of the two or more body parts of the user with corresponding mapped relative positions of each of the plurality of users for each of the one or more sets of motions (block 550). As described above, such analysis might include, without limitation, comparing the captured images of the user performing the set of motions (in some cases, comparing the dynamic relationships among the two or more body parts of the user, which, in some instances, might include the skeletal overlay) with baseline captured images of the same user performing the same set of motions (in some cases, comparing with the dynamic relationships among the two or more body parts of the user, which, in some instances, might include the skeletal overlay) and/or in comparison with captured images of each of a plurality of users performing the same set of motions (in some cases, comparing with the dynamic relationships among the two or more body parts of each of the plurality of users, which, in some instances, might include the skeletal overlay)—that is, comparing captured images of the same motion (at particular points in the motion) as performed by each of the user (at the current or latest time), the user (during the baseline phase), and a plurality of users, and repeating for each frame of the images corresponding to the same particular points in each motion.

Method 500 might further comprise, at block 555, determining, with the computing system, a physiological status of the user based at least in part on the comparison of the dynamic relationships among the two or more body parts of the user with dynamic relationships among corresponding two or more body parts of each of a plurality of users for each of the one or more sets of motions. In some instances, the physiological status of user might be a physiological status (or a physical condition) selected from a group consisting of a concussion, a torn anterior cruciate ligament ("ACL"), a torn posterior cruciate ligament ("PCL"), a torn medial collateral ligament ("MCL"), a torn lateral collateral ligament ("LCL"), an ankle sprain, a groin pull, a hamstring strain, shin splints, and tennis elbow, and/or the like. According to some embodiments, determining a physiological status of the user comprises determining, with the computing system, a probability of a physiological status of the user based at least in part on the comparison of the dynamic relationships among the two or more body parts of the user with dynamic relationships among corresponding two or more body parts of each of a plurality of users for each of the one or more sets of motions (block 560).

Merely by way of example, in some embodiments, method 500 might further comprise sending, with the computing system and to one or more user devices associated with the user, a notification indicating at least one of the physiological status of the user, the physical condition of the user, and/or a probability that the user will suffer the physical condition if a remediation plan is not implemented, and/or the like (block 565). Alternatively, or additionally, method 500 might further comprise sending, with the computing system and to one or more user devices associated with one or more of the user's trainer(s) and/or the user's physician or other medical professional, a notification indicating at least one of the physiological status of the user, the physical condition of the user, and/or a probability that the user will suffer the physical condition if a remediation plan is not implemented, and/or the like (block 570). At block 575, method 500 might comprise sending, with the computing system and to one or more user devices (associated with the user), a remediation plan to prevent occurrence of the physiological status or physical condition of the user. According to some embodiments, each of these notifications may be sent via a software application ("app") for display in a graphical user interface ("GUI") of the software app. Alternatively, or additionally, each of these notifications may be sent via at least one of a text message, a short message service ("SMS") message, a multimedia messaging service ("MMS") message, an e-mail message, or a chat message. The one or more user devices might comprise at least one of a smart phone, a mobile phone, a personal digital assistant, a tablet computer, a laptop computer, a desktop computer, a server computer, and/or the like.

Figure 6C:
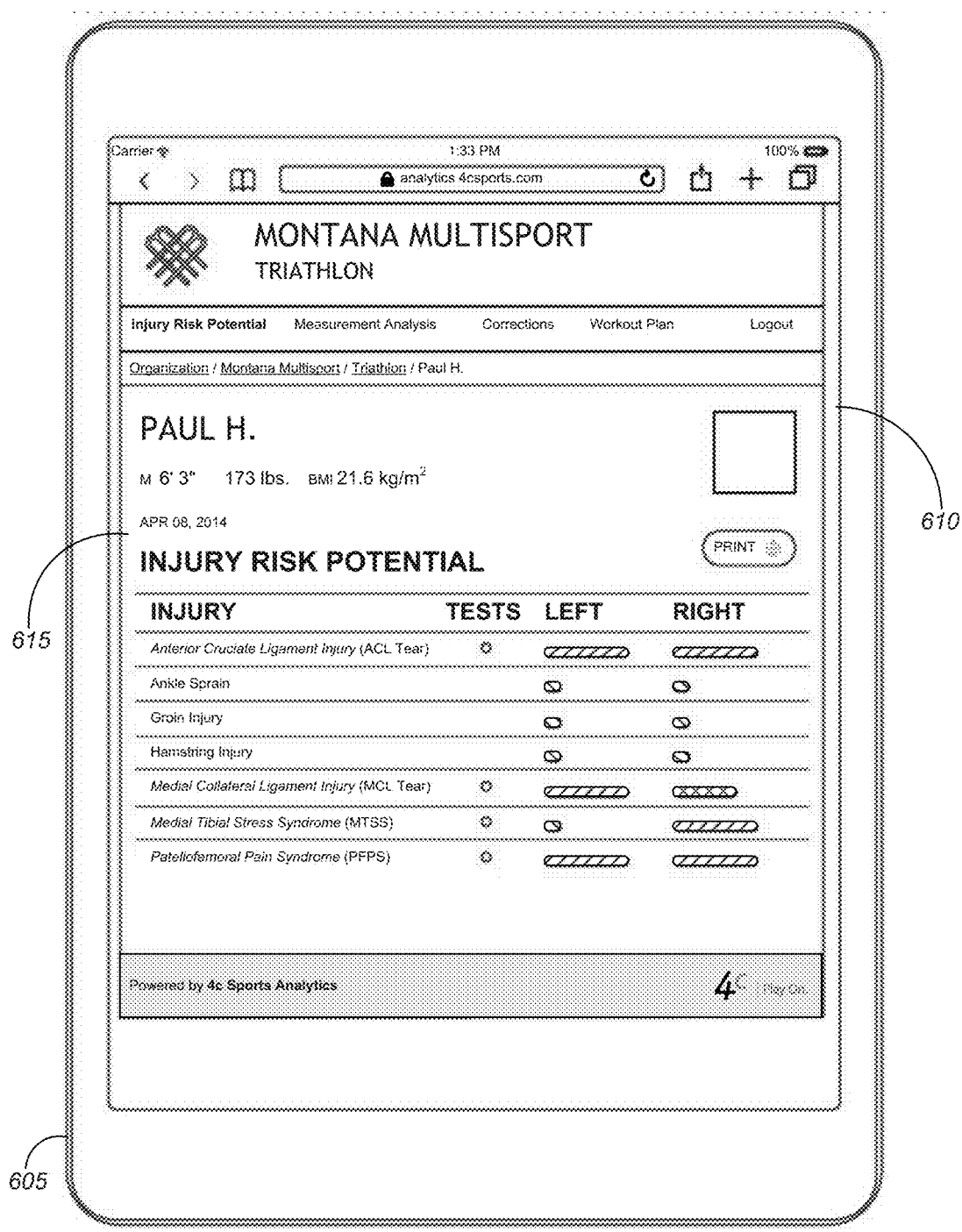
Figure 6D:
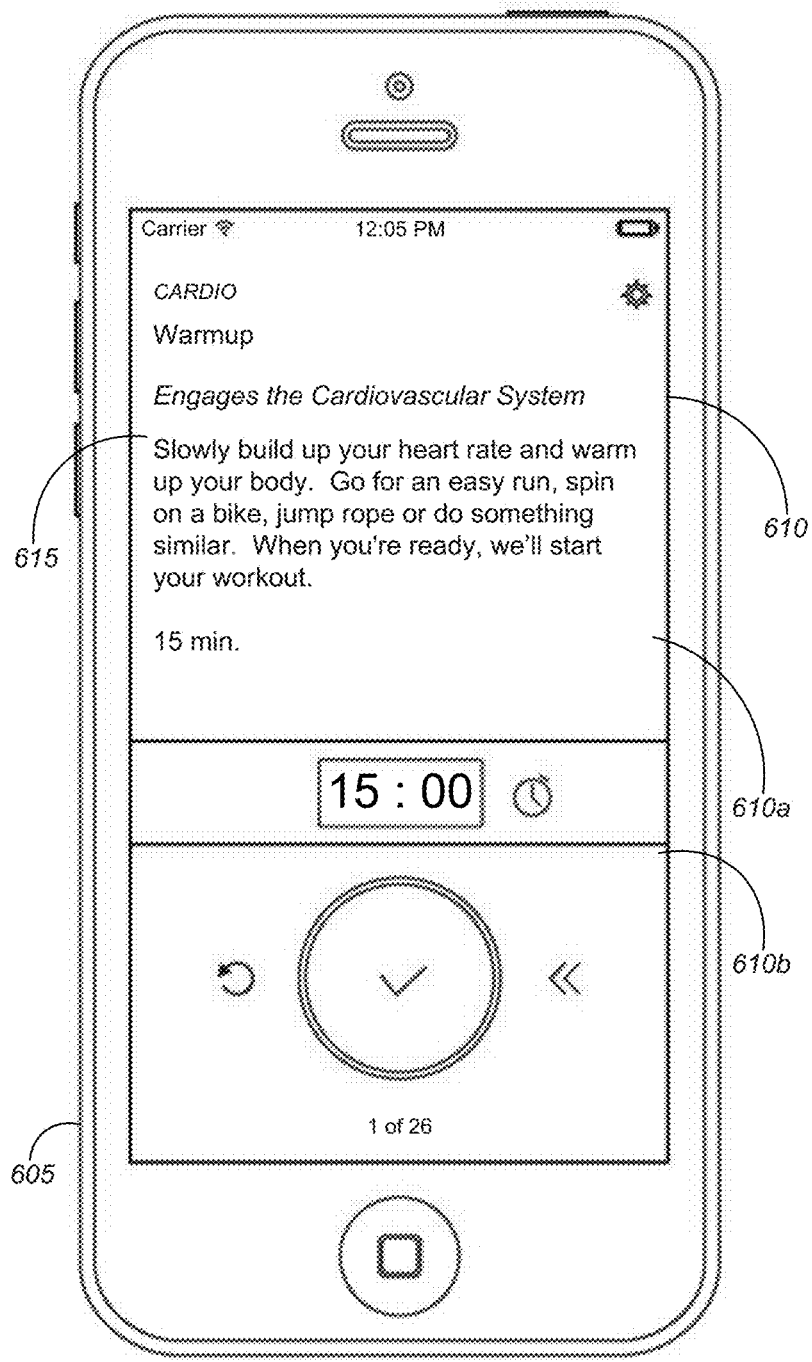

FIGS. 6A-6D (collectively, "FIG. 6") illustrate example user interfaces and notifications that a user, a trainer of the user, or the user's physician or other medical professional might interact with or receive on his or her user device 600, in accordance with various embodiments. FIGS. 6A-6C depict embodiments in which the notification of the results of the image-based physical condition evaluation is sent to the user (FIG. 6A), the notification of the results of the image-based physical condition evaluation is sent to the user's physician or other medical professional (FIG. 6B), and the notification of injury risk potential is sent to the user (FIG. 6C). FIG. 6D depicts an embodiment in which a remediation plan is sent to the user (with an app allowing for ease of implementation and tracking of the user's efforts in implementing the remediation plan).

In FIG. 6A, user device 600 (in this case, a smart phone, although not limited to such) might comprise a housing 605 and a display screen 610 (which might be a touchscreen display). The display screen 610 might display a first panel 610a that displays the notification message 615, and might display a second panel 610b that displays icons for activating functions of the user device 600 (e.g., menu, back, home, phone, and search functionalities of the smart phone, for example).

In FIG. 6B, user device 600 (in this case, a monitor of a computing device, although not limited to such) might comprise a housing 605 and a display screen 610 (which might be a touchscreen display or a non-touchscreen display). The display screen 610 might display a panel or window 610a that displays the notification message 615.

In FIG. 6C, user device 600 (in this case, a tablet computer) might comprise a housing 605 and a display screen 610 (which might be a touchscreen display or a non-touchscreen display). The display screen 610 might display a panel or window 610a that displays the notification message 615. In this embodiments, the user device 600 might display the injury risk potential, either in an app screen or a web-based portal, or the like. The bars under the "LEFT" and "RIGHT" columns (which indicate the side of the body of the user) indicate the injury risk potential for the user, with the longer bars indicating greater risk than the shorter bars for each of the potential injuries listed in the "INJURY" column, where the injury risk potentials are identified (where applicable) for injuries that are tested (as indicated by the circular markings under the "TESTS" column).

In FIG. 6D, a user device 600 (in this case, a smart phone) might comprise a housing 605 and a display screen 610 (which might be a touchscreen display or a non-touchscreen display). The display screen 610 might display a panel or window 610a that displays the notification message 615. In this embodiment, the user device 600 might display a remediation plan, which might be displayed in an app or the like (in some cases, in a first panel or window 610a, or the like), with clock, check-list, or other functionalities to facilitate implementation by the user of the remediation plan being displayed in a second and/or third panel or window 610b, or the like.

Exemplary System and Hardware Implementation

Figure 7:
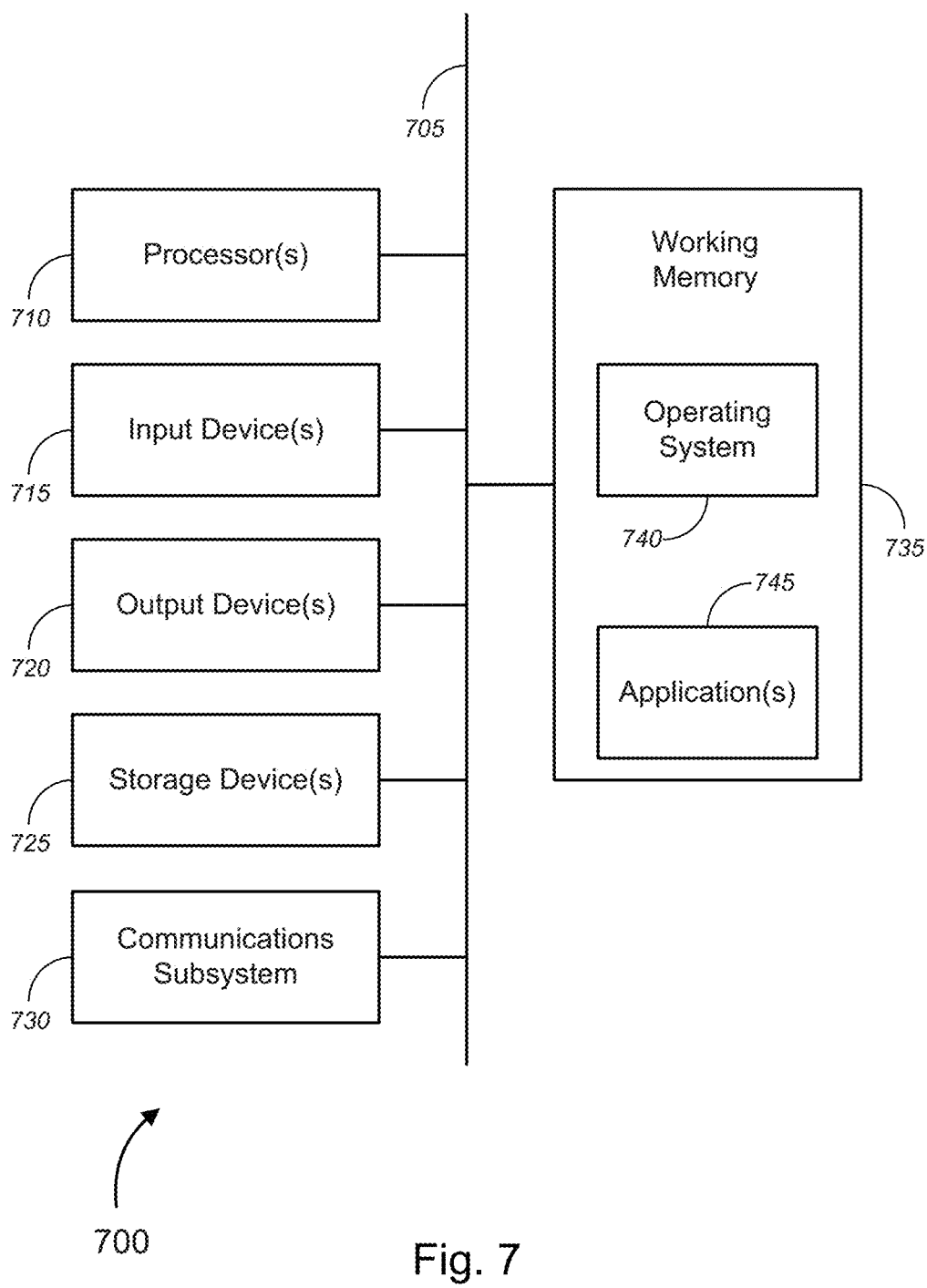
FIG. 7 is a block diagram illustrating an exemplary computer or system hardware architecture, in accordance with various embodiments.

FIG. 7 is a block diagram illustrating an exemplary computer or system hardware architecture, in accordance with various embodiments. FIG. 7 provides a schematic illustration of one embodiment of a computer system 700 of the service provider system hardware that can perform the methods provided by various other embodiments, as described herein, and/or can perform the functions of computer or hardware system (i.e., monitoring system 120, computing system 130, user device(s) 140, user device(s) 150, and/or user device(s) 160, as described above). It should be noted that FIG. 7 is meant only to provide a generalized illustration of various components, of which one or more (or none) of each may be utilized as appropriate. FIG. 7, therefore, broadly illustrates how individual system elements may be implemented in a relatively separated or relatively more integrated manner.

The computer or hardware system 700—which might represent an embodiment of the computer or hardware system (i.e., monitoring system 120, computing system 130, user device(s) 140, user device(s) 150, and/or user device(s) 160, as described above with respect to FIGS. 1-6)—is shown comprising hardware elements that can be electrically coupled via a bus 705 (or may otherwise be in communication, as appropriate). The hardware elements may include one or more processors 710, including, without limitation, one or more general-purpose processors and/or one or more special-purpose processors (such as digital signal processing chips, graphics acceleration processors, and/or the like); one or more input devices 715, which can include, without limitation, a mouse, a keyboard and/or the like; and one or more output devices 720, which can include, without limitation, a display device, a printer, and/or the like.

The computer or hardware system 700 may further include (and/or be in communication with) one or more storage devices 725, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including, without limitation, various file systems, database structures, and/or the like.

The computer or hardware system 700 might also include a communications subsystem 730, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 730 may permit data to be exchanged with a network (such as the network described below, to name one example), with other computer or hardware systems, and/or with any other devices described herein. In many embodiments, the computer or hardware system 700 will further comprise a working memory 735, which can include a RAM or ROM device, as described above.

The computer or hardware system 700 also may comprise software elements, shown as being currently located within the working memory 735, including an operating system 740, device drivers, executable libraries, and/or other code, such as one or more application programs 745, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 725 described above. In some cases, the storage medium might be incorporated within a computer system, such as the system 700. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer or hardware system 700 and/or might take the form of source and/or installable code, which, upon compilation and/or installation on the computer or hardware system 700 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 700) to perform methods in accordance with various embodiments of the invention. According to a set of embodiments, some or all of the procedures of such methods are performed by the computer or hardware system 700 in response to processor 710 executing one or more sequences of one or more instructions (which might be incorporated into the operating system 740 and/or other code, such as an application program 745) contained in the working memory 735. Such instructions may be read into the working memory 735 from another computer readable medium, such as one or more of the storage device(s) 725. Merely by way of example, execution of the sequences of instructions contained in the working memory 735 might cause the processor(s) 710 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 700, various computer readable media might be involved in providing instructions/code to processor(s) 710 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 725. Volatile media includes, without limitation, dynamic memory, such as the working memory 735. In some alternative embodiments, a computer readable medium may take the form of transmission media, which includes, without limitation, coaxial cables, copper wire and fiber optics, including the wires that comprise the bus 705, as well as the various components of the communication subsystem 730 (and/or the media by which the communications subsystem 730 provides communication with other devices). In an alternative set of embodiments, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 710 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 700. These signals, which might be in the form of electromagnetic signals, acoustic signals, optical signals, and/or the like, are all examples of carrier waves on which instructions can be encoded, in accordance with various embodiments of the invention.

The communications subsystem 730 (and/or components thereof) generally will receive the signals, and the bus 705 then might carry the signals (and/or the data, instructions, etc. carried by the signals) to the working memory 735, from which the processor(s) 705 retrieves and executes the instructions. The instructions received by the working memory 735 may optionally be stored on a storage device 725 either before or after execution by the processor(s) 710.

Figure 8:
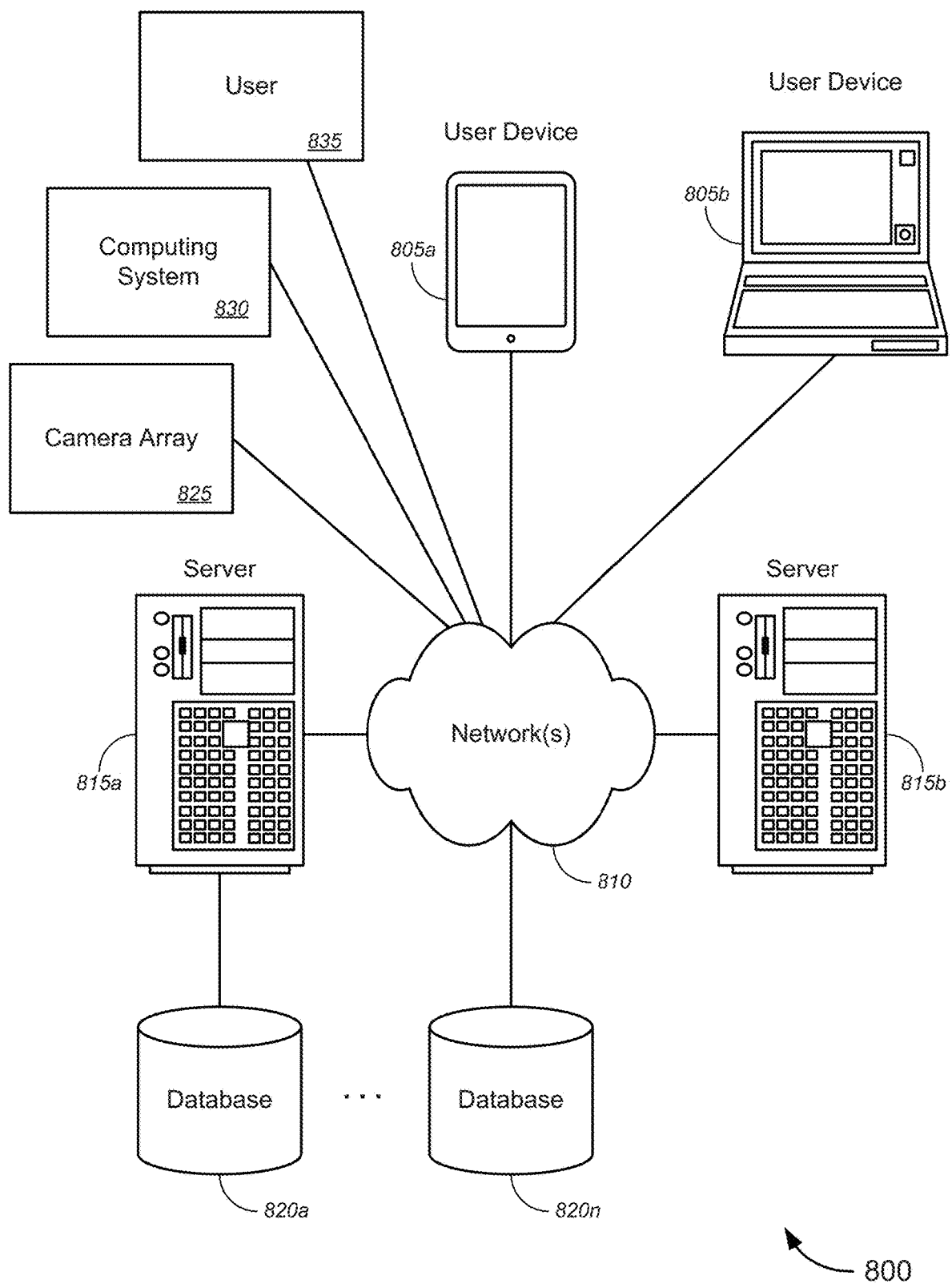
FIG. 8 is a block diagram illustrating a networked system of computers, computing systems, or system hardware architecture, which can be used in accordance with various embodiments.

As noted above, a set of embodiments comprises methods and systems for implementing image-based physiological status determination of users, and, in particular embodiments, for implementing physiological status determination of users based on marker-less motion-capture and generating remediation plans as appropriate. FIG. 8 illustrates a schematic diagram of a system 800 that can be used in accordance with one set of embodiments. The system 800 can include one or more user computers, user devices, or customer devices 805. A user computer, user device, or customer device 805 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 805 can also have any of a variety of applications, including one or more applications configured to perform methods provided by various embodiments (as described above, for example), as well as one or more office applications, database client and/or server applications, and/or web browser applications. Alternatively, a user computer, user device, or customer device 805 can be any other electronic device, such as a thin-client computer, Internet-enabled mobile telephone, and/or personal digital assistant, capable of communicating via a network (e.g., the network(s) 810 described below) and/or of displaying and navigating web pages or other types of electronic documents. Although the exemplary system 800 is shown with two user computers, user devices, or customer devices 805a and 805b, any number of user computers, user devices, or customer devices can be supported.

Certain embodiments operate in a networked environment, which can include a network(s) 810. The network(s) 810 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 810 can each include a local area network ("LAN"), including, without limitation, a fiber network, an Ethernet network, a Token-Ring™ network and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 815. Each of the server computers 815 may be configured with an operating system, including, without limitation, any of those discussed above, as well as any commercially (or freely) available server operating systems. Each of the servers 815 may also be running one or more applications, which can be configured to provide services to one or more clients 805 and/or other servers 815.

Merely by way of example, one of the servers 815 might be a data server, a web server, a cloud computing device(s), or the like, as described above. The data server might include (or be in communication with) a web server, which can be used, merely by way of example, to process requests for web pages or other electronic documents from user computers 805. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 805 to perform methods of the invention.

The server computers 815, in some embodiments, might include one or more application servers, which can be configured with one or more applications accessible by a client running on one or more of the client computers 805 and/or other servers 815. Merely by way of example, the server(s) 815 can be one or more general purpose computers capable of executing programs or scripts in response to the user computers 805 and/or other servers 815, including, without limitation, web applications (which might, in some cases, be configured to perform methods provided by various embodiments). Merely by way of example, a web application can be implemented as one or more scripts or programs written in any suitable programming language, such as Java™, C, C #™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 805 and/or another server 815. In some embodiments, an application server can perform one or more of the processes for implementing image-based physiological status determination of users, and, in particular embodiments, for implementing physiological status determination of users based on marker-less motion-capture and generating remediation plans as appropriate, or the like, as described in detail above. Data provided by an application server may be formatted as one or more web pages (comprising HTML, JavaScript, etc., for example) and/or may be forwarded to a user computer 805 via a web server (as described above, for example). Similarly, a web server might receive web page requests and/or input data from a user computer 805 and/or forward the web page requests and/or input data to an application server. In some cases, a web server may be integrated with an application server.

In accordance with further embodiments, one or more servers 815 can function as a file server and/or can include one or more of the files (e.g., application code, data files, etc.) necessary to implement various disclosed methods, incorporated by an application running on a user computer 805 and/or another server 815. Alternatively, as those skilled in the art will appreciate, a file server can include all necessary files, allowing such an application to be invoked remotely by a user computer, user device, or customer device 805 and/or server 815.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 820a-820n (collectively, "databases 820"). The location of each of the databases 820 is discretionary: merely by way of example, a database 820a might reside on a storage medium local to (and/or resident in) a server 815a (and/or a user computer, user device, or customer device 805). Alternatively, a database 820n can be remote from any or all of the computers 805, 815, so long as it can be in communication (e.g., via the network 810) with one or more of these. In a particular set of embodiments, a database 820 can reside in a storage-area network ("SAN") familiar to those skilled in the art. (Likewise, any necessary files for performing the functions attributed to the computers 805, 815 can be stored locally on the respective computer and/or remotely, as appropriate.) In one set of embodiments, the database 820 can be a relational database, such as an Oracle database, that is adapted to store, update, and retrieve data in response to SQL-formatted commands. The database might be controlled and/or maintained by a database server, as described above, for example.

According to some embodiments, system 800 might further comprise a camera array 825 (similar to the array of cameras 115 as shown in FIGS. 1-3, or the like), a computing system(s) 830 (similar to computing system 130 of FIG. 1, or the like), and/or a user 835, as described in detail above with respect to FIGS. 1-6. In some embodiments, the computing system(s) 830 might be embodied by, or might have functionalities similar to those of, servers 815a or 815b.

Examples of Tests for Determining Particular Physical Conditions

We now turn to various embodiments for determining particular physical conditions or determining probability that a user might suffer particular physical conditions (e.g., potential risk injuries, actual injuries, etc.), based at least in part on analysis of image-captured views of the user as the user is performing particular sets of motions (herein referred to as "tests" or "test sets" or "motion tests").

Figures 9A, 9B:
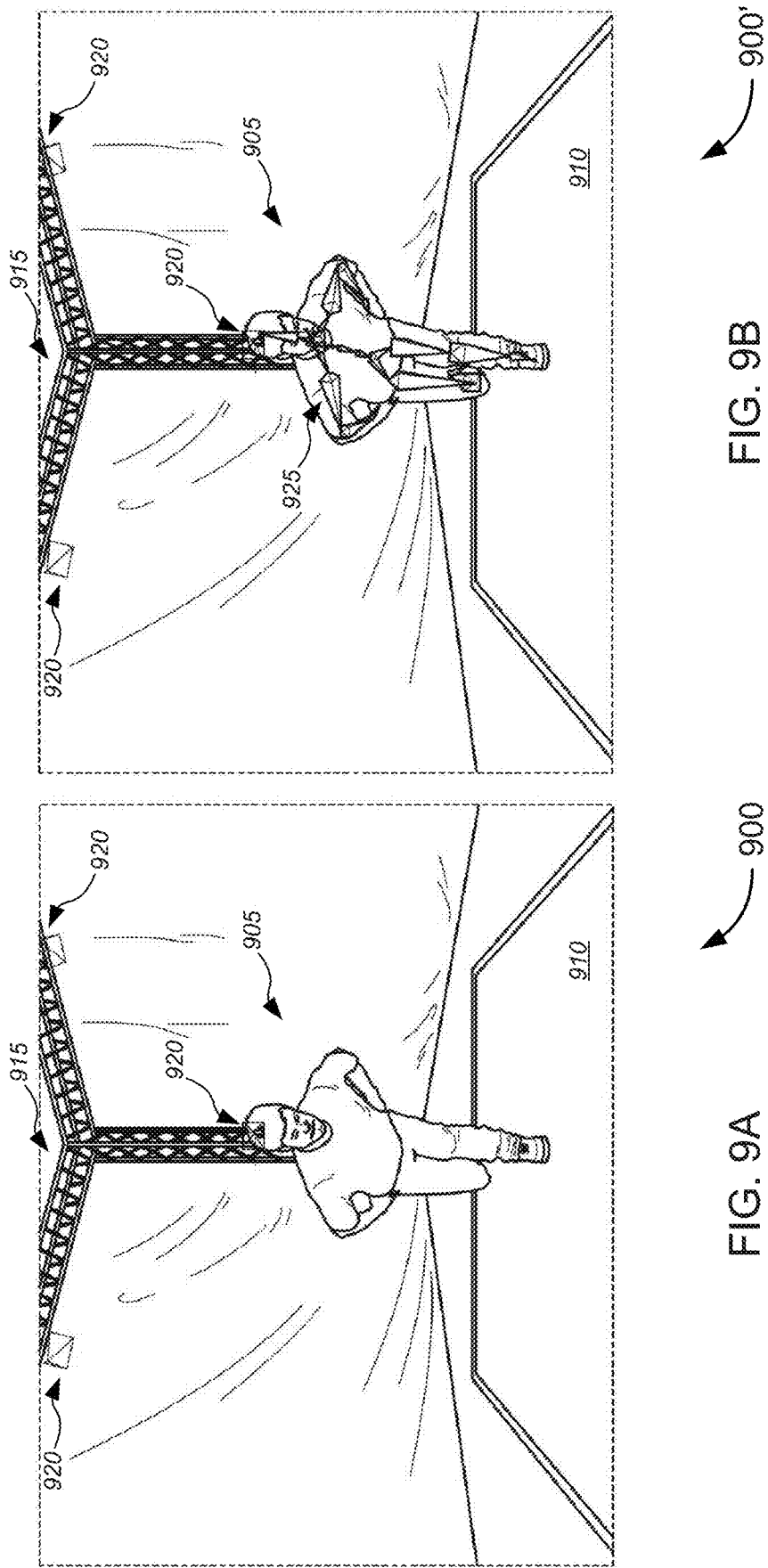
FIGS. 9A-9S illustrate an example system configuration and test for diagnosing potential one or more biomechanical-type injuries in a first user, in accordance with various embodiments.
Figures 9C, 9D:
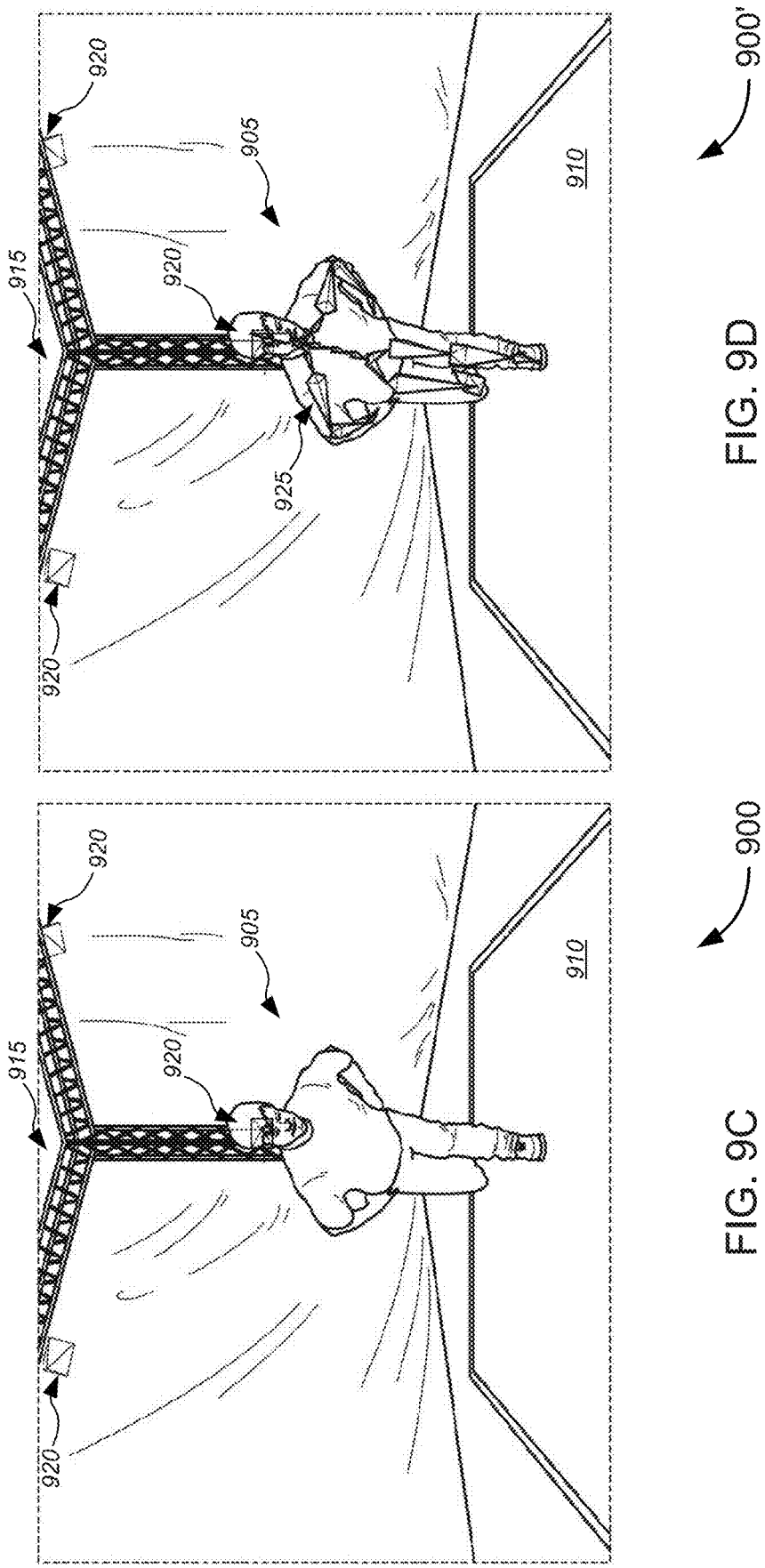
Figure 9H:
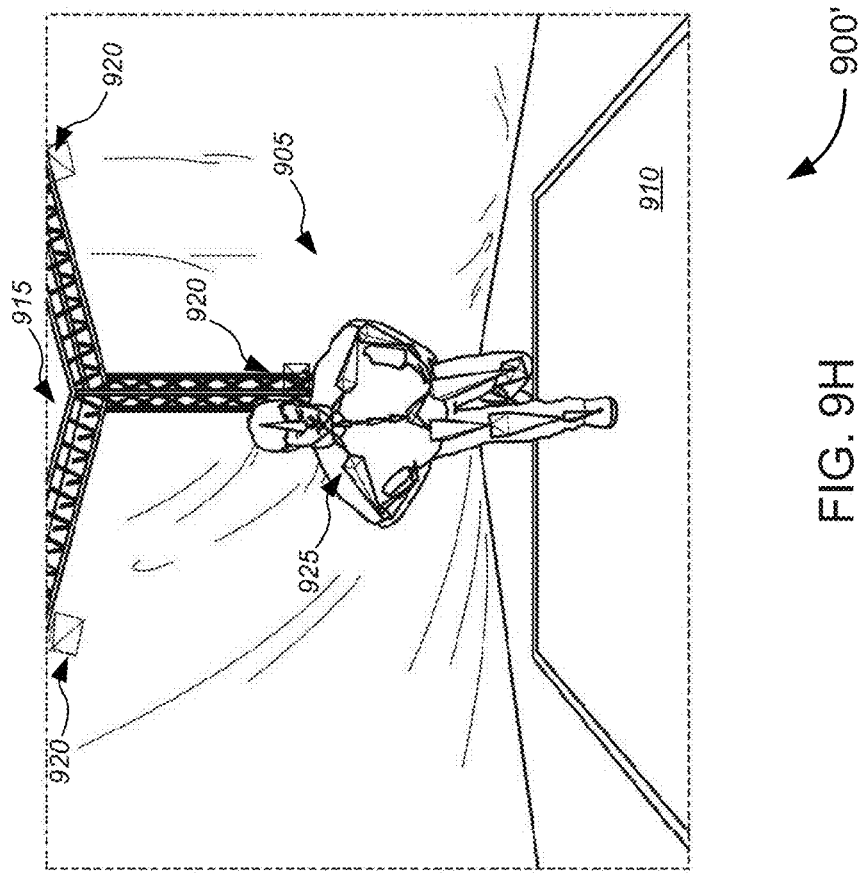
Figure 9G:
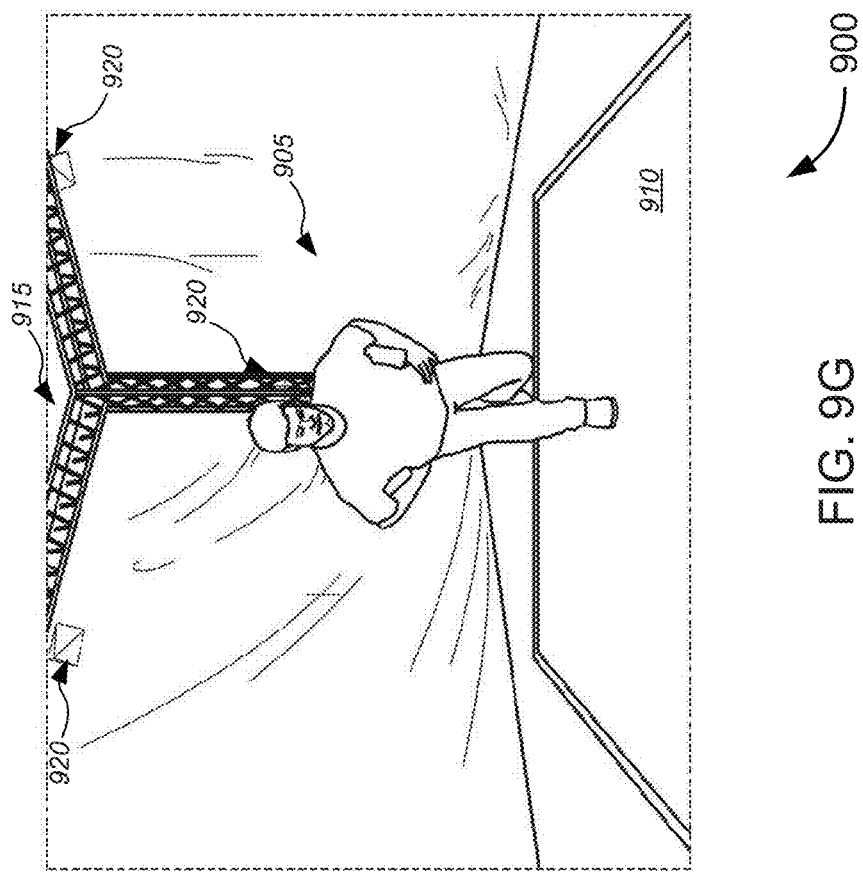
Figure 9S:
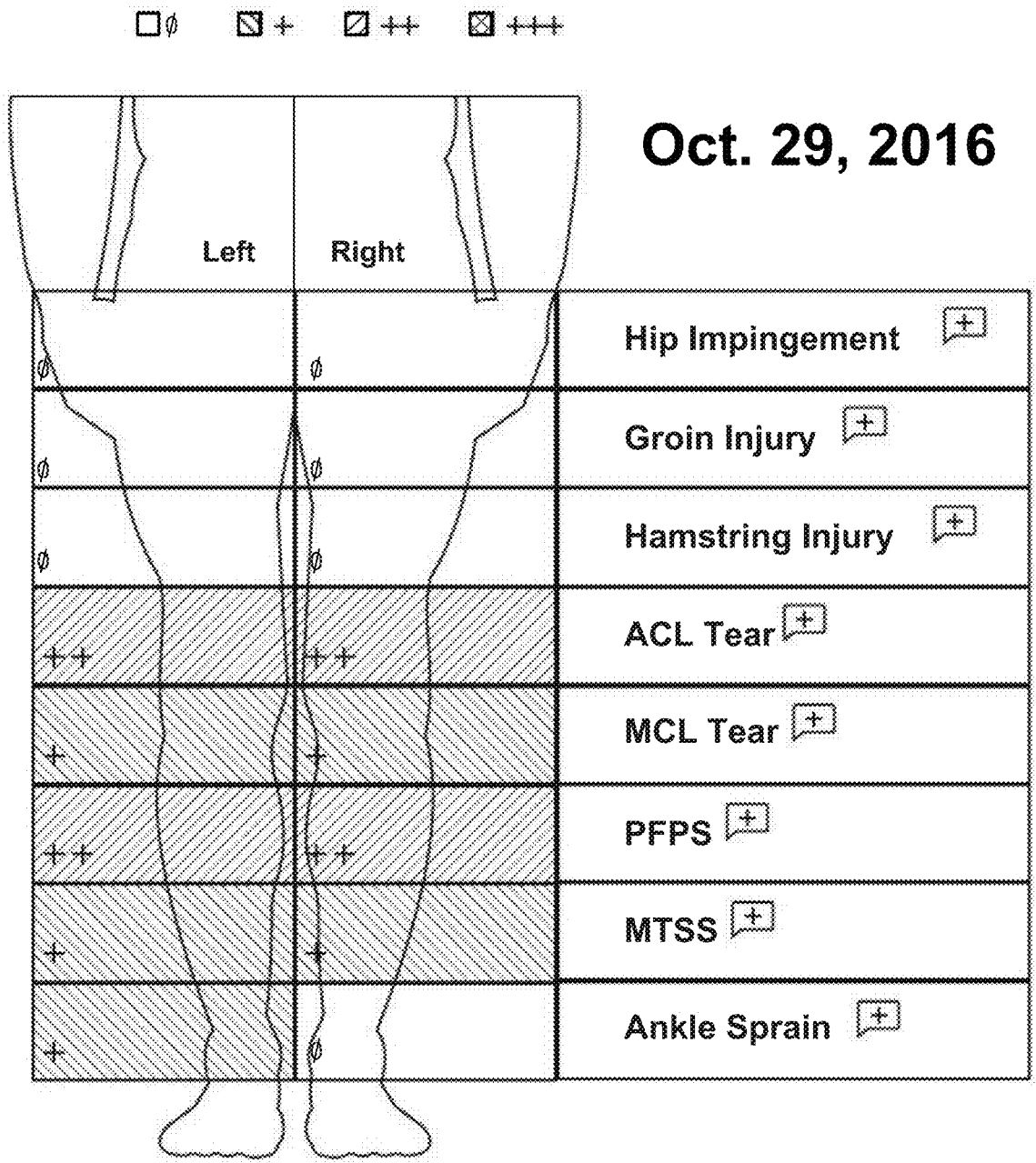

FIGS. 9A-9S (collectively, "FIG. 9") illustrate an example system configuration and test for diagnosing potential one or more biomechanical-type injuries in a first user, in accordance with various embodiments. FIG. 9 depicts a plurality of screenshots of images that are captured of a user performing a set of motions in accordance with the test for diagnosing potential one or more biomechanical-type injuries in accordance with the various embodiments. As shown in FIG. 9, the test might include a set of motions, including, but not limited to, a left leg squat (as shown in FIGS. 9A-9F), a right leg squat (as shown in FIGS. 9G-9L), two-legged squat (as shown in FIGS. 9M-9R), and/or the like. The motions to test for biomechanical injuries may, in some embodiments, be set in the order as listed above. Alternatively, the motions to test for biomechanical injuries may be made in any order. In yet other embodiments, the motions to test for biomechanical injuries may be randomized in terms of performance order, and the user performing such motions may be asked to do so according to the randomized order or randomized list of motions. In FIG. 9, screenshots 900 (i.e., in FIGS. 9A, 9C, 9E, 9G, 9I, 9K, 9M, 9O, and 9Q) depict user 905, on a mat 910, both positioned within enclosure 915 (a portion of which is shown in FIG. 9), with cameras mounted on the enclosure 915 (the fields of view 920 of some of the cameras being digitally overlaid on top of the captured images/video of the user 905 within the enclosure 915). Screenshots 900' (i.e., in FIGS. 9B, 9D, 9F, 9H, 9J, 9L, 9N, and 9P) further depict a skeletal framework overlay 925 being digitally overlaid over the images/video of the user 905, as the user 905 performs the motions described above.

In accordance with the methods described above (e.g., with respect to method 400 of FIG. 4 or method 500 of FIG. 5, or the like), the system can determine, based on comparisons of the dynamic relationships among two or more body parts of the user with dynamic relationships among corresponding two or more body parts of each of a plurality of users for each of the sets of motions and/or based on comparisons of the mapped relative positions of the two or more body parts of the user with corresponding mapped relative positions of each of the plurality of users for each of the one or more sets of motions, a physiological status of the user and/or a probability of a physiological status of the user. FIG. 9S is a screenshot 900" that depicts a summary of the determination of a physiological status or a probability of a physiological status (in this case, embodied as relative injury risk potential, although not limited to such). In particular, FIG. 9S shows that for the first user 905 whose motions are captured and analyzed in FIGS. 9A-9R, there is little or no risk of hip impingement, groin injury, hamstring injury, or right ankle sprain. However, the first user has a low risk of a torn medial collateral ligament ("MCL") in each knee, medial tibial stress syndrome ("MTSS") in each leg, and a left ankle sprain (as denoted by the "+" blocks), as well as a medium risk of a torn anterior cruciate ligament ("ACL") in each knee and patellofemoral pain syndrome ("PFPS") in each leg (as denoted by the "++" blocks).

Figure 10D:
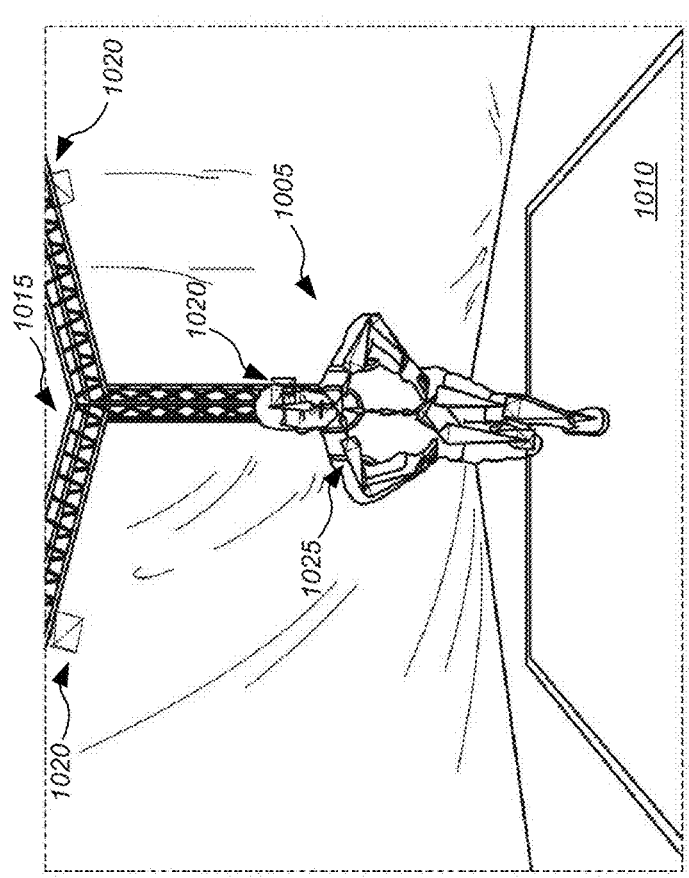
FIGS. 10A-10S illustrate the example system configuration and test for diagnosing potential one or more biomechanical-type injuries in a second user, in accordance with various embodiments.
Figure 10C:
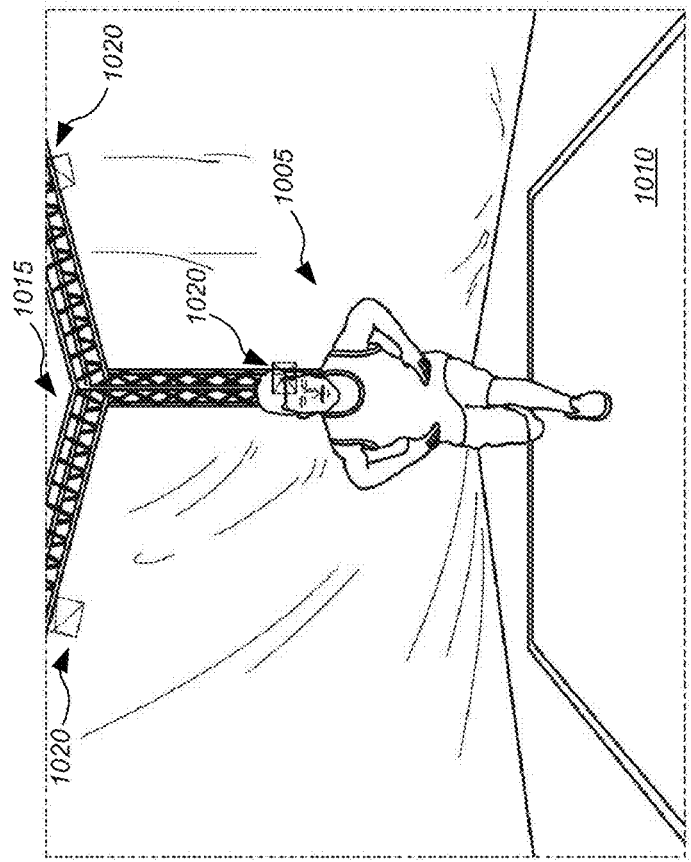
Figure 10J:
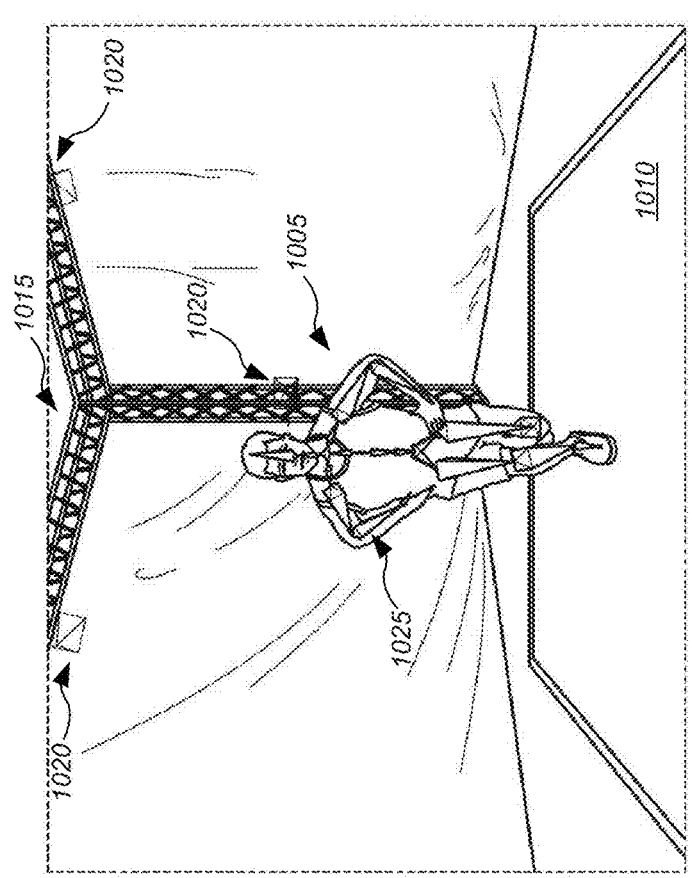
Figure 10I:
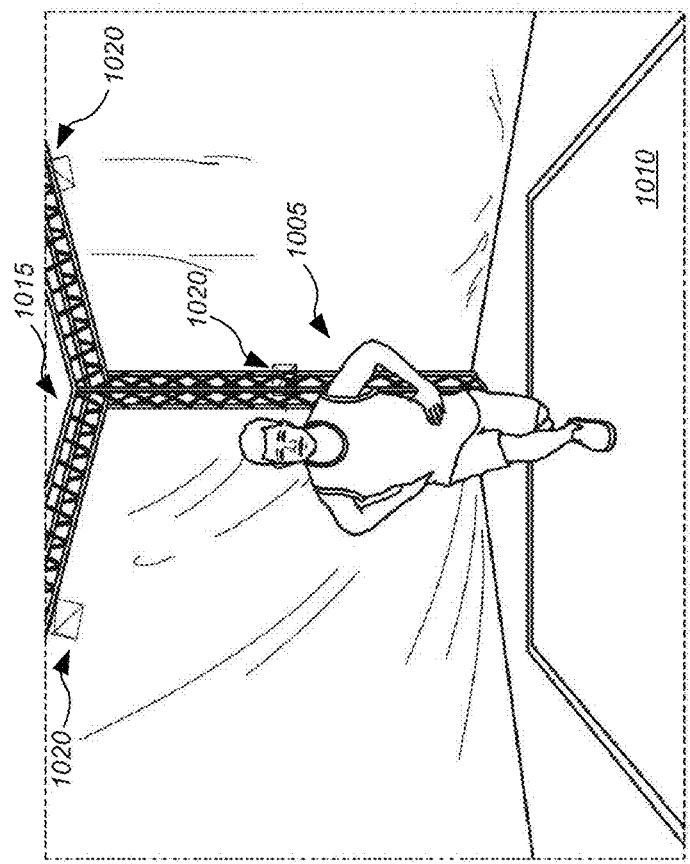
Figure 10Q:
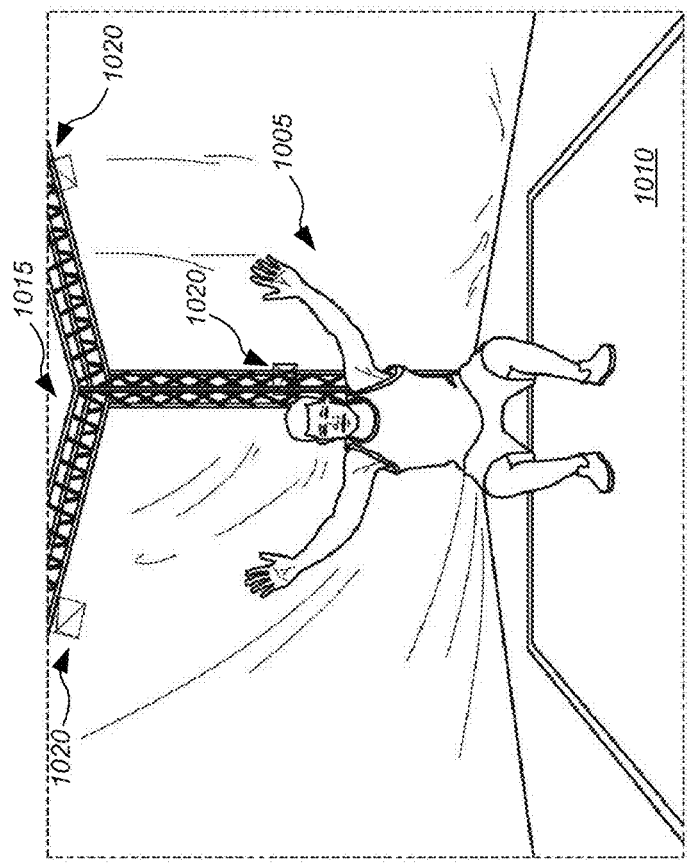
Figure 10R:
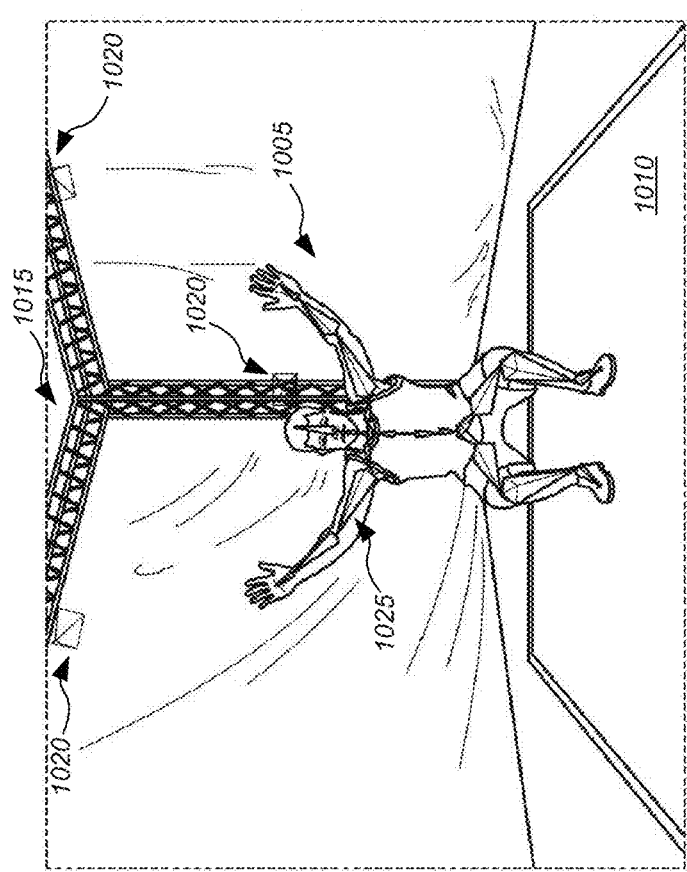
Figure 10S:
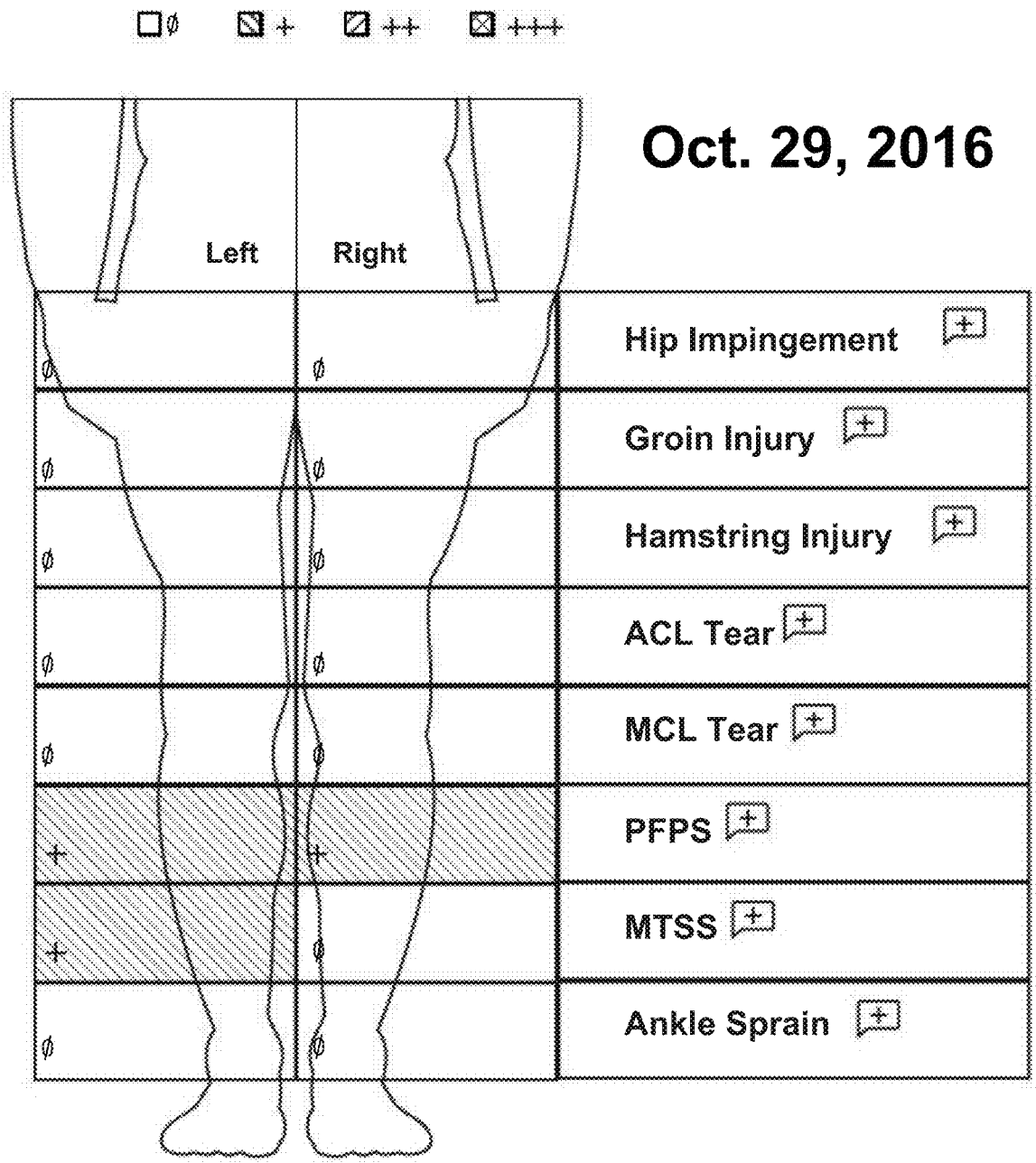

FIGS. 10A-10S (collectively, "FIG. 10") illustrate an example system configuration and test for diagnosing potential one or more biomechanical-type injuries in a second user, in accordance with various embodiments. FIG. 10 depicts a plurality of screenshots of images that are captured of a user performing a set of motions in accordance with the test for diagnosing potential one or more biomechanical-type injuries in accordance with the various embodiments. As shown in FIG. 10, the test might include a set of motions, including, without limitation, a left leg squat (as shown in FIGS. 10A-10F), a right leg squat (as shown in FIGS. 10G-10L), two-legged squat (as shown in FIGS. 10M-10R), and/or the like. The motions to test for biomechanical injuries may, in some embodiments, be set in the order as listed above. Alternatively, the motions to test for biomechanical injuries may be made in any order. In yet other embodiments, the motions to test for biomechanical injuries may be randomized in terms of performance order, and the user performing such motions may be asked to do so according to the randomized order or randomized list of motions. In FIG. 10, screenshots 1000 (i.e., in FIGS. 10A, 10C, 10E, 10G, 10I, 10K, 10M, 10O, and 10Q) depict user 1005, on a mat 1010, both positioned within enclosure 1015 (a portion of which is shown in FIG. 10), with cameras mounted on the enclosure 1015 (the fields of view 1020 of some of the cameras being digitally overlaid on top of the captured images/video of the user 1005 within the enclosure 1015). Screenshots 1000' (i.e., in FIGS. 10B, 10D, 10F, 10H, 10J, 10L, 10N, and 10P) further depict a skeletal framework overlay 1025 being digitally overlaid over the images/video of the user 1005, as the user 1005 performs the motions described above.

In accordance with the methods described above (e.g., with respect to method 400 of FIG. 4 or method 500 of FIG. 5, or the like), the system can determine, based on comparisons of the dynamic relationships among two or more body parts of the user with dynamic relationships among corresponding two or more body parts of each of a plurality of users for each of the sets of motions and/or based on comparisons of the mapped relative positions of the two or more body parts of the user with corresponding mapped relative positions of each of the plurality of users for each of the one or more sets of motions, a physiological status of the user and/or a probability of a physiological status of the user. FIG. 10S is a screenshot 1000" that depicts a summary of the determination of a physiological status or a probability of a physiological status (in this case, embodied as relative injury risk potential, although not limited to such). In particular, FIG. 10S shows that for the second user 1005 whose motions are captured and analyzed in FIGS. 10A-10R, there is little or no risk of hip impingement, groin injury, hamstring injury, a torn ACL, a torn MCL, MTSS in the right leg, or an ankle sprain. However, the second user has a low risk of PFPS in each leg and MTSS in the left leg (as denoted by the "+" blocks).

In some cases, without the system described herein, the human eye may not be able to (or may not be accurately and precisely able to) distinguish the conditions or injury risk potentials of the first and second users. Rather, the different perspectives of the array of cameras capturing real-time images and video in combination with the determination by the computing system taking into account prior data by the same user and by a plurality of users enables such precise and accurate determinations of injury risk potential specifically and physiological status generally of the user under observation.

Although not necessarily shown (except in the '099 application, which has already been incorporated herein by reference in its entirety), the test might include a set of motions, including, but not limited to, two-legged squat, left leg lunge, right leg lunge, left leg squat, right leg squat, left leg balancing, a right leg balancing, vertical jump, box drop, box drop to vertical jump, and shoulder rotations. The motions to test for biomechanical injuries may, in some embodiments, be set in the order as listed above. Alternatively, the motions to test for biomechanical injuries may be made in any order. In yet other embodiments, the motions to test for biomechanical injuries may be randomized in terms of performance order, and the user performing such motions may be asked to do so according to the randomized order or randomized list of motions.

In some cases, having the user perform the lunges first may result in sloppy technique by the user for subsequent motions (i.e., the other motions listed above). Having the user perform the two-legged squat as the first motion in the set of motions, on the other hand, allows the user to quickly find his or her balance and center in order to perform the other techniques or motions; the squat as the first motion in the set of motions also avoids any subsequent sloppy techniques that may result after performing the lunge, even if the lunge is performed as the second motion in the set of motions. With reference to the single leg balances, based on medical studies, having the user perform single leg balances while the user is well rested has little to no predictive value. However, when the user is not rested, single leg balances are very much predictive of various conditions. Accordingly, it is advantageous to have the user perform single leg balances after performing a number of other motions in the set of motions (such as after the squats and lunges, for example). Other than these preferred orderings of particular motions in the set of motions, the other motions in the set of motions can be performed in any suitable or desired order.

The method and system described herein can identify or diagnose these conditions (i.e., potential injury risks or injuries, etc.), based at least in part on analysis of the captured images of the user performing this set of motions. In some embodiments, such analysis might include, without limitation, comparing, with the computing system, the captured images (and in some cases, with the skeletal framework overlay) of the user with baseline captured images (and in some cases, with the skeletal framework overlay) of the same user at an earlier time, and in some cases, also comparing, with the computing system, the captured images (and in some cases, with the skeletal framework overlay) of the user with captured images (and in some cases, with the skeletal framework overlay) of each of a plurality of users (some having been diagnosed as not having a particular injury or injury risk, while others having been diagnosed with particular injuries or injury risks, etc.). In most cases, the human eye is unable to detect the very minute deviation in the relative positions of the body parts (in some cases, represented by the skeletal framework), but the computing system can detect such minute deviations, especially using the techniques described herein.

The types of biomechanical-type injury risks that can be diagnosed by the method and system described herein might include, without limitation, a knee injury (including, but not limited to, torn ACL, torn PCL, torn MCL, torn LCL, and/or the like), an ankle sprain, an Achilles tear, a groin pull, a groin injury, a hamstring strain, a hamstring injury, a hip impingement, shin splints, tennis elbow, MTSS, tibial stress fracture, PFPS, concussion, and/or the like.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method, comprising:
    capturing, with one or more cameras, one or more views of a user within a designated space, as the user is performing one or more sets of motions;
    receiving, with a computing system, the captured one or more views of the user for each of the one or more sets of motions;
    determining, with the computing system, dynamic relationships among two or more body parts of the user for each of the one or more sets of motions, based at least in part on an analysis of the captured one or more views of the user for each of the one or more sets of motions;
    comparing, with the computing system, the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database; and
    determining, with the computing system, a physiological status of the user based at least in part on the comparison of the dynamic relationships among the two or more body parts of the user with dynamic relationships among corresponding two or more body parts of each of a plurality of users for each of the one or more sets of motions;
    wherein determining the physiological status of the user comprises identifying, with the computing system, a type of injury or injury risk that the user has from among types of injuries comprising a knee injury, an ankle sprain, an Achilles tear, a groin pull, a groin injury, a hamstring strain, a hamstring injury, a hip impingement, shin splints, tennis elbow, medial tibial stress syndrome ("MTSS"), tibial stress fracture, and patellofemoral pain syndrome ("PFPS"), based at least in part on the comparison of the dynamic relationships among the two or more body parts of the user with dynamic relationships among corresponding two or more body parts of each of a plurality of users for each of the one or more sets of motions.

2. The method of claim 1, wherein capturing one or more views of a user within a designated space, as the user is performing one or more sets of motions comprises capturing, with one or more cameras, one or more views of a user within a designated space, as the user is performing one or more sets of motions using marker-less motion capture.

3. The method of claim 1, wherein the one or more cameras comprise an array of cameras around the user within the designated space, and wherein the one or more views of the user comprise one or more perspective or elevation views of the user within the designated space.

4. The method of claim 1, wherein the one or more cameras comprise at least one of one or more stationary cameras, one or more cameras mounted on mechanical arms, one or more aerial drone-based cameras, or one or more ground-type drone-based cameras.

5. The method of claim 1, wherein the designated space is one of an indoor space, a man-made portable enclosure, an outdoor space, a sports stadium, an athletic field, an ice rink, a ski slope, a trail, a roadway, or a pathway.

6. The method of claim 1, wherein the designated space is an outdoor space and the method further comprises:
    filtering, with the computing system, lighting-related artifacts in each of the captured one or more views of the user for each of the one or more sets of motions, prior to determining dynamic relationships among the two or more body parts of the user for each of the one or more sets of motions.

7. The method of claim 1, wherein determining dynamic relationships among two or more body parts of the user for each of the one or more sets of motions comprises:
    overlaying, with the computing system, a virtual skeletal framework over at least portions of a body of the user in the captured one or more views of the user for each of the one or more sets of motions;
    mapping, with the computing system, relative positions of the two or more body parts based on the overlaid virtual skeletal framework, for each of the one or more sets of motions; and
    determining, with the computing system, dynamic relationships among two or more body parts of the user for each of the one or more sets of motions, based at least in part on the mapped relative positions of the two or more body parts.

8. The method of claim 7, wherein comparing the dynamic relationships among the two or more body parts of the user with dynamic relationships among corresponding two or more body parts of each of a plurality of users for each of the one or more sets of motions comprises comparing, with the computing system, the dynamic relationships among the two or more body parts of the user with dynamic relationships among corresponding two or more body parts of each of a plurality of users for each of the one or more sets of motions by comparing the mapped relative positions of the two or more body parts of the user with corresponding mapped relative positions of each of the plurality of users for each of the one or more sets of motions.

9. The method of claim 1, wherein the two or more body parts of the user comprise at least two of one or more toes, at least one ankle, at least one knee, at least one hip, at least one shoulder, at least one elbow, at least one wrist, one or more fingers, a neck, or a skull of the user.

10. The method of claim 1, wherein the the types of injuries further comprise a concussion, a torn anterior cruciate ligament ("ACL"), a torn posterior cruciate ligament ("PCL"), a torn medial collateral ligament ("MCL"), and a torn lateral collateral ligament ("LCL").

11. The method of claim 1, wherein determining a physiological status of the user comprises determining, with the computing system, a probability of a physiological status of the user based at least in part on the comparison of the dynamic relationships among the two or more body parts of the user with dynamic relationships among corresponding two or more body parts of each of a plurality of users for each of the one or more sets of motions.

12. The method of claim 1, further comprising:
sending, with the computing system and to one or more user devices, a notification indicating the physiological status of the user.

13. The method of claim 12, wherein sending a notification indicating the physiological status of the user comprises sending, with the computing system and to one or more user devices, a notification indicating the physiological status of the user via a software application ("app"), for display in a graphical user interface of the software app.

14. The method of claim 12, wherein sending a notification indicating the physiological status of the user comprises sending, with the computing system and to one or more user devices, at least one of a text message, a short message service ("SMS") message, a multimedia messaging service ("MMS") message, an e-mail message, or a chat message, each such message comprising the notification indicating the physiological status of the user.

15. The method of claim 12, wherein the one or more user devices comprise at least one of a smartphone, a mobile phone, a personal digital assistant, a tablet computer, a laptop computer, a desktop computer, or a server computer.

16. The method of claim 1, further comprising:
sending, with the computing system and to one or more user devices, a remediation plan to prevent occurrence of the physiological status of the user.

17. The method of claim 1, further comprising:
storing, with the computing system and in the database, the dynamic relationships among the two or more body parts of the user together with the dynamic relationships among corresponding two or more body parts of the plurality of users for each of the one or more sets of motions.

18. The method of claim 17, wherein retrieving or storing the dynamic relationships among the two or more body parts of each of the user and the plurality of users from or in the database is performed over a network.

19. An image-based physiological diagnostic system, comprising:
one or more cameras that capture one or more views of a user within a designated space, as the user is performing one or more sets of motions; and
a computing system, the computing system comprising:
at least one processor; and
at least one non-transitory computer readable medium communicatively coupled to the at least one processor, the at least one non-transitory computer readable medium having stored thereon computer software comprising a set of instructions that, when executed by the at least one processor, causes the computing system to:
receive, from the one or more cameras, the captured one or more views of the user for each of the one or more sets of motions;
determine dynamic relationships among two or more body parts of the user for each of the one or more sets of motions, based at least in part on an analysis of the captured one or more views of the user for each of the one or more sets of motions;
compare the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database; and
determine a physiological status of the user based at least in part on the comparison of the dynamic relationships among the two or more body parts of the user with dynamic relationships among corresponding two or more body parts of each of a plurality of users for each of the one or more sets of motions;
wherein determining the physiological status of the user comprises identifying a type of injury or injury risk that the user has from among types of injuries comprising a knee injury, an ankle sprain, an Achilles tear, a groin pull, a groin injury, a hamstring strain, a hamstring injury, a hip impingement, shin splints, tennis elbow, medial tibial stress syndrome ("MTSS"), tibial stress fracture, and patellofemoral pain syndrome ("PFPS"), based at least in part on the comparison of the dynamic relationships among the two or more body parts of the user with dynamic relationships among corresponding two or more body parts of each of a plurality of users for each of the one or more sets of motions.

20. A method, comprising:
receiving, with a computing system, captured one or more views of the user within a designated space, as the user is performing one or more sets of motions;
determining, with the computing system, dynamic relationships among two or more body parts of the user for each of the one or more sets of motions, based at least in part on an analysis of the captured one or more views of the user for each of the one or more sets of motions;
comparing, with the computing system, the dynamic relationships among the two or more body parts of the user with dynamic relationships among corresponding two or more body parts of each of a plurality of users for each of the one or more sets of motions, the corresponding two or more body parts of each of the plurality of users for each of the one or more sets of motions being retrieved from a database; and
determining, with the computing system, a physiological status of the user based at least in part on the comparison of the dynamic relationships among the two or more body parts of the user with dynamic relationships among corresponding two or more body parts of each of a plurality of users for each of the one or more sets of motions;
wherein determining the physiological status of the user comprises identifying, with the computing system, a type of injury or injury risk that the user has from among types of injuries comprising a knee injury, an ankle sprain, an Achilles tear, a groin pull, a groin injury, a hamstring strain, a hamstring injury, a hip impingement, shin splints, tennis elbow, medial tibial stress syndrome ("MTSS"), tibial stress fracture, and patellofemoral pain syndrome ("PFPS"), based at least in part on the comparison of the dynamic relationships among the two or more body parts of the user with dynamic relationships among corresponding two or more body parts of each of a plurality of users for each of the one or more sets of motions.

* * * * *